US011041023B2

(12) United States Patent
Vale et al.

(10) Patent No.: US 11,041,023 B2
(45) Date of Patent: Jun. 22, 2021

(54) CHIMERIC ANTIGEN RECEPTORS FOR PHAGOCYTOSIS

(71) Applicant: The Regents of the University of California, Oakland, CA (US)

(72) Inventors: Ronald D. Vale, Tiburon, CA (US); Meghan A. Morrissey, San Francisco, CA (US); Adam P. Williamson, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/821,551

(22) Filed: Mar. 17, 2020

(65) Prior Publication Data
US 2020/0239592 A1 Jul. 30, 2020

Related U.S. Application Data

(63) Continuation of application No. PCT/US2019/060052, filed on Nov. 6, 2019.

(60) Provisional application No. 62/756,235, filed on Nov. 6, 2018.

(51) Int. Cl.
*C07K 16/30* (2006.01)
*C07K 14/47* (2006.01)

(52) U.S. Cl.
CPC .......... *C07K 16/30* (2013.01); *C07K 14/4748* (2013.01); *C07K 2317/622* (2013.01); *C07K 2319/03* (2013.01); *C07K 2319/09* (2013.01)

(58) Field of Classification Search
CPC .................. C07K 16/00–468; C07K 2319/03
See application file for complete search history.

(56) References Cited

U.S. PATENT DOCUMENTS

| | | | |
|---|---|---|---|
| 6,210,963 B1 | 4/2001 | Haddada et al. | |
| 8,198,020 B2 | 6/2012 | Francois et al. | |
| 8,709,412 B2 | 4/2014 | Jones et al. | |
| 9,045,541 B2 | 6/2015 | Eckelman et al. | |
| 9,149,519 B2 | 10/2015 | Landau et al. | |
| 9,221,908 B2 | 12/2015 | Frazier et al. | |
| 9,518,116 B2 | 12/2016 | Frazier et al. | |
| 9,663,575 B2 | 5/2017 | Eckelman et al. | |
| 9,745,368 B2 | 8/2017 | Milone et al. | |
| 9,845,345 B2 | 12/2017 | Ring et al. | |
| 10,034,900 B2 | 7/2018 | Senju | |
| 10,081,680 B2 | 9/2018 | Weiskopf et al. | |
| 10,106,609 B2 | 10/2018 | Yang et al. | |
| 10,259,859 B2 | 4/2019 | Pons et al. | |
| 10,259,873 B2 | 4/2019 | Frazier et al. | |
| 10,415,017 B2 | 9/2019 | O'Neill | |
| 10,428,143 B2 | 10/2019 | Krummel et al. | |
| 10,774,125 B2 | 9/2020 | Ring et al. | |
| 2004/0053873 A1 | 3/2004 | Barman et al. | |
| 2006/0188891 A1 | 8/2006 | Bickmore, Jr. et al. | |
| 2008/0254027 A1 | 10/2008 | Bernett et al. | |
| 2011/0250203 A1 | 10/2011 | Klitgaard et al. | |
| 2014/0134142 A1 | 5/2014 | Smith et al. | |
| 2014/0140989 A1 | 5/2014 | Eckelman et al. | |
| 2014/0161805 A1 | 6/2014 | Jamieson et al. | |
| 2014/0242701 A1 | 8/2014 | Shiku et al. | |
| 2015/0057161 A1 | 2/2015 | Schultze et al. | |
| 2015/0274826 A1 | 10/2015 | Frazier et al. | |
| 2016/0137733 A1 | 5/2016 | Frazier et al. | |
| 2016/0250258 A1 | 9/2016 | Delaney et al. | |
| 2016/0251435 A1 | 9/2016 | Eckelman et al. | |
| 2017/0087185 A1 | 3/2017 | Crane et al. | |
| 2017/0151281 A1 | 6/2017 | Wagner et al. | |
| 2017/0151282 A1 | 6/2017 | Discher et al. | |
| 2017/0166657 A1 | 6/2017 | O'Neill et al. | |
| 2017/0226183 A1 | 8/2017 | Schiffer-Mannioui | |
| 2017/0233452 A1 | 8/2017 | McIvor et al. | |
| 2017/0246278 A1 | 8/2017 | Vera Valdes et al. | |
| 2017/0283498 A1 | 10/2017 | Frazier et al. | |
| 2017/0292118 A1 | 10/2017 | Duchateau et al. | |
| 2018/0000899 A1 | 1/2018 | Francois et al. | |
| 2018/0057592 A1 | 3/2018 | Frazier et al. | |
| 2018/0104308 A1 | 4/2018 | Mamonkin et al. | |
| 2018/0105600 A1 | 4/2018 | Pons et al. | |

(Continued)

FOREIGN PATENT DOCUMENTS

| | | |
|---|---|---|
| CA | 2850380 C | 8/2015 |
| EP | 2626415 A2 | 8/2013 |

(Continued)

OTHER PUBLICATIONS

Morrissey et al., eLife 2018;7:e36688, pp. 1-21 (Year: 2018).*
Ali, M. et al., "Induction of neoantigen-reactive T cells from healthy donors", Nature Protocols (2019).
Alvey C. et al. (2017). "Engineering macrophages to eat Cancer: from "marker of self" CD47 and phagocytosis to differentiation," Journal of Leukocyte Biology 102:31-40.
Alvey C.M. et al. (2017). "SIRPA-Inhibited, Marrow-Derived macrophages engorge, accumulate, and differentiate in Antibody-Targeted regression of solid tumors," Current Biology 27:2065-2077.
Andreesen R, et al. 1990. Adoptive transfer of tumor cytotoxic macrophages generated in vitro from circulating blood monocytes: a new approach to Cancer immunotherapy. Cancer Research 50:7450-7456.

(Continued)

*Primary Examiner* — Jessica H Roark
(74) *Attorney, Agent, or Firm* — Terri Shieh-Newton; David Dang; Mintz, Levin, Cohn, Ferris, Glovsky and Popeo, P.C.

(57) ABSTRACT

The present disclosure generally relate to chimeric antigen receptors (CARs) that bind an engulfment receptor expressed on the surface of a phagocytic cell and activate the endogenous phagocytic signaling pathway. Also disclosed are compositions and methods useful for producing such CARs, nucleic acids encoding same, phagocytic cells that have been modified to include a targeted effector activity directed towards a cell of interest such as, e.g., a cancer cell, as well as for modifying a cell and/or for the treatment of various health disorders such as cancer, including solid tumor and hematologic malignancy.

19 Claims, 25 Drawing Sheets

Specification includes a Sequence Listing.

(56) References Cited

U.S. PATENT DOCUMENTS

| | | |
|---|---|---|
| 2018/0133252 A9 | 5/2018 | Wilson et al. |
| 2018/0142019 A1 | 5/2018 | Manning et al. |
| 2018/0171021 A1 | 6/2018 | Karlsson et al. |
| 2018/0186878 A1 | 7/2018 | Rosenthal |
| 2018/0221503 A1 | 8/2018 | Kadiyala et al. |
| 2018/0244748 A1 | 8/2018 | Gill et al. |
| 2018/0250395 A1 | 9/2018 | Pietsch et al. |
| 2018/0319883 A1 | 11/2018 | Weiskopf et al. |
| 2018/0325953 A1 | 11/2018 | Poznansky et al. |
| 2019/0023761 A1 | 1/2019 | Pule et al. |
| 2019/0038671 A1 | 2/2019 | Fan et al. |
| 2019/0062450 A1 | 2/2019 | De Palma et al. |
| 2019/0070277 A1 | 3/2019 | O'Neill et al. |
| 2019/0112373 A1 | 4/2019 | Manning et al. |
| 2019/0119379 A1 | 4/2019 | Gottschalk et al. |
| 2019/0119396 A1 | 4/2019 | Liu et al. |
| 2019/0144522 A1 | 5/2019 | Bari et al. |
| 2019/0169266 A1 | 6/2019 | Pons et al. |
| 2019/0233496 A1 | 8/2019 | Rosenthal |
| 2019/0240343 A1 | 8/2019 | Ahmed et al. |
| 2019/0248892 A1 | 8/2019 | Frazier et al. |
| 2019/0263928 A1 | 8/2019 | Watanabe et al. |
| 2019/0275150 A1 | 9/2019 | Pincetic et al. |
| 2019/0336615 A1 | 11/2019 | Thompson et al. |
| 2019/0345217 A1 | 11/2019 | Ma et al. |

FOREIGN PATENT DOCUMENTS

| | | |
|---|---|---|
| EP | 2242512 B1 | 4/2016 |
| EP | 2956343 B1 | 12/2018 |
| EP | 3504244 A1 | 7/2019 |
| EP | 3519441 A1 | 8/2019 |
| GB | 2572005 A | 9/2019 |
| WO | WO-95005835 A1 | 3/1995 |
| WO | WO-2004050855 A2 | 6/2004 |
| WO | WO-2004050855 A3 | 6/2004 |
| WO | WO-2008011599 A2 | 1/2008 |
| WO | WO-2008011599 A3 | 1/2008 |
| WO | WO-2017044487 A1 | 3/2017 |
| WO | WO-2017136633 A1 | 8/2017 |
| WO | WO-2018/064076 A1 | 4/2018 |
| WO | WO-2018169948 A1 | 9/2018 |
| WO | WO-2019005641 A1 | 1/2019 |
| WO | WO-2019032624 A1 | 2/2019 |
| WO | WO-2019067328 A1 | 4/2019 |
| WO | WO-2019070704 A1 | 4/2019 |
| WO | WO-2019086512 A1 | 5/2019 |
| WO | WO-2019129146 A1 | 7/2019 |
| WO | WO-2019191332 A1 | 10/2019 |
| WO | WO-2019191334 A1 | 10/2019 |
| WO | WO-2019191340 A1 | 10/2019 |
| WO | WO-2020097193 A1 | 5/2020 |

OTHER PUBLICATIONS

Andreu N. et al. 2017. Primary macrophages and J774 cells respond differently to infection with *Mycobacterium tuberculosis*. Scientific Reports 7:42225.

Batista, F.D. et al. 2001. "B cells acquire antigen from target cells after synapse formation," Nature 411:489-494.

Beningo KA et al. 2002. Fc-receptor-mediated phagocytosis is regulated by mechanical properties of the target. Journal of Cell Science 115:849-856.

Berger, et al., "Efficient Elutriation of monocytes within a closed system (Elutra™) Journal of Immunological Methods 298 (2005) 61-72".

Bhattacharjee, J., et al., "Monocytes isolated by positive and negative magnetic sorting techniques show different molecular characteristics and immunophenotypic behaviour", F100Research (2018) pp. 1-13.

Biglari, A., et al. Human monocytes expressing a CEA-specific chimeric CD64 receptor specifically target CEA-expressing tumour cells in vitro and in vivo, Gene Therapy (2006) 13, 602-610.

Brooks, S.R. et al. 2004. Binding of cytoplasmic proteins to the CD19 intracellular domain is high affinity, competitive, and multimeric. The Journal of Immunology 172:7556-7564.

Bu, J.Y. et al. 1995. Analysis of the interaction of ZAP-70 and syk protein-tyrosine kinases with the T-cell antigen receptor by plasmon resonance. PNAS 92:5106-5110.

Chao, M.P. et al. 2010. Anti-CD47 antibody synergizes with rituximab to promote phagocytosis and eradicate non-Hodgkin lymphoma. Cell 142:699-713.

Chen, J. et al. 2017. SLAMF7 is critical for phagocytosis of haematopoietic tumour cells via Mac-1 integrin. Nature 544:493-497.

Chen, X. et al. (Sep. 1, 2018, e-published Jul. 18, 2018). "Functional Interrogation of Primary Human T Cells via Crispr Genetic Editing," J Immunol 201(5):1586-1598.

Corresponding PCT Application No. PCT/US2019/060052, filed Nov. 6, 2019.

Cros, J. et al., (Sep. 24, 2010). "Human CD14dim) Monocytes Patrol and Sense Nucleic Acids and ciruses via TLR7 and TLR8 Receptors," Immunity 33, 375-386.

Cross, S.E. et al. (2007). "Nanomechanical analysis of cells from cancer patients," Nature Nanotechnology 2:780-783.

Davis, S.J. et al. 2006. The kinetic-segregation model: TCR triggering and beyond. Nature Immunology 7:803-809.

De Oliveria, S, et al., "Modification of Hematopoietic Stem/Progenitor Cells with CD19-Specific Chimeric Antigen Receptors as a Novel Approach for Cancer Immunotherapy" Human Gene Therapy 24:824-839 (Oct. 2013).

Edelstein, A. et al. 2010. Computer control of microscopes using µmanager. Current Protocols in Molecular Biology 14:Unit14.20.

Engel, P. et al. 1995. Abnormal B lymphocyte development, activation, and differentiation in mice that lack or overexpress the CD19 signal transduction molecule. Immunity 3:39-50.

Fesnak, A.D. et al. 2016. Engineered T cells: the promise and challenges of cancer immunotherapy. Nature Reviews Cancer 16:566-581.

Fraser, A., et al, "Development, functional characterization and validation of methodology for GMP-compliant manufacture of phagocytic macrophages: A novel cellular therapeutic for liver cirrhosis", Cyotherapy, 2017, ISSN 1465-3249.

Freeman, S.A. et al. 2016. Integrins Form an Expanding Diffusional Barrier that Coordinates Phagocytosis. Cell 164: 128-140.

Freeman, S.A.et al. 2014. Phagocytosis: receptors, signal integration, and the cytoskeleton. Immunological Reviews 262:193-215.

Gardai, S.J. et al. 2005. Cell-surface calreticulin initiates clearance of viable or apoptotic cells through trans-activation of LRP on the phagocyte. Cell 123:321-334.

Geissmann, et al., "Blood Monocytes Consist of Two Principal Subsets with Distinct Migratory Properties", Immunity, vol. 19, pp. 71-82, Jul. (2003).

Getts, D.R., "Microparticles bearing encephalitogenic peptides induce T-cell tolerance and ameliorate experimental autoimmune encephalomyelitis", Nat Biotechnol. Dec. 2012; 30(12): 1217-1224.

Goudot, C. et al., "Aryl Hydrocarbon Receptor Controls Monocyte Differentiation into Dendritic Cells versus Macrophages", Sep. 19, 2017 Immunity 47, 582-596.

Harshyne, L.A. et al. 2003. A Role for Class a Scavenger Receptor in Dendritic Cell Nibbling from Live Cells. The Journal of Immunology 170:2302-2309.

Harshyne, L.A. et al. 2001. Dendritic cells acquire antigens from live cells for Cross-Presentation to CTL. The Journal of Immunology 166:3717-3723.

Haso, W. et al. 2013. Anti-CD22-chimeric antigen receptors targeting B-cell precursor acute lymphoblastic leukemia. Blood 121:1165-1174.

Huang, M-N. et al., "Antigen-loaded monocyte administration induces potent therapeutic antitumor T cell responses", The Journal of Clinical Investigation, Jan. 6, 2020, 130(2):774-788.

Hui, E. et al. 2014. In vitro membrane reconstitution of the T-cell receptor proximal signaling network. Nature Structural & Molecular Biology 21:133-142.

International Search Repot dated Apr. 30, 2020 for PCT Application No. PCT/US2019/060052, filed Nov. 6, 2019, 5 pages.

(56) References Cited

OTHER PUBLICATIONS

Ingersoll, B. "Brief Report: Pilot Randomized Controlled Trial of Reciprocal Imitation Training for Teaching Elicited and Spontaneous Imitation to Children with Autism", J Autism Dev Disord. Sep. 2010; 40(9): 1154-1160.
Jadus, M.R. et al. 1996. Macrophages can recognize and kill tumor cells bearing the membrane isoform of macrophage colony-stimulating factor. Blood 87:5232-5241.
Jaiswal S. et al. 2009. CD47 is upregulated on circulating hematopoietic stem cells and leukemia cells to avoid phagocytosis. Cell 138:271-285.
James, J. R. et al. 2012. Biophysical mechanism of T-cell receptor triggering in a reconstituted system. Nature 487:64-69.
Joly, E. et al. 2003. What is trogocytosis and what is its purpose? Nature Immunology 4:815.
Kao, G. et al. 2006. The role of the laminin beta subunit in laminin heterotrimer assembly and basement membrane function and development in C. elegans. Developmental Biology 290:211-219.
Kim, S. et al., "Monocyte Enrichment from Leukapheresis products by using the Elutra cell separator". Transfusion, vol. 47, Dec. 2007 pp. 2290-2296.
Kochenderfer, J.N. et al. 2009. Construction and preclinical evaluation of an anti-CD19 chimeric antigen receptor. Journal of Immunotherapy 32:689-702.
Lacerna, L.V. et al. 1988. Adoptive cancer immunotherapy utilizing lymphokine activated killer cells and gamma interferon activated killer monocytes. Pharmacology & Therapeutics 38:453-465.
Lee, S. et al. 2016. Macrophage-based cell therapies: the long and winding road. Journal of Controlled Release 240:527-540.
Lim, W.A. et al. 2017. The Principles of Engineering Immune Cells to Treat Cancer. Cell 168:724-740.
Lim, K.H. et al. (Jul. 9, 2020). "Antisense oligonucleotide modulation of non-productive alternative splicing upregulates gene expression," Nat Commun 11(1):3501.
Liu, X. et al. 2015. CD47 blockade triggers T cell-mediated destruction of immunogenic tumors. Nature Medicine 21:1209-1215.
Majeti, R. et al. 2009. CD47 is an adverse prognostic factor and therapeutic antibody target on human acute myeloid leukemia stem cells. Cell 138:286-299.
Matsuyoshi, H., et al., "Enchanced Priming of Antigen-Specific CTL's in Vivo by Embryonic Stem Cell-Derived Dendritic Cells Expressing Chemokine Along with Antigenic Protein: Application to Antitumor Vaccination", The Journal of Immunology (2004) 172:776-786.
Mayordomo, J.I. et al. 1995. Bone marrow-derived dendritic cells pulsed with synthetic tumour peptides elicit protective and therapeutic antitumour immunity. Nature Medicine 1:1297-1302.
Mildner, A., et al., "Distinct and Non-Redundant Roles of Microglia and Myeloid Subsets in Mouse Models of Alzheimer's Disease" Neurobiology of Disease, J. Neurosci., Aug. 3, 2011, 31(31):11159-11171.
Morrissey, M.A. et al. (Jun. 4, 2018). "Chimeric antigen receptors that trigger phagocytosis," *eLife* 7:e36688.

Mukherjee, R. et al., "Non-Classical monocytes display inflammatory features: Validation in Sepsis and Systemic Lupus Erythematous", Scientific Reports, (2015) pp. 1-14.
Murshid, A. et al, "Hsp90-peptide complexes stimulate antigen presentation through the class II pathway after binding scavenger receptor SREC-1", Immunobiology, Dec. 2014; 219(12); 924-931.
Passlick, B. et al., "Identification and Characterization of a Novel Monocyte Subpopulation in Human Peripheral Blood", Article in Blood, Dec. 1989, 74: 2527-2534.
Penberthy, K.K. et al. 2016. Apoptotic cell recognition receptors and scavenger receptors. Immunological Reviews 269:44-59.
Ralston, K.S. et al. 2014. Trogocytosis by Entamoeba histolytica contributes to cell killing and tissue invasion. Nature 508:526-530.
Roberts, E.W. et al. 2016. Critical Role for CD103(+)/CD141(+) Dendritic Cells Bearing CCR7 for Tumor Antigen Trafficking and Priming of T Cell Immunity in Melanoma. Cancer Cell 30:324-336.
Roberts, M. R. et al. "Antigen-Specific Cytolysis by Neutrophils and NK Cells Expressing Chimeric Immune Receptros Bearing xx Signaling Domains", J Immunol 1998; 161:375-384.
Rosales, C. et al, "Phagocytosis: A Fundamental Process in Immunity", BioMed Research International, vol. 2017, Article ID 9042851, 18 pages., (2017).
Ruiz-Aguilar, S., et al., "Human CD16+ and CD16+ monocyte subsets display unique effector properties in inflammatory conditions in vivo", Journal of Leukocyte Biology, (2011) vol. 90, pp. 1119-1131.
Schlam, D. et al. (Oct. 14, 2015). "Phosphoinositide 3-kinase enables phagocytosis of large particles by terminating actin assembly through Rac/Cdc42 GTPase-activating proteins," Nat Commun 6(1):8623.
Senju, S., et al., "Generation and genetic modification of dendritic cells derived from mouse embryonic stem cells derived from mouse embryonics stem cells", Blood, May 1, 2003, vol. 101, No. 9, pp. 3501-3508.
Tseng, D. et al. 2013. Anti-CD47 antibody-mediated phagocytosis of cancer by macrophages primes an effective antitumor T-cell response. PNAS 110:11103-11108.
Tsutsui, et al. "The use of microbubbles to target drug delivery" Cardiovascular Ultrasound (2004) 2:23.
Tuveson, D.A. et al. 1993. CD19 of B cells as a surrogate kinase insert region to bindphosphatidylinositol 3-kinase. Science 260:986-989.
Weischenfeldt, J. et al. 2008. Bone Marrow-Derived Macrophages (BMM): Isolation and Applications. Cold Spring Harbor Protocols 2008:pdb.prot5080.
Written Opinion dated Apr. 30, 2020 for PCT Application No. PCT/US2019/060052, filed Nov. 6, 2019, 7 pages.
Xiao, W. et al. (Jan. 1997). : Electrophysiological characteristics of primary afferent fibers after systemic administration of anti-GD2 ganglioside antibody, *Pain* 69(1-2):145-151.
Xiao X. et al. 2009. Identification and characterization of fully human anti-CD22 monoclonal antibodies. mAbs 1:297-303.
Yong, C., et al, "A role for multiple chimeric antigen receptor-expressing leukocytes in antigen-specific responses to cancer". (2016) Oncotarget, vol. 7, No. 23 pp. 34582-34598.

* cited by examiner

CHIMERIC ANTIGEN RECEPTORS FOR PHAGOCYTOSIS

CROSS-REFERENCE TO RELATED APPLICATIONS

This application is a continuation of International Patent Application No. PCT/US2019/060052 filed on Nov. 6, 2019, which claims the benefit of priority to U.S. Provisional Patent Application Ser. No. 62/756,235, filed on Nov. 6, 2018. The contents of the above-referenced applications are hereby expressly incorporated by reference in their entireties, including any drawings.

STATEMENT REGARDING FEDERALLY SPONSORED R&D

This invention was made with government support under grant no. F32 GM120990 awarded by the National Institutes of Health. The government has certain rights in the invention.

INCORPORATION OF THE SEQUENCE LISTING

The present application is being filed along with a Sequence Listing in electronic format. The Sequence Listing is provided as a file entitled "Sequence Listing-048536-626C01US.txt", created Mar. 17, 2020, which is approximately 98 KB in size. The information in the electronic format of the Sequence Listing is incorporated herein by reference in its entirety.

FIELD

Aspects of the present application generally relate to novel chimeric antigen receptors (CARs) that bind an engulfment receptor expressed on the surface of a phagocytic cell and activate the endogenous phagocytic signaling pathway. Also provided are compositions and methods useful for producing such CARs, nucleic acids encoding same, phagocytic cells that have been modified to include a targeted effector activity directed against a cell of interest such as, e.g., a cancer cell, as well as methods for modifying a cell and/or for the treatment of various health disorders such as cancers.

BACKGROUND

Immune system constantly patrols human body, looking to eliminate cancerous cells and harmful microbes. Under normal circumstances, immune cells can identify these threats because they can recognize certain signals present at the surface of the target cells. However, cancer cells often find ways to evade from the immune system and proliferate. In addition, the endogenous immune system is typically non-reactive to malignant cells, or can be actively immunosuppressive with respect to the body's reaction to the presence of malignant cells.

Despite many recent advances in cancer immunotherapy, which have significantly accelerated the ability to improve clinical results in the setting of numerous solid tumors and hematologic malignancies, a vast majority of current cellular therapeutics focus almost exclusively on T cells, where one way to enhance treatment of tumors is to force tumor recognition by the immune system through genetic engineering of leukocytes. This focus is largely to the fact that T cells can be engineered to express a synthetic immunoreceptor containing an extracellular targeted antibody and intracellular signaling domain, known as chimeric antigen receptor (CAR), which give the T cells expressing such CAR the new ability to target a tumor-associated antigen. For example, in recent years, T cells expressing a CAR directed against CD19 have been shown to have significant anti-leukemic efficacy, where complete remission has been achieved in 90% of acute lymphoblastic leukemia patients treated. These results are accompanied by robust T cell proliferation and clearly documented T cell infiltration into tumor sites in leukemic patients so treated. Despite the high response rates demonstrated in hematopoietic malignancies, CAR T cell efficacy in solid tumors as well as in certain lymphoid tumors may be limited. Possible explanations for this include the potentially impaired ability of T cells to infiltrate solid tumors, poor trafficking, immunosuppressive tumor microenvironment, and expression of few tumor specific antigens on solid tumor cells.

There is an ongoing need for new compositions and methods of treating infections, inflammatory diseases, immune diseases, and various cancers. In particular, a need exists in the art for more effective compositions and methods that treat cancers by improving specificity for tumor cells and improving infiltration into tumor sites in both solid tumors and hematologic malignancies by such compositions and methods.

SUMMARY

This section provides a general summary of the disclosure, and is not comprehensive of its full scope or all of its feature.

The present disclosure generally relates to the fields of cell biology and immunology. More particularly, provided herein are novel antigen-binding molecules that specifically bind an engulfment receptor expressed on the surface of a phagocytic cell and activate the endogenous phagocytic signaling pathway. Also provided are, inter alia, recombinant cells such as phagocytic cells that have been modified to include a targeted effector activity directed against a cell of interest such as, e.g., a cancer cell. This novel methodology, termed "Chimeric Antigen Receptors for Phagocytosis" (CAR-P), represents a new cellular therapeutic approach targeting cancerous cells. The disclosure also provides compositions and methods useful for producing such antigen-binding molecules, as well as methods for the treatment of health disorders associated with cancer, including solid tumor and hematologic malignancy.

In one aspect, disclosed herein is a pharmaceutical composition including a pharmaceutically acceptable carrier, and one or more of the following: (a) a chimeric polypeptide including: an extracellular domain including an antigen-binding region specific for one or more cancer-associated antigen; a transmembrane domain; at least one copy of an intracellular signaling domain from an engulfment receptor; and at least one copy of a recruitment domain; (b) a nucleic acid encoding the polypeptide of (a); and (c) a recombinant cell including the polypeptide of (a) and/or the nucleic acid of (b).

In one aspect, disclosed herein is a chimeric polypeptide including: (a) an extracellular domain including an antigen-binding region specific for one or more cancer-associated antigen; (b) a transmembrane domain; (c) at least one copy of an intracellular signaling domain from an engulfment receptor; and (d) at least one copy of a recruitment domain.

Implementations of embodiments of the chimeric polypeptide according to the present disclosure can include one or more of the following features. In some embodiments, the chimeric polypeptide further includes a signal peptide operably linked upstream (e.g., N-terminally) to the extracellular domain. In some embodiments, the antigen-binding region includes an amino acid sequence encoding an antibody or a functional fragment thereof selected from the group consisting of an antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment thereof. In some embodiments, the one or more cancer-associated antigens is selected from the group consisting of CD19, CD22, HER2 (ERBB2/neu), Mesothelin, PSCA, CD123, CD30, CD171, CD138, CS-1, CLECL1, CD33, CD79b, EGFRvIII, GD2, GD3, BCMA, PSMA, ROR1, FLT3, TAG72, CD38, CD44v6, CEA, EPCAM, B7H3 (CD276), KIT (CD 117), CD213A2, IL-1 IRa, PRSS21, VEGFR2, CD24, MUC-16, PDGFR-beta, SSEA-4, CD20, MUC1, EGFR, NCAM, Prostase, PAP, ELF2M, Ephrin B2, FAP, EphA2, GM3, TEM1/CD248, TEM7R, CLDN6, TSHR, GPRC5D, CD97, CD179a, ALK, and IGLL1. In some embodiments, the one or more cancer-associated antigens is selected from the group consisting of CD19 and CD22. In some embodiments of the disclosure, the intracellular signaling domain of the engulfment receptor includes at least 1, at least 2, at least 3, at least 4, or at least 5 immunoreceptor tyrosine-based activation motifs (ITAMs). In some embodiments, the intracellular signaling domain from the engulfment receptor is capable of mediating endogenous phagocytic signaling pathway. In some embodiments, the engulfment receptor is selected from the group consisting of Megf10, FcRγ, Bai1, MerTK, TIM4, Stabilin-1, Stabilin-2, RAGE, CD300f, Integrin subunit αv, Integrin subunit β5, CD36, LRP1, SCARF1, C1Qa, and Axl.

In some embodiments, the transmembrane domain includes a stalk and/or transmembrane domain derived from CD8, Megf10, FcRγ, Bai1, MerTK, TIM4, Stabilin-1, Stabilin-2, RAGE, CD300f, Integrin subunit αv, Integrin subunit β5, CD36, LRP1, SCARF1, C1Qa, Axl, CD45, or CD86. In some embodiments, the transmembrane domain is operably linked downstream of the extracellular domain and upstream of the at least one copy of the intracellular signaling domain from the engulfment receptor. In some embodiments, the signal peptide includes a signal peptide derived from CD8, Megf10, FcRγ, Bai1, MerTK, TIM4, Stabilin-1, Stabilin-2, RAGE, CD300f, Integrin subunit αv, Integrin subunit β5, CD36, LRP1, SCARF1, C1Qa, and/or Axl.

In some embodiments, the at least one copy of a recruitment domain includes: (a) a p85-binding domain derived from CD19, Gab2, IREM-1, PDGF receptor, CSFR-1, c-Kit, ErbB3, or CD7 to recruit the p85 regulatory subunit of phosphoinositide 3-kinase (PI3K); (b) an SH3 domain derived from Crk, Cdc25, Phospholipase, Ras, Vav, GRB2, FAK, Pyk2, TRIP10, or Gads to recruit cytosolic signaling proteins; and/or (c) a proline-rich peptide from C3G, p41, PEP, p47, HPK1, SLP-1, CD3ε, PAK, AIP4, or Sos to recruit SH3 domain-containing proteins. In some embodiments, the recruitment domain is operably linked downstream to the at least one copy of the intracellular signaling domain of the engulfment receptor. In some embodiments, the recruitment domain is operably linked downstream (e.g., C-terminally) to the transmembrane domain and upstream to the at least one copy of the intracellular signaling domain of the engulfment receptor. In some embodiments of the disclosure, the chimeric polypeptide further includes one or more peptide linker sequences. In some embodiments, the one or more peptide linker sequences includes a glycine-serine linker.

In some embodiments of the present disclosure, the chimeric polypeptide includes (a) a peptide signal; (b) an extracellular domain including an antigen-binding region specific for one or more cancer-associated antigens; (c) a transmembrane domain; (d) an intracellular signaling domain from an engulfment receptor; and (e) a p85-recruitment domain. In some embodiments, the chimeric polypeptide includes (a) a peptide signal from CD8; (b) an extracellular single chain antibody variable fragment (scFv) having specific affinity for CD19 or CD22; (c) a transmembrane domain from CD8; (d) an intracellular signaling domain from Megf10, FcRγ, Bai1, or MerTK; and (e) a p85-recruitment domain from CD19.

In some embodiments, the chimeric polypeptide of the disclosure includes an amino acid sequence having at least 80% sequence identity to a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9.

In one aspect, some embodiments of the disclosure relate to an isolated, synthetic, or recombinant nucleic acid molecule including a nucleic acid sequence encoding a polypeptide that includes an amino acid sequence having at least 90% identity to the amino acid sequence of a chimeric polypeptide as disclosed herein, or a functional fragment thereof. In some embodiments, the nucleic acid sequence has at least 80% sequence identity to a nucleic acid sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18. In some embodiments, the nucleic acid sequence is operably linked to a heterologous nucleic acid sequence. In some embodiments, the nucleic acid molecule of the disclosure is an expression cassette or an expression vector.

In another aspect, some embodiments of the disclosure relate to a recombinant cell including an isolated, synthetic, or recombinant nucleic acid molecule as disclosed herein. In some embodiments, the recombinant cell is a prokaryotic cell or a eukaryotic cell. In some embodiments, the recombinant cell is a human cell. In some embodiments, the recombinant cell is a phagocytic cell. In some embodiments, the phagocytic cell is selected from the group consisting of macrophages, dendritic cells, mast cells, monocytes, neutrophils, microglia, and astrocytes. In some embodiments, the phagocytic cell is a bone marrow derived macrophage (BMDM) or a bone marrow derived dendritic cell (BMDC). In another aspect, some embodiments of the disclosure relate to a cell culture including at least one recombinant cell as disclosed herein and a culture medium.

In one aspect, some embodiments of the disclosure relate to a pharmaceutical composition including: (a) a chimeric polypeptide as described herein; (b) an isolated, synthetic, or recombinant nucleic acid molecule as described herein; and/or (c) a recombinant cell as described herein, and a pharmaceutically acceptable carrier. In some embodiments, the recombinant cell is a human cell. In some embodiments, the recombinant cell is a phagocytic cell selected from the group consisting of macrophages, dendritic cells, mast cells, monocytes, neutrophils, microglia, and astrocytes. In some embodiments, the phagocytic cell is a bone marrow derived macrophage (BMDM) or a bone marrow derived dendritic cell (BMDC).

In another aspect, some embodiments of the disclosure relate to method for modifying a cell, including introducing into the cell (a) a chimeric polypeptide as described herein; and/or (b) an isolated, synthetic, or recombinant nucleic acid molecule as described herein. In some embodiments, the cell is a phagocytic cell. In some embodiments, the phagocytic cell is selected from the group consisting of macrophages, dendritic cells, mast cells, monocytes, neutrophils, microglia, and astrocytes.

In another aspect, some embodiments of the disclosure relate to method for treating an individual having cancer, which includes administering to the individual an effective numbers of phagocytic cells that have been modified to express a chimeric engulfment receptor having specific affinity for an antigen associated with a cancer cell. In some embodiments, the cell is a phagocytic cell selected from the group consisting of macrophages, dendritic cells, mast cells, monocytes, neutrophils, microglia, and astrocytes. In some embodiments, the phagocytic cell is a BMDM or a BMDC. In some embodiments, the phagocytic cell is derived from the same individual having cancer.

In another aspect, some embodiments of the disclosure relate to method for treating an individual having cancer, which includes administering to the individual an effective amount or number of: (a) a chimeric polypeptide as described herein; (b) an isolated, synthetic, or recombinant nucleic acid molecule as described herein; (c) a recombinant cell as described herein; and/or a pharmaceutical composition as described herein. In some embodiments, the administration includes a viral-, particle-, liposome-, or exosome-based delivery procedure. In some embodiments, the administration includes delivering into endogenous cells ex vivo one or more gene-editing enzymes targeting (a) a chimeric polypeptide as described herein; and/or (b) an isolated, synthetic, or recombinant nucleic acid molecule as described herein. In some embodiments, the administration includes delivering into cells in vivo one or more gene-editing enzymes targeting (a) a chimeric polypeptide as described herein; and/or (b) an isolated, synthetic, or recombinant nucleic acid molecule as described herein. In some embodiments, the administration activates phagocytosis of said cancer cell. In some embodiments, the activated phagocytosis includes whole-cell internalization and/or bite internalization. In some embodiments, the cancer is selected from the group consisting of breast cancer, ovarian cancer, lung cancer, pancreatic cancer, mesothelioma, leukemia, lymphoma, brain cancer, prostate cancer, multiple myeloma, melanoma, bladder cancer, bone sarcomas, soft tissue sarcomas, retinoblastoma, renal tumors, neuroblastoma, and carcinomas.

In yet another aspect, provided herein is a kit having any of the composition described above and further having instructions for use.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 1A schematically depicts the structure of number of non-limiting examples of the CAR-P constructs described herein. An αCD19 (left and right constructs) or αCD22 (center) scFv directs CAR specificity. Intracellular signaling domains from Megf10 or the indicated engulfment receptor activate engulfment. CAR-P$^{GFP}$ contains only GFP and no intracellular signaling domains (right). All constructs include a transmembrane domain from CD8 and a C-terminal GFP. FIG. 1B: J774A.1 macrophages expressing αCD19 CAR-P with the indicated intracellular signaling domain engulf 5 μm silica beads covered with a supported lipid bilayer containing His-tagged CD19 extracellular domain. The beads were visualized with atto390-labeled lipid incorporated into the supported lipid bilayer. Cells infected with the cell membrane marker, mCherry-CAAX, were used as a control (no CAR, top left). To the right of each image is a histogram depicting the frequency of cells engulfing the indicated number of beads. The average number of beads eaten per cell is quantified in FIG. 1C. As shown in FIG. 1D, bone marrow derived macrophages (BMDMs) were infected with CAR-P$^{FcR\gamma}$ or GFP-CAAX (green, left and center top; grey, center bottom) and incubated with CD19 beads (magenta) for 45 min. Images show an x-y plane through the center of the engulfed beads (left), or a cross section (center) of the z plane indicated in the inset panel (white line). The histogram depicts the number of cells engulfing the indicated number of beads. The scale bar indicates 5 μm and n=78-163 cells per condition, collected during three separate experiments. Error bars denote 95% confidence intervals and *** indicates p<0.0001 compared to mCherry-CAAX control by Kruskal-Wallis test with Dunn's multiple comparison correction. FIG. 1E depicts a non-limiting example of the expression level of CAR-P constructs in macrophages. Images of macrophages infected with various αCD19 CAR-P$^{GFP}$ constructs were acquired with identical acquisition settings and scaling to depict differences in expression levels. Fluorescent intensity at the cell cortex of 20 representative αCD19 CAR-P$^{GFP}$-infected macrophages was quantified using the mean intensity of a 2 pixel width linescan at the cell membrane, minus the mean intensity of a linescan immediately adjacent to the cell. The images are the same cells included in FIG. 1B and fluorescent intensity was measured from the same macrophages assayed in FIG. 1C. The scale bar indicates 5 μm.

FIG. 2A: Macrophages infected with the αCD19 or αCD22 CAR-P$^{Megf10}$ or mCherry-CAAX control were fed 5 mm beads ligated with either CD19 (left panel) or CD22 (right panel). Engulfment is quantified as the mean beads eaten per cell. The fraction of phagocytic cells is as follows: 31/144 GFP-CAAX cells engulfed CD19 beads, 87/149 αCD19 CAR-P$^{Megf10}$ engulfed CD19 beads, 20/142 αCD22 CAR-P$^{Megf10}$ engulfed CD19 beads, 28/140 GFP-CAAX cells engulfed CD22 beads, 18/151 αCD19 CAR-P$^{Megf10}$ engulfed CD22 beads, 103/148 αCD22 CAR-P$^{Megf10}$ engulfed CD22 beads (pooled data was collected during three separate experiments). Error bars denote 95% confidence intervals and * indicates p<0.0001 compared to mCherry-CAAX control by Kruskal-Wallis test with Dunn's multiple comparison correction. FIG. 2B: J774A.1 macrophages expressing the αCD19 CAR-P$^{Megf10}$ were fed beads of various sizes (diameter of bead indicated below image). The beads were covered in a supported lipid bilayer ligated to His-tagged CD19 extracellular domain and the number of beads engulfed per cell is reported below each image. Dark gray bars (first bars from the left on X-axis) indicate CAR-P$^{Megf10}$ macrophages and light gray bars indicate CAR-P$^{GFP}$ (second bars from the left on X-axis). The αCD19 CAR-P$^{Megf10}$ macrophages were also incubated with 10 mm beads coated in phosphatidylserine (PS) and ICAM-1 (third bar in the middle graph, 51/390 cells engulfed a bead). The fraction of cells engulfing a CD19 bead is as follows: 135/169 CAR-P$^{Megf10}$ and 134/187 CAR-P$^{GFP}$ cells engulfed 2.5 um bead, 126/395 CAR-P$^{Megf10}$ and 112/499 CAR-P$^{GFP}$ cells engulfed a 5 μm bead, 48/377 CAR-P$^{Megf10}$ and 21/378 CAR-P$^{GFP}$ cells engulfed a 10 μm bead, 120/706 CAR-P$^{Megf10}$ and 45/675 CAR-P$^{GFP}$ cells engulfed a 15 μm bead, 194/760 CAR-P$^{Megf10}$ and 23/587 CAR-P$^{GFP}$ cells engulfed a 20 μm bead (data is pooled from at least three separate experiments). Error bars denote 95% confidence intervals of the mean. * indicates p<0.0001 respectively by Mann-Whitney test. All scale bars represent 5 μm.

FIG. 3A: Macrophages expressing αCD19 CAR-P$^{Megf10}$ (top) or αCD19 CAR-P$^{GFP}$ were incubated with CD19-ligated beads (position indicated with dotted line), fixed and stained for phosphotyrosine (magenta, top; greyscale, bottom). The fold enrichment of phosphotyrosine at the cell-bead synapse compared to the cell cortex is graphed on the right (n≥11; each dot represents one cell-bead synapse; lines represent the mean±one standard deviation). FIG. 3B: Schematic shows the structure of CAR-P constructs in the plot at right. An αCD19 (dark gray) scFv directs CAR specificity. The intracellular signaling domains from CD3ζ activate engulfment. On the right is a histogram depicting the fraction of macrophages engulfing the indicated number of CD19-coated beads. FIG. 3C: Comparison showing the average number of beads eaten per cell in J774A.1 macrophages expressing αCD19 CAR-Ps with the indicated intracellular signaling domain. 5 mm silica beads covered with a supported lipid bilayer containing His-tagged CD19 extracellular domain were used as an engulfment target (n=156-167 cells per condition collected during three separate experiments). Error bars denote 95% confidence intervals and *** indicates p<0.0001 compared to CAR-P$^{GFP}$ control by Kruskal-Wallis test with Dunn's multiple comparison in correction. FIG. 3D: Model of the liposome-based fluorescence quenching assay used to determine affinity between the Syk tSH2 domains and the receptor tails of CD3ζ and FcRγ, two intracellular signaling domains that promote engulfment. Binding between the Syk tSH2 reporter (Syk tSH2) and a receptor tail, gray was detected by rhodamine quenching of BG505 dye on the reporter (see Example 1 below). Kd was determined by assessing mean fluorescence quenching for the last 20 timepoints collected ~45 minutes after ATP addition over a receptor titration from 0 to 500 nM. Each point represents the mean±SD from three independent experiments. Kd ±SE was calculated by nonlinear fit assuming one site specific binding. FIG. 3E depicts a non-limiting example of the enrichment of F-actin at the cell-target synapse. Phalloidin staining (magenta overlayed with brightfield and DAPI, left; heatmap, right) of F-actin in a CAR-P$^{FcRγ}$ expressing macrophage shows a 2.3 fold enrichment at the cell-bead synapse (standard deviation of 1.2). The graph depicts actin enrichment at 30 cell-bead synapses collected on three separate days. Each dot represents a cell-bead synapse. The box plot indicates the interquartile range. The cell is in contact with a second bead, but this site of contact has not initiated cup formation and no actin enrichment.

FIG. 4A: J774A.1 macrophages expressing the αCD19 CAR-P$^{Megf10}$ (top panel, left; greyscale, center) engulf pieces of CD19+ Raji B cells (labeled with mCherry-CAAX; magenta in merge, left; greyscale, right). The corresponding control αCD19 CAR-P$^{Gn}$-infected cells are shown below. Arrows point to pieces of ingested Raji B cell. The proportion of CAR-P expressing macrophages internalizing one or more bite within 90 minutes is quantified on the right. Bites are defined as a fully internalized mCherry-positive vesicle >1 mm in diameter; n=46 CAR-P$^{Megf10}$ macrophages, n=39 CAR-P$^{FcRγ}$ macrophages and 102 CAR-P$^{GFP}$ macrophages acquired during three separate experiments. FIG. 4B: Time course of a J774A.1 macrophage expressing CAR-P$^{FcRγ}$ internalizing a whole Raji B cell labeled with mCherry-CAAX. FIG. 4C: Schematic shows the structure of CAR-P$^{tandem}$ construct, combining the intracellular signaling domain from FcRV and a p85-recruitment domain from CD19. FIG. 4D: Time course of a J774A.1 macrophage expressing CAR-P P$^{tandem}$ internalizing a whole Raji B cell labeled with mCherry-CAAX. FIG. 4E: Macrophages and Raji B cells were incubated together at a 1:2 macrophage:Raji ratio, and the number of whole Raji B cells eaten per 100 macrophages during 4-8 hours of imaging is graphed. Graph depicts pooled data from four independent experiments; n=921 CAR-P$^{GFP}$, n=762 CAR-P$^{FcRγ}$, n=638 CAR-PPI3K, n=555 CAR-P$^{tandem}$ cells. Sample sizes were selected for their ability to detect a 5% difference between samples with 95% confidence. FIG. 4F: 10,000 macrophages and 20,000 Raji B cells were incubated together for 44 hr. The number of Rajis was then quantified by FACS. 2-3 technical replicates were acquired each day on three separate days. The number of Rajis in each replicate was normalized to the average number present in the GFP-CAAX macrophage wells on that day. * indicates p<0.01, *** indicates p<0.0001 by two-tailed Fisher Exact Test (a and e) or by Ordinary one way ANOVA with Dunnet's correction for multiple comparisons (f); error bars denote 95% confidence intervals.

FIG. 8A: Schematic of antigen internalization and cross-presentation assay. CAR-P expressing BMDC cells were differentiated using GM-CS. CAR-P BMDC were incubated with Raji B cells expressing soluble ovalbumin (OVA). DC with OVA bites (internalized antigen) were then incubated with OTI T cells (OVA specific CD8+T cells) and OTI proliferation assessed as a measure of T cell stimulation. Results from each step of this assay are shown in sequence in FIGS. 8B-8D. FIG. 8B: Ovalbumin staining in Raji B cells infected with mCherry-CAAX-p2a-Ovalbumin lentivirus (OVA) and uninfected controls (uninfected) shows robust OVA expression in infected cells. At right the intracellular OVA signal is plotted as corrected total cell fluorescence (CTCF) for the ovalbumin channel. Each dot represents the CTCF of one cell; n=26 cells OVA, n=33 cells (uninfected); lines represent the mean±one standard deviation, and the graph is the pooled results of three biological replicates. The scale bar indicates 5 µm. FIG. 8C: Bone marrow-derived dendritic cells expressing the CAR-P$^{FcR\gamma}$ (top panel, left; greyscale, center) engulf pieces of CD19+ Raji B cells (labeled with mCherry-CAAX; magenta in merge, left; greyscale, right). The control αCD19 CAR-P$^{GFP}$-infected dendritic cells are shown below. Arrows point to pieces of ingested Raji B cell. The proportion of cells taking at least one bite after 90 minutes co-incubation is graphed on the right of images. Graphs show the pooled data of two separate experiments; n=28 CAR-P$^{FcR\gamma}$ dendritic cells and n=33 CAR-PGFP dendritic cells; * indicates p<0.0001 by two-tailed Fisher Exact Test; error bars denote 95% confidence intervals. Bites are defined as a fully internalized piece of mCherry-labeled material >1 µm in diameter. FIG. 8D**: OTI T cell proliferation after 72 hours incubation with CAR-P transduced CD11c+dendritic cells. ±RAJI below the x-axis indicates whether Raji-OVA B cells were added to CAR-P transduced dendritic cells prior to OTI addition. To measure proliferation, T cells were uniformly stained with eFluor670 dye on day 0, and proliferation was measured by dilution of the cell-bound dye. Graphs show the mean±SD of three independent biological replicates. Data points are values for individual wells of differentiated CD11c+dendritic cells. Boxed data indicate the mean % T cells dividing when dendritic cells were pulsed with SL8 (OVA) peptide, which directly binds to MEW without undergoing cross presentation. If dendritic cell differentiation was successful, the pulsed dendritic cells should be capable of inducing robust OTI proliferation. Sample sizes were selected to match previous studies that were able to detect robust T cell stimulation (Roberts et al., 2016).

DETAILED DESCRIPTION OF THE DISCLOSURE

Figure 1A:
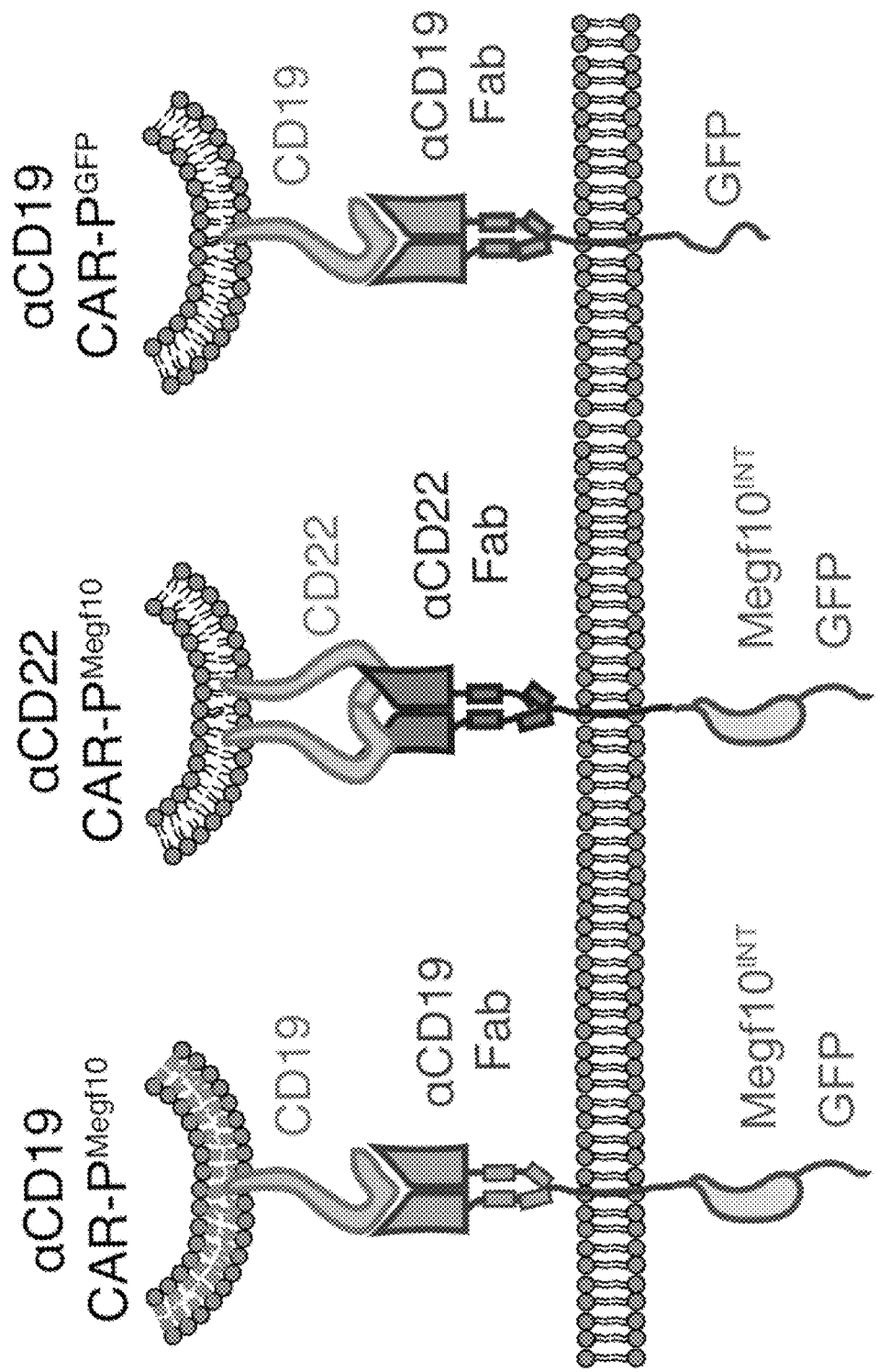
FIGS. 1A-1E summarize results from experiments performed to identify intracellular signaling region for CAR-P.

The present disclosure relates generally to the fields of cell biology and immunology. More particularly, provided herein is a new class of engineered chimeric antigen receptors (CARs) that specifically bind an engulfment receptor expressed on the surface of a phagocytic cell, activate the endogenous phagocytic signaling pathway, and thereby generate a modified phagocytic cell with targeted effector activity directed against a cell of interest such as, e.g., a cancer cell. By expressing a CAR disclosed herein in a phagocytic cell, the modified phagocytic cell is recruited to the tumor microenvironment where it acts as a potent immune effector by infiltrating the tumor and killing the target cells. This novel methodology, termed "Chimeric Antigen Receptors for Phagocytosis" (CAR-P), represents a new cellular therapeutic approach targeting cancerous cells. This is because the CAR-Ps disclosed herein represent the first synthetic receptors to engineer macrophage signaling pathways to direct the innate immune system to attack cancer. One aspect of the disclosure includes a modified phagocytic cell and pharmaceutical compositions including the modified phagocytic cell for adoptive cell therapy and treating a disease or condition associated with cancer.

Immune system constantly patrols human body, looking to eliminate cancerous cells and harmful microbes. It can spot these threats because it recognizes certain signals at the surface of dangerous cells. However, cancer cells often find ways to 'hide' from the immune system. Current cellular therapeutics are almost exclusively T cells. In contrast, macrophages are uniquely capable of enriching in the tumor microenvironment, where T cells are often excluded. Accordingly, a person skilled in the art will readily appreciate that this is a different and yet potentially synergistic approach with existing CAR-T therapy. In addition, the CAR-P phagocytes has potential advantages over CAR-T therapy in that CAR-Ps, and drug conjugates thereof, could present all possible cancer antigens from an individual, rather than restricting T cell killing to a single predefined antigen. Thus, by engineering macrophage signaling rather than T cell signaling, the killed artisan will be able to open new therapeutic avenues. One skilled in the art will also appreciate that CAR-Ps can be used for cross presentation using different cell types. As discussed in greater detail below, it is also contemplated that exosomes from CAR-P expressing cells can constitute an efficient means of antigen-presentation to T cells. As described below in some embodiments of the disclosure, the macrophages can be isolated from individuals, transfected with a CAR-P and introduced back into an individual to destroy cancer cells. As a proof of principle, over two days, a lymphoma cell line co-cultured with macrophages expressing the CAR-P exhibited a 40% decrease in cell number compared to the lymphoma cells cultured with un-edited macrophages. Thus, this receptor could serve as the foundation for a macrophage-based cellular therapeutic targeting leukemia and lymphoma.

Chimeric antigen receptors, or CARs, are receptors designed in a laboratory to attach to specific proteins that are found on a cancer cell. These receptors tell immune cells, such as T cells, to attack cancers. T cells that carry CARs are already used to treat people with blood cancers. Yet, these immune cells are not good at penetrating a solid tumor to kill the cells inside, which limits their use.

CARs can be synthetic transmembrane receptors that redirect T cell activity towards clinically relevant targets (reviewed in [Lim et al., 2017; Fesnak et al., 2016]). The CAR-T receptor contains an extracellular single chain antibody fragment (scFv) that recognizes known tumor antigens, and intracellular signaling domains from the T Cell Receptor (TCR) and costimulatory molecules that trigger T cell activation (Fesnak et al., 2016; Kochenderfer et al., 2009). CAR-T cells recognizing CD19, a marker expressed at high levels on the surface of B cells and B cell-derived malignancies, have been used successfully to target hematological malignancies with 70-90% of individuals showing measurable improvement (Lim et al., 2017; Engel et al., 1995; Haso et al., 2013). The success of CAR-T suggests that programming immune cells to target cancer might be a broadly applicable approach.

In some embodiments, a CAR-P DNA vector or mRNA could be delivered to endogenous phagocytic cells (macrophages or dendritic cells). As described in further detail below, there are no specific limitations with respect to the procedures and techniques that can be suitably employed for delivery of the CAR-P DNA vector or mRNA into the target phagocytic cell. Non-limiting delivery procedures suitable for the methods disclosed herein include stable or transient transfection, lipofection, electroporation, microinjection, liposomes, iontophoresis, and infection with recombinant viral vectors. In some embodiments, the CAR-P DNA vector or mRNA could be delivered to endogenous phagocytic cells by using one or more viral, particle, liposome, or exosome-based strategies. Such a strategy would target phagocytic cells towards cancer cells.

Macrophages and dendritic cells are also antigen-presenting cells. Therefore, without being bound any particular theory, it is also contemplated that, in various embodiments of the disclosure, by targeting phagocytic cells towards cancer cells in one of the two strategies above, it is possible that these antigen-presenting cells could internalize and cross-present antigens to T cells, which would engage in cytotoxic killing of cancer cells.

As described above, CARs can be synthetic receptors that reprogram T cells to kill cancer. The success of CAR-T cell therapies highlights the promise of programmed immunity and suggests that applying CAR strategies to other immune cell lineages may be beneficial. In some embodiments, t provided is a family of engineered CARs for phagocytosis (CAR-Ps) that direct macrophages to engulf specific targets, including cancer cells. In some embodiments, the CAR-Ps of the disclosure include an extracellular antibody fragment, which can be modified to direct CAR-P activity towards specific antigens. As described in greater detail below, by screening a panel of engulfment receptor intracellular domains, it was found that the cytosolic domains from Megf10 and FcRγ robustly triggered engulfment independently of their native extracellular domain. It was further found that CAR-Ps drive specific engulfment of antigen-coated synthetic particles and whole human cancer cells. Furthermore, addition of a tandem PI3K recruitment domain increased cancer cell engulfment. Finally, it was also found that CAR-P expressing murine macrophages reduce cancer cell number in co-culture by over 40%.

In some embodiments, the present disclosure describes the design and construction of a family of engineered CAR-Ps, and their respective expression in modified macrophages. These modified macrophages were found to be able to recognize and attack beads covered in proteins found on cancer cells. The modified macrophages were shown to also limit the growth of live cancer cells in a dish by 'biting' and even 'eating' them. Since these results are promising in the laboratory, it is also contemplated, in various embodiments, determining whether these reprogrammed macrophages can recognize and fight cancers in living animals. The disclosure also provides compositions and methods useful for producing such CARs, as well as methods for the treatment of health disorders associated with cancer, including solid tumor and hematologic malignancy.

In some particular embodiments, the disclosure describes engineered CAR-Ps that are capable of promoting engulfment of B cell derived cancer cells and cancer antigen-coated particles. In some embodiments, the CAR-P disclosed herein includes an antibody fragment directed against CD19 (e.g., amino acid residues 23-130 Genbank AMZ04819) or CD22 (e.g., amino acid residues 22-258 of translated Genbank AMZ04819) fused to the intracellular domain of either mouse Megf10 (e.g., amino acid residues 879-1147 of Uniprot Q6DIB5) or FcRγ (e.g., amino acid residues 19-86 of Uniprot P20491). In some embodiments, targeting of the CAR-P disclosed herein to the plasma membrane was achieved by addition of the CD8 signal peptide (e.g., amino acid residues 1-21 of Uniprot Q96QR6_HUMAN) to the N terminus and insertion of the CD8 stalk and transmembrane domains (e.g., amino acid residues 138-206 Uniprot Q96QR6_Human) between the antibody fragment and cytosolic signaling domain. In some embodiments, the cytosolic domains of Megf10 and FcRγ, when fused to the indicated antibody fragments, robustly triggered engulfment of antigen-coated particles, "bites" of cancer cells, and whole cancer cells. In some embodiments, addition of a PI3K recruitment domain (amino acids 500-534 mouse CD19 (Uniprot CD19_MOUSE) to the FcRγ intracellular domain increased engulfment of whole cancer cells. Remarkably, as evidence of therapeutic potential, CAR-P expressing macrophages reduce cancer cell number in co-culture by over 40%. Taken together, these results demonstrate that the CAR-Ps of the disclosure can robustly trigger the phagocytosis of cancer cell material, whole cancer cells, and cancer antigen-coated synthetic particles.

Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, comprising mixtures thereof "A and/or B" is used herein to include all of the following alternatives: "A", "B", "A or B", and "A and B".

The term "about", as used herein, has its ordinary meaning of approximately. As such, the term "about" is used to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The term "operably linked", as used herein, denotes a physical or functional linkage between two or more elements, e.g., polypeptide sequences or polynucleotide sequences, which permits them to operate in their intended fashion. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous. In addition, in the context of a polypeptide, "operably linked" refers to a physical linkage (e.g., directly or indirectly linked) between amino acid sequences (e.g., different segments, regions, or domains) to provide for a described activity of the polypeptide. In the present disclosure, various segments, regions, or domains of the chimeric polypeptides of the disclosure may be operably linked to retain proper folding, processing, targeting, expression, binding, and other functional properties of the chimeric polypeptides in the cell. Unless stated otherwise, various regions, domains, and segments of the chimeric polypeptides of the disclosure are operably linked to each other. Operably linked regions, domains, and segments of the chimeric polypeptides of the disclosure may be contiguous or non-contiguous (e.g., linked to one another through a linker).

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule can be one which: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

As used herein, a "subject" or an "individual" includes animals, such as human (e.g., human subjects) and non-human animals. In some embodiments, a "subject" or "individual" is a patient under the care of a physician. Thus, the subject can be a human patient or an individual who has, is at risk of having, or is suspected of having a disease of interest (e.g., cancer) and/or one or more symptoms of the disease. The subject can also be an individual who is diagnosed with a risk of the condition of interest at the time of diagnosis or later. The term "non-human animals" includes all vertebrates, e.g., mammals, e.g., rodents, e.g., mice, and non-mammals, such as non-human primates, e.g., sheep, dogs, cows, chickens, amphibians, reptiles, etc.

The term "vector" is used herein to refer to a nucleic acid molecule or sequence capable of transferring or transporting another nucleic acid molecule. The transferred nucleic acid molecule is generally linked to, e.g., inserted into, the vector nucleic acid molecule. Generally, a vector is capable of replication when associated with the proper control elements. The term "vector" includes cloning vectors and expression vectors, as well as viral vectors and integrating vectors. An "expression vector" is a vector that includes a regulatory region, thereby capable of expressing DNA sequences and fragments in vitro and/or in vivo. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses. In some embodiments, a vector is a gene delivery vector. In some embodiments, a vector is used as a gene delivery vehicle to transfer a gene into a cell.

It is understood that aspects and embodiments of the disclosure described herein include "comprising," "consisting," and "consisting essentially of" aspects and embodiments.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Headings, e.g., (a), (b), (i) etc., are presented merely for ease of reading the specification and claims. The use of headings in the specification or claims does not require the steps or elements be performed in alphabetical or numerical order or the order in which they are presented.

Phagocytosis and Phagocytes

Phagocytosis generally refers to an engulfment process of cells or large particles (>0.5 µm) wherein tethering of a target cell or particle, engulfment of the target cell or particle, and degradation of the internalized target cell or particle occurs. In certain embodiments, phagocytosis includes formation of a phagosome that encompasses the internalized target cell or particle and phagosome fusion with a lysosome to form a phagolysosome, wherein the contents therein are degraded. As such, "phagocytosis"

includes the process of "efferocytosis", which specifically refers to the phagocytosis of apoptotic or necrotic cells in a non-inflammatory manner.

There are two principle types of phagocytosis, which are influenced by the target, cell-type and surrounding milieu. Anti-microbe phagocytosis clears and degrades disease-causing microbes, induces pro-inflammatory signaling through cytokine and chemokine secretion, and recruits immune cells to mount an effective inflammatory response. This type of phagocytosis is often referred to as "inflammatory phagocytosis" (or "immunogenic phagocytosis"). However, in some instances, such as with certain persistent infections, anti-inflammatory responses may follow microbial uptake. Anti-microbe phagocytosis is commonly performed by professional phagocytes of the myeloid lineage, such as immature dendritic cells (DCs) and macrophages and by tissue-resident immune cells.

Phagocytosis of damaged, self-derived apoptotic cells or cell debris (e.g., efferocytosis), in contrast, is typically a non-inflammatory (also referred to as a "non-immunogenic") process. Billions of damaged, dying, and unwanted cells undergo apoptosis each day. Unwanted cells include, for example, excess cells generated during development, senescent cells, infected cells (intracellular bacteria or viruses), transformed or malignant cells, and cells irreversibly damaged by cytotoxic agents. Phagocytes execute specific, swift removal of apoptotic cells without causing damage to the surrounding tissues or inducing a pro-inflammatory immune response. Steps for apoptotic cell clearance include: (1) release of "find me" signals from apoptotic cells to recruit phagocytes to the location of apoptotic cells; (2) "eat me" signals exposed on the surface of apoptotic cells are bound by phagocytes via specific receptors; (3) cytoskeletal rearrangement to engulf the apoptotic cell; and (4) the ingested apoptotic cell is digested and specific phagocytic responses are elicited (e.g., secretion of anti-inflammatory cytokines).

The terms "phagocytic cells" and "phagocytes" are used interchangeably herein to refer to a cell that is capable of phagocytosis, e.g., ingesting microorganisms and foreign particles, for example, capable of engulfing a large particulate mass, for example from about 0.1 μm in diameter up to about 2 mm or about 1 mm in diameter; from about 0.5 μm in diameter to about 1 mm in diameter, etc., particularly including up to the size of a microbial cell or mammalian cell, e.g. a tumor cell. Phagocytosis, as described above, encompasses the engulfment of cells, pathogens, and various particles by surrounding it with the effector cell membrane. As such, phagocytes protect the body by ingesting harmful foreign particles, bacteria, and dead or dying cells. These cells are essential for fighting infections and for subsequent immunity.

There are several categories of phagocytes. Exemplary phagocytes include macrophages, mononuclear cells (histiocytes and monocytes), polymorph nuclear leukocytes, (neutrophils) and dendritic cells. Phagocytes of humans and other jawed vertebrates are divided into "professional" and "non-professional" groups based on the efficiency with which they participate in phagocytosis. The professional phagocytes include many types of white blood cells (such as neutrophils, monocytes, macrophages, mast cells, and dendritic cells). The main difference between professional and non-professional phagocytes is that the professional phagocytes have molecules called receptors on their surfaces that can detect harmful objects, such as bacteria, that are not normally found in the body. As such, professional phagocytes are capable of recognizing a wide variety of phagocytic targets, and of ingesting them at a higher rate than non-phagocytic cells.

Dendritic cell (DC) refers to any member of a diverse population of morphologically similar cell types found in lymphoid or non-lymphoid tissues. DCs are referred to as "professional" antigen presenting cells, and have a high capacity for sensitizing MHC-restricted T cells. DCs may be recognized by function, by phenotype and/or by gene expression pattern, particularly by cell surface phenotype. These cells are characterized by their distinctive morphology, high levels of surface MHC-class II expression and ability to present antigen to CD4+ and/or CD8+ T cells, particularly to naive T cells.

Neutrophils and macrophages are representative of fully differentiated phagocytes. While neutrophils leaving the bone marrow are fully differentiated, macrophages differentiate from circulating monocytes in extra-vascular tissues. Monocytes display a lower phagocytic response, compared to neutrophils and macrophages, and must respond to activation and differentiation signals in order to achieve optimal phagocytic capacity. The process of monocyte-to-macrophage differentiation has been well characterized, and can be performed in vitro or in vivo.

Macrophages are of particular interest. These immune cells can make their way inside tumors and travel to cancers that the rest of the immune system cannot reach. Macrophages are critical effectors of the innate immune system, responsible for engulfing debris and pathogens. Accumulating evidence suggests that macrophages are abundant in the tumor microenvironment of numerous cancers where they can adopt a classically activated (Ml, antitumor) or an alternatively activated (M2, pro-tumor) phenotype. Macrophages are potent effectors of the innate immune system and are capable of at least three distinct anti-tumor functions: phagocytosis, cellular cytotoxicity, and antigen presentation to orchestrate an adaptive immune response. While T cells require antigen-dependent activation via the T cell receptor or the chimeric immunoreceptor, macrophages can be activated in a variety of ways. Direct macrophage activation is antigen-independent, relying on mechanisms such as pathogen associated molecular pattern recognition by Toll-like receptors (TLRs). Therefore, harnessing macrophages to combat tumor growth is of longstanding interest (Alvey and Discher, 2017; Lee et al., 2016). Macrophages are uniquely capable of penetrating solid tumors, while other immune cells, like T cells, are physically excluded or inactivated (Lim et al., 2017; Lee et al., 2016). This suggests that engineered macrophages may augment existing T cell-based therapies. Early efforts transferring healthy macrophages into cancer patients failed to inhibit tumor growth, suggesting that macrophages require additional signals to direct their activity towards tumors (Lacerna et al., 1988; Andreesen et al., 1990). Antibody blockade of CD47, a negative regulator of phagocytosis, reduced tumor burden, indicating that shifting the balance in favor of macrophage activation and engulfment is a promising therapeutic avenue (Majeti et al., 2009; Chao et al., 2010; Jaiswal et al., 2009; Tseng et al., 2013).

Compositions of the Disclosure

Chimeric Polypeptides and Chimeric Antigen Receptors

In one aspect, some embodiments of the disclosure relate to novel chimeric polypeptides which includes (a) an extracellular domain including an antigen-binding region specific for one or more cancer-associated antigen; (b) a transmembrane domain; (c) at least one copy of an intracellular signaling domain from an engulfment receptor; and (d) at least one copy of a recruitment domain. In some aspects and embodiments of the disclosure, the chimeric polypeptides described herein are chimeric antigen receptors. The terms "binding region," "binding domain," and "binding moiety" as used herein refer to a molecule, such as a peptide, oligopeptide, polypeptide, or protein that possesses the ability to specifically and non-covalently bind, associate, unite, recognize, or combine with a target molecule, such as a cancer-associated antigen (e.g., CD22, CD19, CD138, CD38, CD33, CD123, CD79b, Mesothelin, PSMA, BCMA, ROR1, MUC-16, CD22, CD19, EGFRvIII, VEGFR-2, or GD2). A binding domain includes any naturally occurring, synthetic, semi-synthetic, or recombinantly produced binding partner for a biological molecule or other target of interest. In some embodiments, the binding region is an antigen-binding region, such as an antibody or functional binding domain or antigen-binding portion thereof. The antigen-binding region can include any domain that binds to the antigen and may include, but is not limited to, a monoclonal antibody, a polyclonal antibody, a synthetic antibody, a human antibody, a humanized antibody, a non-human antibody, and any fragment thereof. Thus, in some embodiments, the antigen binding domain portion includes a mammalian antibody or a fragment thereof. Non-limiting examples of antigen-binding regions suitable for the chimeric polypeptides of this disclosure include an antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof.

In some embodiments, the antigen-binding region is derived from the same cell type or the same species in which the chimeric polypeptide will ultimately be used in. For example, for use in humans, it the antigen-binding region of the chimeric polypeptide includes a human antibody, a humanized antibody, or a fragment thereof.

As used herein, the term "chimeric" polypeptide refers to a polypeptide including at least two amino acid sequences, e.g., polypeptide domains, that are is not naturally linked in nature. The amino acid sequences may normally exist in separate proteins that are brought together in the chimeric polypeptide or they may normally exist in the same protein but are placed in a new arrangement in the chimeric polypeptide. A chimeric polypeptide may be created, for example, by chemical synthesis, or by creating and translating a polynucleotide in which the peptide regions are encoded in the desired relationship.

An "engulfment signaling domain" of an engulfment receptor refers to an intracellular effector domain, which, upon binding of the target molecule (e.g., an cancer-associated antigen) targeted by the extracellular domain of the chimeric polypeptide expressed by a host cell, activates one or more signaling pathways in the host cell resulting in engulfment, including, in specific embodiments, cytoskeletal rearrangement of the host cell and internalization of the target cell, microbe, or particle associated with the antigen. In some embodiments, an engulfment signaling domain activates one or more signaling pathways resulting in phagocytosis of the target cell, microbe, or particle. In some embodiments, the engulfment signaling domain includes a primary engulfment signaling domain. In certain other embodiments, the engulfment signaling domain includes a primary engulfment signaling domain and a secondary engulfment signaling domain.

As described above, the chimeric polypeptides of the disclosure include at least one copy of a recruitment domain. The recruitment domain generally includes an intracellular polypeptide sequence capable of mediating protein-protein interaction with one or more cellular proteins, thereby can bind to and recruit such cellular proteins. A skilled artisan in the art will appreciate that the interaction and/or binding between a recruitment domain and a cellular protein can be direct or indirect interaction and/or binding. In some embodiments, the recruitment domain of the chimeric polypeptides disclosed herein directly binds to one or more cellular proteins. In some embodiments, the one or more cellular proteins to which the recruitment domain binds to (e.g., recruited) include components of the phagocytic signaling pathway. In some embodiments, the binding of the recruitment domain to one or more phagocytic signaling components activates the endogenous phagocytic signaling pathway and/or enhances the activity of the chimeric receptor. In some embodiments, the recruitment domain binds to a cellular protein confers an increase in engulfment of the target cell, microbe, or particle associated with the antigen.

In some embodiments, the recruitment domain of the chimeric polypeptides disclosed herein includes a polypeptide sequences that is capable of interacting with, e.g., binding to the p85 regulatory subunit of phosphoinositide 3-kinase (PI3K). Generally, any polypeptide sequence capable of binding to p85 can be suitably used in a recruitment domain of the chimeric polypeptides disclosed herein. Examples of recruitment domains suitable for the compositions and methods disclosed herein include, but are not limited to, p85-binding domains derived from CD19, Gab2, IREM-1, and PDGF receptor. Additional examples of suitable recruitment domains for the compositions and methods disclosed herein include p85-binding domains derived from CSFR-1, c-Kit, ErbB3, and CD7. In some embodiments, the recruitment domain of the chimeric polypeptides of the disclosure includes a p85-recruitment domain from CD19.

In some embodiments, the recruitment domain of the chimeric polypeptides disclosed herein includes a polypeptide sequences that is capable of interacting, e.g., binding to a cytosolic signaling protein. Generally, any polypeptide sequence capable of binding to a cytosolic signaling protein can be suitably used in a recruitment domain of the chimeric polypeptides disclosed herein. Suitable examples of recruitment domains for the compositions and methods disclosed herein include, but are not limited to, SRC homology 3 domains (e.g., SH3 domains). SH3 domain is generally described as a conserved sequence in the viral adaptor protein v-Crk. This domain is also present in the molecules of phospholipase and several cytoplasmic tyrosine kinases such as Abl and Src. SH3 has also been identified in several other protein families such as: PI3 Kinase, Ras GTPase-activating protein, CDC24 and CDC25. SH3 domains are found in proteins of signaling pathways regulating the cytoskeleton, the Ras protein, and the Src kinase and many others. Some SH3 proteins interact with adaptor proteins and tyrosine kinases. Approximately 300 SH3 domains are found in proteins encoded in the human genome. SH3 domain is also believed to be responsible for controlling protein-protein interactions in the signal transduction pathways and regulating the interactions of proteins involved in the cytoplasmic signaling. In some embodiments, suitable examples of SH3 domains for the compositions and methods disclosed herein include, but are not limited to, SH3 domains derived from C3G, p41, PEP, p47, HPK1, SLP-1, and CD3c. In some embodiments, additional exemplary SH3 domains suitable for the compositions and methods disclosed herein include SH3 domains derived from PAK, AIP4, and Sos.

In some embodiments, the recruitment domain of the chimeric polypeptides disclosed herein includes a proline-rich peptide sequence capable of interacting with (e.g., binding to) a SH3 domain-containing protein. The term proline-rich peptide is generally used to describe peptides containing a high proportion of proline and hydrophobic amino acids, and generally has a high affinity binding to SH3 domain-containing proteins. In principle, any proline-rich polypeptide sequence capable of interacting with, e.g., binding to a SH3 domain-containing protein can be suitably included in a recruitment domain of the chimeric polypeptides disclosed herein. In some embodiments, the proline-rich peptide has 5% or more of proline in its sequence. In some embodiments, the proline-rich peptide has at least 5%, at least 10%, at least 20%, at least 30%, at least 40%, at least 50%, at least 60%, at least 70%, at least 80%, at least 90%, or at least 95% proline in its sequence. Suitable examples of proline-rich polypeptide sequences for the compositions and methods disclosed herein include, but are not limited to, proline-rich polypeptide sequences derived from C3G, p41, PEP, p4'7, HPK1, SLP-1, and CD3c. In some embodiments, additional exemplary proline-rich polypeptide sequences suitable for the compositions and methods disclosed herein proline-rich polypeptide sequences derived from PAK, AIP4, and Sos.

In some embodiments, a chimeric polypeptides disclosed herein includes at least one copy of a recruitment domain selected from the group consisting of: (a) p85-binding domains derived from CD19, Gab2, IREM-1, PDGF receptor, CSFR-1, c-Kit, ErbB3, and CD7 to recruit the p85 regulatory subunit of phosphoinositide 3-kinase (PI3K); (b) SH3 domains derived from Crk, Cdc25, Phospholipase, Ras, Vav, GRB2, FAK, Pyk2, TRIP10, and Gads to recruit cytosolic signaling proteins; and (c) proline-rich peptides from C3G, p41, PEP, p47, HPK1, SLP-1, CD3c, PAK, AIP4, or Sos to recruit SH3 domain-containing proteins. In some embodiments, the at least one copy of a recruitment domain includes: (a) a p85-binding domain derived from CD19, Gab2, IREM-1, PDGF receptor, CSFR-1, c-Kit, ErbB3, or CD7 to recruit the p85 regulatory subunit of phosphoinositide 3-kinase (PI3K); (b) an SH3 domain derived from Crk, Cdc25, Phospholipase, Ras, Vav, GRB2, FAK, Pyk2, TRIP10, or Gads to recruit cytosolic signaling proteins; and/or (c) a proline-rich peptide from C3G, p41, PEP, p4'7, HPK1, SLP-1, CD3c, PAK, AIP4, or Sos to recruit SH3 domain-containing proteins.

The binding activity of the chimeric polypeptides of the disclosure to their target antigens can be assayed by any suitable method known in the art. For example, a variety of assays are known for identifying and/or characterizing binding domains of the present disclosure that specifically bind a particular target antigen, as well as determining binding domain affinities, such as Western blot, ELISA, and BIA-CORE® analysis. An antibody or polypeptide that "preferentially binds" or "specifically binds" (used interchangeably herein) to a target protein or target epitope is a term well understood in the art, and methods to determine such specific or preferential binding are also known in the art. An antibody or polypeptide is said to exhibit "specific binding" or "preferential binding" if it reacts or associates more frequently, more rapidly, with greater duration and/or with greater affinity with a particular protein or epitope than it does with alternative proteins or epitopes. An antibody or polypeptide "specifically binds" or "preferentially binds" to a target if it binds with greater affinity, avidity, more readily, and/or with greater duration than it binds to other substances. Also, an antibody or polypeptide "specifically binds" or "preferentially binds" to a target if it binds with greater affinity, avidity, more readily, and/or with greater duration to that target in a sample than it binds to other substances present in the sample. For example, an antibody or polypeptide that specifically or preferentially binds to a CD19 epitope is an antibody or polypeptide that binds this epitope with greater affinity, avidity, more readily, and/or with greater duration than it binds to other CD19 epitopes or non-CD19 epitopes. It is also understood by reading this definition, for example, that an antibody or polypeptide (or moiety or epitope) which specifically or preferentially binds to a first target may or may not specifically or preferentially bind to a second target. As such, "specific binding" or "preferential binding" does not necessarily require (although it can include) exclusive binding.

In some embodiments, the chimeric polypeptide of the disclosure further includes one or more linkers/spacers. For example, between the antigen binding domain and the transmembrane domain of the chimeric polypeptide, or between the intracellular domain and the transmembrane domain of the chimeric polypeptide, one or more linkers/spacers may be incorporated. There is no particular limitation with respect to the linkers that can be used in the chimeric polypeptides described herein. In some embodiments, the linker includes a peptide linker/spacer sequence. In some embodiments, the linker is a synthetic compound linker such as, for example, a chemical cross-linking agent. Non-limiting examples of suitable cross-linking agents that are available on the market include N-hydroxysuccinimide (NETS), disuccinimidylsuberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidylsuccinate) (EGS), ethyleneglycol bis(sulfosuccinimidyl)uccinate) (sulfo-EGS), disuccinimidyl tartrate (DST), di sulfosuccinimidyl tartrate (sulfo-DST), bis[2-(succinimidooxycarbonyloxy)ethyl] sulfone (BSOCOES), and bis[2-(sulfosuccinimidooxycarbonyloxy)ethyl]sulfone (sulfo-BSOCOES).

In some embodiments, the linker includes a peptide linker sequence. In principle, there are no particular limitations to the length and/or amino acid composition of the linker peptide sequence. In some embodiments, any arbitrary single-chain peptide including about one to 100 amino acid residues (e.g., 2, 3, 4, 5, 6, 7, 8, 9, 10, 11, 12, 13, 14, 15, 16, 17, 18, 19, 20, etc. amino acid residues) can be used as a peptide linker. In some embodiments, the linker peptide sequence includes about 5 to 50, about 10 to 60, about 20 to 70, about 30 to 80, about 40 to 90, about 50 to 100, about 60 to 80, about 70 to 100, about 30 to 60, about 20 to 80, about 30 to 90 amino acid residues. In some embodiments, the linker peptide sequence includes about 1 to 10, about 5 to 15, about 10 to 20, about 15 to 25, about 20 to 40, about 30 to 50, about 40 to 60, about 50 to 70 amino acid residues. In some embodiments, the linker peptide sequence includes about 40 to 70, about 50 to 80, about 60 to 80, about 70 to 90, or about 80 to 100 amino acid residues. In some embodiments, the linker peptide sequence includes about 1 to 10, about 5 to 15, about 10 to 20, about 15 to 25 amino acid residues. In some embodiments, the linker peptide sequence may include up to 300 amino acids, preferably 10 to 100 amino acids and most preferably 25 to 50 amino acids. In some embodiments, a short oligo- or polypeptide linker, preferably between 2 and 10 amino acids in length may form the linkage between the transmembrane domain and the intracellular domain of the chimeric polypeptide of the disclosure.

In some embodiments, the length and amino acid composition of the linker peptide sequence can be optimized to vary the orientation and/or proximity of the polypeptide domains to one another to achieve a desired activity of the chimeric polypeptide. In some embodiments, the orientation and/or proximity of the polypeptide domains to one another can be varied as a "tuning" tool to achieve a tuning effect that would enhance or reduce the biological activity of the chimeric polypeptide. In some embodiments, the orientation and/or proximity of the polypeptide domains to one another can be optimized to create a partial to full phagocytic versions of the chimeric polypeptide. In certain embodiments, the linker contains only glycine and/or serine residues (e.g., glycine-serine linker). Examples of such peptide linkers include: Gly, Ser; Gly Ser; Gly Gly Ser; Ser Gly Gly; Gly Gly Gly Ser (SEQ ID NO: 19); Ser Gly Gly Gly (SEQ ID NO: 20); Gly Gly Gly Gly Ser (SEQ ID NO: 21); Ser Gly Gly Gly Gly (SEQ ID NO: 22); Gly Gly Gly Gly Gly Ser (SEQ ID NO: 23); Ser Gly Gly Gly Gly Gly (SEQ ID NO: 24); Gly Gly Gly Gly Gly Gly Ser (SEQ ID NO: 25); Ser Gly Gly Gly Gly Gly Gly (SEQ ID NO: 26); (Gly Gly Gly Gly Ser)n (SEQ ID NO: 27), wherein n is an integer of one or more; and (Ser Gly Gly Gly Gly)n (SEQ ID NO: 28), wherein n is an integer of one or more. In some embodiments, the linker peptides are modified such that the amino acid sequence GSG (that occurs at the junction of traditional Gly/Ser linker peptide repeats) is not present. For example, in some embodiments, the peptide linker includes an amino acid sequence selected from the group consisting of: (GGGXX)nGGGGS (SEQ ID NO: 29) and GGGGS (XGGGS)n (SEQ ID NO: 30), where X is any amino acid that can be inserted into the sequence and not result in a polypeptide including the sequence GSG, and n is 0 to 4. In some embodiments, the sequence of a linker peptide is (GGGX1X2)nGGGGS (SEQ ID NO: 31) and X1 is P and X2 is S and n is 0 to 4. In some other embodiments, the sequence of a linker peptide is (GGX1X2)nGGGGS (SEQ ID NO: 32) and X1 is G and X2 is Q and n is 0 to 4. In some other embodiments, the sequence of a linker peptide is (GGGX1X2)nGGGGS (SEQ ID NO: 33) and X1 is G and X2 is A and n is 0 to 4. In yet some other embodiments, the sequence of a linker peptide is GGGGS(XGGGS)n (SEQ ID NO: 34), and X is P and n is 0 to 4. In some embodiments, a linker peptide of the disclosure comprises or consists of the amino acid sequence (GGGGA)$_2$GGGGS (SEQ ID NO: 35). In some embodiments, a linker peptide comprises or consists of the amino acid sequence (GGGGQ)$_2$GGGGS (SEQ ID NO: 36). In another embodiment, a linker peptide comprises or consists of the amino acid sequence (GGGPS)$_2$GGGGS (SEQ ID NO: 37) In another embodiment, a linker peptide comprises or consists of the amino acid sequence GGGGS (PGGGS)$_2$ (SEQ ID NO: 38). In yet a further embodiment, a linker peptide comprises or consists of the amino acid sequence GSGGS (SEQ ID NO: 39) or SGGSGS (SEQ ID NO: 40).

In some embodiments, the extracellular domain of the chimeric polypeptide includes an antigen-binding region that binds to one or more target antigens of interest. In some embodiments, the antigen-binding region binds to one or more target antigens expressed on the surface of a target cell (e.g., cell surface markers). Examples of cell surface markers that can act as an antigen that binds to the antigen binding domain of the chimeric polypeptide include those associated with viral, bacterial and parasitic infections, autoimmune disease, and cancer cells. In some embodiments, the antigen-binding region binds to a cancer-associated antigen, e.g., tumor antigen, such as an antigen that is specific for a tumor or cancer of interest. Accordingly, in some embodiments, the extracellular domain of the chimeric polypeptide includes an antigen-binding region that binds to one or more specific for one or more cancer-associated antigen. Generally, the cancer-associated antigen can be any cancer-associated antigen. Suitable cancer-associated antigens include, but are not limited to, CD19, CD22, HER2 (ERBB2/neu), Mesothelin, PSCA, CD123, CD30, CD171, CD138, CS-1, CLECL1, CD33, CD79b, EGFRvIII, GD2, GD3, BCMA, PSMA, ROR1, FLT3, TAG72, CD38, CD44v6, CEA, EPCAM, B7H3 (CD276), KIT (CD 117), CD213A2, IL-1 IRa, PRSS21, VEGFR2, CD24, MUC-16, PDGFR-beta, SSEA-4, CD20, MUC1, EGFR, NCAM, Prostase, PAP, ELF2M, Ephrin B2, FAP, EphA2, GM3, TEM1/CD248, TEM7R, CLDN6, TSHR, GPRC5D, CD97, CD179a, ALK, and IGLL1. In some embodiments, the one or more cancer-associated antigens is selected from the group consisting of CD19 and CD22.

In some embodiments, the antigen-binding region includes one or more antigen-binding determinants (e.g., epitopes) of an antibody or a functional antigen-binding fragment thereof. In some embodiments, the cancer-associated antigen of the present disclosure includes one or more antigenic cancer epitopes. The antigen-binding region can include naturally-occurring polypeptides or can be engineered, designed, or modified so as to provide desired and/or improved properties.

The term "antigen-binding fragment" as used herein refers to an antibody fragment such as, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody including one or more CDRs. Blocking antibodies and non-blocking antibodies are both suitable. As used herein, the term "blocking" antibody or an "antagonist" antibody refers to an antibody that prevents, inhibits, blocks, or reduces biological or functional activity of the antigen to which it binds. Blocking antibodies or antagonist antibodies can substantially or completely prevent, inhibit, block, or reduce the biological activity or function of the antigen. For example, a blocking anti-CD19 antibody can prevent, inhibit, block, or reduce the binding interaction between CD19 and its natural ligand (e.g., CD77), thus preventing, blocking, inhibiting, or reducing the immunosuppressive functions associated with the CD19/CD77 interaction. The term "non-blocking" antibody refers to an antibody that does not interfere, inhibits, blocks, or reduces biological or functional activity of the antigen to which it binds.

Accordingly, in some embodiments, the antigen-binding region of the extracellular domain includes an amino acid sequence for an antibody selected from the group consisting of antigen-binding fragments (Fab), single-chain variable fragments (scFv), nanobodies, VH domains, VL domains, single domain antibodies (dAb), VNAR domains, and VHH domains, bispecific antibodies, diabodies, or a functional fragment of any one of the foregoing. In some embodiments, the antigen-binding region includes a heavy chain variable region and a light chain variable region.

In some embodiments, the heavy chain variable region and the light chain variable region of the antigen-binding region are operably linked to each other via one or more intervening amino acid residues that are positioned between the heavy chain variable region and the light chain variable region. In some embodiments, the one or more intervening amino acid residues include a linker peptide sequence. In principle, there are no particular limitations to the length and/or amino acid composition of the linker peptide sequence. In some embodiments, any arbitrary single-chain peptide including about one to 100 amino acid residues (e.g., 2, 3, 4, 5, 6, 7, 8, 9, 10, 11, 12, 13, 14, 15, 16, 17, 18, 19, 20, etc. amino acid residues) can be used as a peptide linker. In some embodiments, the linker peptide sequence includes about 5 to 50, about 10 to 60, about 20 to 70, about 30 to 80, about 40 to 90, about 50 to 100, about 60 to 80, about 70 to 100, about 30 to 60, about 20 to 80, about 30 to 90 amino acid residues. In some embodiments, the linker peptide sequence includes about 1 to 10, about 5 to 15, about 10 to 20, about 15 to 25, about 20 to 40, about 30 to 50, about 40 to 60, about 50 to 70 amino acid residues. In some embodiments, the linker peptide sequence includes about 40 to 70, about 50 to 80, about 60 to 80, about 70 to 90, or about 80 to 100 amino acid residues. In some embodiments, the linker peptide sequence includes about 1 to 10, about 5 to 15, about 10 to 20, about 15 to 25 amino acid residues.

In some embodiments of the disclosure, the intracellular signaling domain of the engulfment receptor includes at least 1, at least 2, at least 3, at least 4, or at least 5 immunoreceptor tyrosine-based activation motifs (ITAMs). Generally, any intracellular signaling domain including an ITAM can be suitably used for the construction of the chimeric polypeptides as described herein. An "ITAM," as used herein, is a conserved protein motif that is generally present in the tail portion of signaling molecules expressed in many immune cells. The motif may include two repeats of the amino acid sequence YxxL/I separated by 6-8 amino acids, wherein each X is independently any amino acid, producing the conserved motif YxxL/Ix(6-8)YxxL/I. ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways. In some embodiments, the cytoplasmic signaling domain including at least 1, at least 2, at least 3, at least 4, or at least 5 ITAMs independently selected from the ITAMs derived from CD3ζ, FcRγ, Megf10, FcRγ, and combinations thereof.

In some embodiments, the intracellular signaling domain from the engulfment receptor is capable of mediating endogenous phagocytic signaling pathway. In some embodiments, the intracellular domain of the chimeric polypeptide includes a domain responsible for signal activation and/or transduction. Non-limiting examples of an intracellular domain suitable for the chimeric polypeptides disclosed herein include, the cytoplasmic portion of a surface receptor, co-stimulatory molecule, and any molecule that acts in concert to initiate signal transduction in the phagocytic cell (e.g., monocyte, macrophage or dendritic cell), as well as any derivative or variant of these elements and any synthetic sequence that has the same functional capability. In some embodiments, the chimeric polypeptide of the disclosure includes at least one intracellular domain derived from engulfment receptors such as, e.g., Megf10, FcRγ, Bai1, MerTK, TIM4, Stabilin-1, Stabilin-2, RAGE, CD300f, Integrin subunit αv, Integrin subunit β5, CD36, LRP1, SCARF1, C1Qa, and/or Axl.

In some embodiments, the chimeric polypeptide of the disclosure includes an amino acid sequence for one or more signal peptides. Generally, there are no specific limitations with respect to the position where the signal peptide is operably linked, e.g. fused, to the chimeric polypeptide. In some embodiments, the signal peptide is operably linked upstream (e.g., N-terminally) to the extracellular domain. The signal peptide can generally be any signal peptide known in the art. Non-limiting examples of signal peptides suitable for the compositions and methods disclosed herein include signal peptides derived from CD8, Megf10, FcRγ, Bai1, MerTK, TIM4, Stabilin-1, Stabilin-2, RAGE, CD300f, Integrin subunit αv, Integrin subunit β5, CD36, LRP1, SCARF1, C1Qa, and Axl.

In some embodiments, the CAR-P of the disclosure includes the following components: (a) an extracellular domain consisting of single chain antibody that recognizes an specific antigen or other binding motif that targets a specific protein or lipid moiety; (b) a signal peptide, or equivalent) and transmembrane segment that allows the CAR to insert into and be delivered to the plasma membrane; (c) an intracellular motif that consists of at least one ITAM motif and potentially additional domains that increase signal potential; and (d) inducing an activity of engulfment when expressed in a professional phagocyte or a cell with phagocytic potential.

With respect to the transmembrane domain, the chimeric polypeptide of the disclosure can be designed to include a transmembrane domain that connects the antigen binding domain to the intracellular domain. In some embodiment, the transmembrane domain is naturally associated with one or more of the domains in the chimeric polypeptide. In some embodiments, the transmembrane domain can be selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Transmembrane domains of particular use in this disclosure may be derived from, e.g., include at least the stalk and/or transmembrane region(s) of CD8, Megf10, FcRγ, Bai1, MerTK, TIM4, Stabilin-1, Stabilin-2, RAGE, CD300f, Integrin subunit αv, Integrin subunit β5, CD36, LRP1, SCARF1, C1Qa, Axl, CD45, and/or CD86. There are no specific limitations with respect to the position of the transmembrane domain within the chimeric polypeptide. In some embodiments, the transmembrane domain is operably linked downstream (e.g., C-terminally) of the extracellular domain and upstream of the at least one copy of the intracellular signaling domain from the engulfment receptor.

In some embodiments, the transmembrane domain may be synthetic, in which case it will include predominantly hydrophobic residues such as leucine and valine. Preferably a triplet of phenylalanine, tryptophan and valine will be inserted at each end of a synthetic transmembrane domain.

In some embodiments of the present disclosure, the chimeric polypeptide includes (a) a peptide signal; (b) an extracellular domain including an antigen-binding region specific for one or more cancer-associated antigens; (c) a transmembrane domain; (d) an intracellular signaling domain from an engulfment receptor; and (e) a p85-recruitment domain. In some embodiments, the chimeric polypeptide includes (a) a peptide signal from CD8; (b) an extracellular single chain antibody variable fragment (scFv) having specific affinity for CD19 or CD22; (c) a transmembrane domain from CD8; (d) an intracellular signaling domain from Megf10, FcRγ, Bai1, or MerTK; and (c) a p85-recruitment domain from CD19. In some embodiments of the present disclosure, the chimeric polypeptide includes, in the N-terminal to C-terminal direction, (a) a peptide signal; (b) an extracellular domain including an antigen-binding region specific for one or more cancer-associated antigens; (c) a transmembrane domain; (d) an intracellular signaling domain from an engulfment receptor; and (e) a p85-recruitment domain. In some embodiments, the chimeric polypeptide includes, in the N-terminal to C-terminal direction, (a) a peptide signal from CD8; (b) an extracellular single chain antibody variable fragment (scFv) having specific affinity for CD19 or CD22; (c) a transmembrane domain from CD8; (d) an intracellular signaling domain from Megf10, FcRγ, Bai1, or MerTK; and (c) a p85-recruitment domain from CD19.

In some embodiments disclosed herein, the chimeric polypeptide includes an amino acid sequence that has at least 80% sequence identity to an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9, or a functional fragment thereof. The terms "percent identity," as used herein in the context of two or more nucleic acids or proteins, refers to two or more sequences or subsequences that are the same or have a specified percentage of nucleotides or amino acids that are the same (e.g., about 60% sequence identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the complement of a test sequence. This definition also includes sequences that have deletions and/or additions, as well as those that have substitutions. Sequence identity typically exists over a region that is at least about 20 amino acids or nucleotides in length, or over a region that is 10-100 amino acids or nucleotides in length, or over the entire length of a given sequence.

If necessary, sequence identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

In some embodiments, the chimeric polypeptide includes an amino acid sequence that has at least 85%, at least 90%, at least 95%, at least 96%, at least 97%, at least 98%, at least 99%, or 100% sequence identity to an amino acid sequence selected from the group consisting of SEQ ID NO: 2, SEQ ID NO: 3, SEQ ID NO: 4, SEQ ID NO: 5, SEQ ID NO: 6, SEQ ID NO: 8, and SEQ ID NO: 9, or a functional fragment thereof. In some embodiments, the chimeric polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 2, or a functional fragment thereof. In some embodiments, the chimeric polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 3, or a functional fragment thereof. In some embodiments, the chimeric polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 4, or a functional fragment thereof. In some embodiments, the chimeric polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 5, or a functional fragment thereof. In some embodiments, the chimeric polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 6, or a functional fragment thereof. In some embodiments, the chimeric polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 8, or a functional fragment thereof. In some embodiments, the chimeric polypeptide includes an amino acid sequence that has at least 80%, at least 85%, at least 90%, at least 95%, at least 96%, at least 97%, at least 98%, at least 99%, or 100% sequence identity to the amino acid sequence of SEQ ID NO: 9, or a functional fragment thereof.

One skilled in the art will appreciate that the complete amino acid sequence can be used to construct a back-translated gene. For example, a DNA oligomer containing a nucleotide sequence coding for a given polypeptide can be synthesized. For example, several small oligonucleotides coding for portions of the desired polypeptide can be synthesized and then ligated. The individual oligonucleotides typically contain 5' or 3' overhangs for complementary assembly.

In addition to generating desired polypeptides via expression of nucleic acid molecules that have been altered by recombinant molecular biological techniques, a subject chimeric polypeptide in accordance with the present disclosure can be chemically synthesized. Chemically synthesized polypeptides are routinely generated by those of skill in the art.

Once assembled (by synthesis, recombinant methodology, site-directed mutagenesis or another method), the DNA sequences encoding a chimeric polypeptide as disclosed herein can be inserted into an expression vector and operably linked to an expression control sequence appropriate for expression of the chimeric polypeptide in the desired transformed host. Proper assembly can be confirmed by nucleotide sequencing, restriction mapping, and expression of a biologically active polypeptide in a suitable host. As is known in the art, in order to obtain high expression levels of a transfected gene in a host, the gene must be operably linked to transcriptional and translational expression control sequences that are functional in the chosen expression host.

Nucleic Acid Molecules

In one aspect, some embodiments disclosed herein relate to isolated, synthetic, or recombinant nucleic acid molecules encoding the chimeric polypeptides of the disclosure, expression cassettes, and expression vectors containing these nucleic acid molecules. In some embodiments, an isolated, synthetic, or recombinant nucleic acid molecule of the disclosure is operably linked to regulator sequences which allow expression of the chimeric polypeptides in a host cell or ex-vivo cell-free expression system.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

Nucleic acid molecules of the present disclosure can be nucleic acid molecules of any length, including nucleic acid molecules that are preferably between about 1 Kb and about 50 Kb, for example between about 2 Kb and about 40 Kb, between about 5 Kb and about 50 Kb, between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

The term "recombinant" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence.

In some embodiments disclosed herein, the nucleic acid molecules of the disclosure include a nucleic acid sequence encoding a chimeric polypeptides which includes (a) an extracellular domain including an antigen-binding region specific for one or more cancer-associated antigen; (b) a transmembrane domain; (c) at least one copy of an intracellular signaling domain from an engulfment receptor; and (d) at least one copy of a recruitment domain.

In some embodiments disclosed herein, the nucleic acid molecules include a nucleotide sequence encoding a polypeptide that includes (i) an amino acid sequence having at least 80% sequence identity to the amino acid sequence of a chimeric polypeptide as disclosed herein or a functional fragment thereof. In some embodiments, the nucleic acid molecules include a nucleotide sequence encoding a polypeptide that includes (i) an amino acid sequence having at least 85%, at least 90%, at least 95%, at least 96%, at least 97%, at least 98%, at least 99%, or 100% sequence identity to the amino acid sequence of a chimeric polypeptide as disclosed herein or a functional fragment thereof.

In some embodiments, the nucleic acid molecules include a nucleotide sequence that has at least 80%, at least 85%, at least 90%, at least 95%, at least 96%, at least 97%, at least 98%, at least 99%, or 100% sequence identity to a nucleotide sequence selected from the group consisting of S SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18, or a functional fragment thereof. In some embodiments, the nucleic acid molecules include a nucleotide sequence that has at least 80%, at least 85%, at least 90%, at least 95%, at least 96%, at least 97%, at least 98%, at least 99%, or 100% sequence identity to a nucleotide sequence selected from the group consisting of SEQ ID NO: 11, SEQ ID NO: 12, SEQ ID NO: 13, SEQ ID NO: 14, SEQ ID NO: 15, SEQ ID NO: 17, and SEQ ID NO: 18. In some embodiments, the nucleic acid molecules include a nucleotide sequence that has at least 80%, at least 85%, at least 90%, at least 95%, at least 96%, at least 97%, at least 98%, or at least 99% sequence identity to the nucleotide sequence of SEQ ID NO: 11, or a functional fragment thereof. In some embodiments, the nucleic acid molecules include a nucleotide sequence that has at least 80%, at least 85%, at least 90%, at least 95%, at least 96%, at least 97%, at least 98%, or at least 99% sequence identity to the nucleotide sequence of SEQ ID NO: 12, or a functional fragment thereof. In some embodiments, the nucleic acid molecules include a nucleotide sequence that has at least 80%, at least 85%, at least 90%, at least 95%, at least 96%, at least 97%, at least 98%, or at least 99% sequence identity to the nucleotide sequence of SEQ ID NO: 13, or a functional fragment thereof. In some embodiments, the nucleic acid molecules include a nucleotide sequence that has at least 80%, at least 85%, at least 90%, at least 95%, at least 96%, at least 97%, at least 98%, or at least 99% sequence identity to the nucleotide sequence of SEQ ID NO: 14, or a functional fragment thereof. In some embodiments, the nucleic acid molecules include a nucleotide sequence that has at least 80%, at least 85%, at least 90%, at least 95%, at least 96%, at least 97%, at least 98%, or at least 99% sequence identity to the nucleotide sequence of SEQ ID NO: 15, or a functional fragment thereof. In some embodiments, the nucleic acid molecules include a nucleotide sequence that has at least 80%, at least 85%, at least 90%, at least 95%, at least 96%, at least 97%, at least 98%, or at least 99% sequence identity to the nucleotide sequence of SEQ ID NO: 17, or a functional fragment thereof. In some embodiments, the nucleic acid molecules include a nucleotide sequence that has at least 80%, at least 85%, at least 90%, at least 95%, at least 96%, at least 97%, at least 98%, or at least 99% sequence identity to the nucleotide sequence of SEQ ID NO: 18, or a functional fragment thereof.

In some embodiments, the nucleic acid molecule as disclosed herein is operably linked to a heterologous nucleic acid sequence. Some embodiments disclosed herein relate to vectors or expression cassettes including an isolated, synthetic, or recombinant nucleic acid molecule as disclosed herein. The expression cassette generally contains coding sequences and enough regulatory information to direct proper transcription and/or translation of the coding sequences in a recipient cell, in vivo and/or ex vivo. The expression cassette may be inserted into a vector for targeting to a desired host cell and/or into a subject. As such, the term expression cassette may be used interchangeably with the term "expression construct". An expression cassette can be inserted into a plasmid, cosmid, virus, autonomously replicating polynucleotide molecule, phage, as a linear or circular, single-stranded or double-stranded, DNA or RNA polynucleotide molecule, derived from any source, capable of genomic integration or autonomous replication, including a nucleic acid molecule where one or more nucleic acid sequences has been linked in a functionally operative manner, i.e., operably linked.

Also provided herein are vectors, plasmids, or viruses containing one or more of the nucleic acid molecules encoding any one of the chimeric polypeptides disclosed herein. The nucleic acid molecules described above can be contained within a vector that is capable of directing their expression in, for example, a cell that has been transduced with the vector. Suitable vectors for use in eukaryotic and prokaryotic cells are known in the art and are commercially available or readily prepared by a skilled artisan. Additional vectors can also be found, for example, in Ausubel, F. M., et al., *Current Protocols in Molecular Biology*, (Current Protocol, 1994) and Sambrook et al., *"Molecular Cloning: A Laboratory Manual,"* 2nd ED. (1989).

It should be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, vectors that can be used include those that allow the DNA encoding the chimeric polypeptides of the present disclosure to be amplified in copy number. Such amplifiable vectors are known in the art. They include, for example, vectors able to be amplified by DHFR amplification (see, e.g., Kaufman, U.S. Pat. No. 4,470,461) or glutamine synthetase ("GS") amplification (see, e.g., U.S. Pat. No. 5,122,464 and European published application EP 338,841).

Accordingly, in some embodiments, the chimeric polypeptides of the present disclosure can be expressed from vectors, preferably expression vectors. The vectors are, in some embodiments, useful for autonomous replication in a host cell or, in certain embodiments, may be integrated into the genome of a host cell upon introduction into the host cell, and thereby are replicated along with the host genome (e.g., non-episomal mammalian vectors). Expression vectors are capable of directing the expression of coding sequences to which they are operably linked. In general, expression vectors of utility in recombinant DNA techniques are often in the form of plasmids (vectors). However, other forms of expression vectors, such as viral vectors (e.g., replication defective retroviruses, adenoviruses, and adeno-associated viruses) are also encompassed in this disclosure.

Exemplary recombinant expression vectors can include one or more regulatory sequences, selected on the basis of the host cells to be used for expression, operably linked to the nucleic acid sequence to be expressed.

DNA vector can be introduced into prokaryotic or eukaryotic cells via conventional transformation or transfection techniques. Suitable methods for transforming or transfecting host cells can be found in Sambrook et al. (1989) *Molecular Cloning: A Laboratory Manual* (2nd ed., Cold Spring Harbor Laboratory Press, Plainview, N.Y.) and other standard molecular biology laboratory manuals.

The nucleic acid sequences encoding the chimeric polypeptides of the present disclosure can be optimized for expression in the host cell of interest. For example, the G-C content of the sequence can be adjusted to levels average for a given cellular host, as calculated by reference to known genes expressed in the host cell. Methods for codon optimization are known in the art. Codon usages within the coding sequence of the chimeric polypeptides as disclosed herein can be optimized to enhance expression in the host cell, such that about 1%, about 5%, about 10%, about 25%, about 50%, about 75%, or up to 100% of the codons within the coding sequence have been optimized for expression in a particular host cell.

Non-limiting examples of vectors suitable for use include T7-based vectors for use in bacteria, the pMSXND expression vector for use in mammalian cells, and baculovirus-derived vectors for use in insect cells. In some embodiments nucleic acid inserts, which encode the subject chimeric polypeptide in such vectors, can be operably linked to a promoter, which is selected based on, for example, the cell type in which expression is sought. A non-limiting exemplification of suitable promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, MoMuLV promoter, an avian leukemia virus promoter, an Epstein-Barr virus immediate early promoter, mouse mammary tumor virus (MMTV), human immunodeficiency virus (HIV) long terminal repeat (LTR) promoter, a Rous sarcoma virus promoter, the elongation factor-1a promoter, as well as human gene promoters such as, but not limited to, the actin promoter, the myosin promoter, the hemoglobin promoter, and the creatine kinase promoter. Further, the disclosure should not be limited to the use of constitutive promoters. Inducible promoters are also contemplated as part of the disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In addition, any of a wide variety of expression control sequences can be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast a-mating system, the polyhedron promoter of Baculovirus, and other sequences known to control the expression of genes of prokaryotic or eukaryotic cells or their viruses, and various combinations thereof.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans will readily appreciate numerous promoters and other regulatory elements which can be used to direct expression of nucleic acids.

In selecting an expression control sequence, a variety of factors should also be considered. These include, for example, the relative strength of the sequence, its controllability, and its compatibility with the actual DNA sequence encoding the subject chimeric polypeptide, particularly as regards potential secondary structures. Hosts should be selected by consideration of their compatibility with the chosen vector, the toxicity of the product coded for by the DNA sequences of this disclosure, their secretion characteristics, their ability to fold the polypeptides correctly, their fermentation or culture requirements, and the ease of purification of the products coded for by the DNA sequences.

Within these parameters one of skill in the art may select various vector/expression control sequence/host combinations that will express the desired DNA sequences on fermentation or in large scale animal culture, for example, using CHO cells or COS 7 cells.

The choice of expression control sequence and expression vector, in some embodiments, will depend upon the choice of host. A wide variety of expression host/vector combinations can be employed. Non-limiting examples of useful expression vectors for eukaryotic hosts, include, for example, vectors with expression control sequences from SV40, bovine papilloma virus, adenovirus and cytomegalovirus. Non-limiting examples of useful expression vectors for bacterial hosts include known bacterial plasmids, such as plasmids from E. coli, including col El, pCRI, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Non-limiting examples of useful expression vectors for yeast cells include the 2µ plasmid and derivatives thereof. Non-limiting examples of useful vectors for insect cells include pVL 941 and pFastBac™ 1.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the disclosure include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Recombinant prokaryotic or eukaryotic cells that contain a chimeric polypeptide as disclosed herein, and/or contain and express a nucleic acid molecule that encodes any one of the chimeric polypeptide disclosed herein are also features of the disclosure. In some embodiments, a recombinant cell of the disclosure is a transfected cell, e.g., a cell into which a nucleic acid molecule, for example a nucleic acid molecule encoding a chimeric polypeptide disclosed herein, has been introduced by means of recombinant methodologies and techniques. The progeny of such a cell are also considered within the scope of the disclosure. Cell cultures containing at least one recombinant cell as disclosed herein are also within the scope of the present disclosure.

The precise components of the expression system are not critical. For example, an chimeric polypeptide as disclosed herein can be produced in a prokaryotic host, such as the bacterium E. coli, or in a eukaryotic host, such as an insect cell (e.g., an Sf21 cell), or mammalian cells (e.g., COS cells, NIH 3T3 cells, or HeLa cells). In some embodiments, the recombinant cell is a phagocytic cell, e.g., phagocyte. Both professional phagocytes and non-professional phagocytes are suitable. In some embodiments, the phagocytic cell is a professional phagocyte. In some embodiments, the phagocytic cell is a professional phagocyte. In some embodiments, the phagocytic cell is selected from the group consisting of macrophages, dendritic cells, mast cells, monocytes, neutrophils, microglia, and astrocytes. In some embodiments, the phagocytic cell is a BMDM or a BMDC. In some embodiments, the phagocytic cell is a J774A.1 macrophage. These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

In some embodiments, chimeric polypeptides obtained will be glycosylated or unglycosylated depending on the host organism used to produce the chimeric polypeptides. If bacteria are chosen as the host then the chimeric polypeptide produced will be unglycosylated. Eukaryotic cells, on the other hand, will typically glycosylate the chimeric polypeptides, although perhaps not in the same way as native polypeptides is glycosylated. The chimeric polypeptides produced by the transformed host cell can be purified according to any suitable methods known in the art. Produced chimeric polypeptides can be isolated from inclusion bodies generated in bacteria such as E. coli, or from conditioned medium from either mammalian or yeast cultures producing a given chimeric polypeptide using cation exchange, gel filtration, and or reverse phase liquid chromatography.

Accordingly, another exemplary method of constructing a DNA sequence encoding the chimeric polypeptides of the disclosure is by chemical synthesis. This includes direct synthesis of a peptide by chemical means of the protein sequence encoding for a chimeric polypeptide exhibiting the properties described. This method can incorporate both natural and unnatural amino acids at positions that affect the binding affinity of the chimeric polypeptide with the target antigen and/or target protein. Alternatively, a gene which encodes the desired chimeric polypeptide can be synthesized by chemical means using an oligonucleotide synthesizer. Such oligonucleotides are designed based on the amino acid sequence of the desired chimeric polypeptide, and preferably selecting those codons that are favored in the host cell in which the recombinant chimeric polypeptide will be produced. In this regard, it is well recognized in the art that the genetic code is degenerate—that an amino acid may be coded for by more than one codon. For example, Phe (F) is coded for by two codons, TIC or TTT, Tyr (Y) is coded for by TAC or TAT and his (H) is coded for by CAC or CAT. Trp (W) is coded for by a single codon, TGG. Accordingly, it will be appreciated by those skilled in the art that for a given DNA sequence encoding a particular chimeric polypeptide, there will be many DNA degenerate sequences that will code for that chimeric polypeptide. For example, it will be appreciated that in addition to the DNA sequences for chimeric polypeptides provided in the Sequence Listing, there will be many degenerate DNA sequences that code for the chimeric polypeptides disclosed herein. These degenerate DNA sequences are considered within the scope of this disclosure. Therefore, "degenerate variants thereof" in the context of this disclosure means all DNA sequences that code for and thereby enable expression of a particular chimeric polypeptide.

The DNA sequence encoding the subject chimeric polypeptide, whether prepared by site directed mutagenesis, chemical synthesis or other methods, can also include DNA sequences that encode a signal sequence. Such signal sequence, if present, should be one recognized by the cell chosen for expression of the chimeric polypeptide. It can be prokaryotic, eukaryotic or a combination of the two. In general, the inclusion of a signal sequence depends on whether it is desired to secrete the chimeric polypeptide as disclosed herein from the recombinant cells in which it is made. If the chosen cells are prokaryotic, it generally is preferred that the DNA sequence not encode a signal sequence. If the chosen cells are eukaryotic, it generally is preferred that a signal sequence be included.

The nucleic acid molecules provided can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (e.g., either a sense or an antisense strand).

The nucleic acid molecules are not limited to sequences that encode polypeptides; some or all of the non-coding sequences that lie upstream or downstream from a coding sequence (e.g., the coding sequence of a chimeric polypeptide disclosed herein) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Exemplary isolated nucleic acid molecules of the present disclosure can include fragments not found as such in the natural state. Thus, this disclosure encompasses recombinant molecules, such as those in which a nucleic acid sequence (for example, a sequence encoding a chimeric polypeptide disclosed herein) is incorporated into a vector (e.g., a plasmid or viral vector) or into the genome of a heterologous cell (or the genome of a homologous cell, at a position other than the natural chromosomal location).

Pharmaceutical Compositions

In some embodiments, the chimeric polypeptides, the nucleic acid molecules, and/or the recombinant cells the present disclosure can be incorporated into compositions, including pharmaceutical compositions. Such compositions typically include one or more of the chimeric polypeptides, the nucleic acid molecules, and/or the recombinant cells the present disclosure, and a pharmaceutically acceptable carrier.

In some embodiments, provided herein is a pharmaceutical composition including a pharmaceutically acceptable carrier, and one or more of the following: (a) a chimeric polypeptide including: (i) an extracellular domain including an antigen-binding region specific for one or more cancer-associated antigen; (ii) a transmembrane domain; (iii) at least one copy of an intracellular signaling domain from an engulfment receptor; and (iv) at least one copy of a recruitment domain; (b) a nucleic acid encoding the chimeric polypeptide of (a); and (c) a recombinant cell including the polypeptide of (a) and/or the nucleic acid of (b).

In some embodiments, provided herein is a pharmaceutical composition including a pharmaceutically acceptable carrier and a chimeric polypeptide that includes (i) an extracellular domain including an antigen-binding region specific for one or more cancer-associated antigen; (ii) a transmembrane domain; (iii) at least one copy of an intracellular signaling domain from an engulfment receptor; and (iv) at least one copy of a recruitment domain.

In some embodiments, provided herein is a pharmaceutical composition including a pharmaceutically acceptable carrier and a nucleic acid encoding a chimeric polypeptide disclosed herein. In some embodiments, provided herein is a pharmaceutical composition including a pharmaceutically acceptable carrier and a recombinant cell as disclosed herein.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, if used, generally include an inert diluent or an edible carrier. For the purpose of oral therapeutic administration, the active compound (e.g., chimeric polypeptides, nucleic acid molecules, and recombinant cells of the disclosure) can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

In the event of administration by inhalation, the subject chimeric polypeptides and/or nucleic acids molecules of the disclosure are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the subject chimeric polypeptides and/or nucleic acids molecules of the disclosure can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the chimeric polypeptides and nucleic acids molecules of the disclosure can also be prepared in the form of suppositories (e.g., with conventional suppository bases such as cocoa butter and other glycerides) or retention enemas for rectal delivery.

In some embodiments, the chimeric polypeptides and nucleic acids molecules of the disclosure can also be administered by transfection or infection using methods known in the art, including but not limited to the methods described in McCaffrey et al. (Nature 418:6893, 2002), Xia et al. (*Nature Biotechnol.* 20: 1006-1010, 2002), or Putnam (*Am. J. Health Syst. Pharm.* 53: 151-160, 1996, erratum at *Am. J. Health Syst. Pharm.* 53:325, 1996).

In some embodiments, the subject chimeric polypeptides and nucleic acids molecules of the disclosure are prepared with carriers that will protect the chimeric polypeptides and nucleic acids molecules against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Methods of the Disclosure

In one aspect, some embodiments of the disclosure relate to a method for modifying a cell including introducing into the cell (a) a chimeric polypeptide as described herein; and/or (b) an isolated, synthetic, or recombinant nucleic acid molecule as described herein, to produce a recombinant cell, e.g., transgenic cell. For example, a chimeric polypeptide or nucleic molecule as disclosed herein can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). In some embodiments, the recombinant cell is a phagocytic cell, e.g., phagocyte. Both professional phagocytes and non-professional phagocytes are suitable. In some embodiments, the phagocytic cell is a professional phagocyte. In some embodiments, the phagocytic cell is a professional phagocyte. In some embodiments, the phagocytic cell is selected from the group consisting of macrophages, dendritic cells, mast cells, monocytes, neutrophils, microglia, and astrocytes. In some embodiments, the phagocytic cell is a BMDM or a BMDC. These cells are available from many sources, including the American Type Culture Collection (Manassas, Va.). In some embodiments, the recombinant cell expresses the chimeric polypeptide and possesses targeted effector activity. In some embodiments, introducing the chimeric polypeptide into the cell includes introducing a nucleic acid sequence encoding the chimeric polypeptide. In some embodiments, introducing the nucleic acid sequence includes electroporating an mRNA encoding the chimeric polypeptide.

Methods of introducing and expressing genes, such as the nucleic acid molecules and the chimeric polypeptides encoded thereby, into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. Physical methods for introducing a polynucleotide into a host cell include calcium phosphate precipitation, lipofection, particle bombardment, microinjection, electroporation, and the like. Methods for producing cells including vectors and/or exogenous nucleic acids are well-known in the art. For example, nucleic acids can be introduced into target cells using commercially available methods which include electroporation. Nucleic acids can also be introduced into cells using cationic liposome mediated transfection using lipofection, using polymer encapsulation, using peptide mediated transfection, or using biolistic particle delivery systems such as "gene guns".

Biological methods for introducing a polynucleotide of interest into a host cell include the use of DNA and RNA vectors. RNA vectors include vectors having a RNA promoter and/other relevant domains for production of a RNA transcript. Viral vectors, and especially retroviral vectors, have become the most widely used method for inserting genes into mammalian, e.g., human cells. Other viral vectors may be derived from lentivirus, poxviruses, herpes simplex virus, adenoviruses and adeno-associated viruses, and the like. Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. "Liposome" is a generic term encompassing a variety of single and multi-lamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. However, compositions that have different structures in solution than the normal vesicular structure are also encompassed. For example, the lipids may assume a micellar structure or merely exist as non-uniform aggregates of lipid molecules. Also contemplated are lipofectamine-nucleic acid complexes The use of lipid formulations is contemplated for the introduction of the nucleic acids into a host cell (in vitro, ex vivo or in vivo). In some embodiments, the nucleic acid molecule or chimeric polypeptide may be associated with a lipid. The nucleic acid molecule or chimeric polypeptide associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Methods of Treatment

The chimeric polypeptides, nucleic acid molecules, and/or pharmaceutical compositions of the disclosure can be used to treat individuals who have, who are suspected of having, or who may be at high risk for developing one or more health conditions or disorders. Exemplary health conditions and disorders of interest can include, without limitation, those associated with acute and chronic infections, inflammatory diseases, immune diseases, and various cancers. In some embodiments, the methods disclosed herein are useful in treating the one or more health conditions or disorders by enhancing the removal of infected, transformed, malignant, apoptotic, damaged or necrotic cells or particles from the individual's body.

The term "cancer" as used herein refers to a disease characterized by the rapid and uncontrolled growth of aberrant cells. The aberrant cells may form solid tumors or constitute a hematological malignancy. Cancer cells can spread locally or through the bloodstream and lymphatic system to other parts of the body. There are no specific limitations with respect to the cancers which can be treated by the compositions and methods of the present disclosure. Non-limiting examples of suitable cancers include ovarian cancer, renal cancer, breast cancer, prostate cancer, liver cancer, brain cancer, lymphoma, leukemia, cervical cancer, skin cancer, pancreatic cancer, colorectal cancer, lung cancer and the like. Other cancers that can be suitable treated with the compositions and methods of the present disclosure include, but are not limited to, AML, ALL, CML, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, transitional cell carcinoma, vaginal cancer, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, gallbladder cancer, gastrointestinal carcinoid tumors, gastrointestinal stromal tumors, gestational trophoblastic disease, Hodgkin's lymphoma, Kaposi's sarcoma, kidney cancer, laryngeal and hypopharyngeal cancer, liver cancer, lung cancer, lung carcinoid tumors, brain cancers, central nervous system (CNS) cancers, peripheral nervous system (PNS) cancers, breast cancer, cervical cancer, childhood Non-Hodgkin's lymphoma, colon and rectum cancer, Non-Hodgkin's lymphoma, malignant mesothelioma, multiple myeloma, myelodysplastic syndrome, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g., uterine sarcoma), transitional cell carcinoma, vaginal cancer, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g., uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, or Waldenstrom's macroglobulinemia. Particularly suitable cancers include, but are not limited to, breast cancer, ovarian cancer, lung cancer, pancreatic cancer, mesothelioma, leukemia, lymphoma, brain cancer, prostate cancer, multiple myeloma, melanoma, bladder cancer, bone sarcomas, soft tissue sarcomas, retinoblastoma, renal tumors, neuroblastoma, and carcinomas.

In another aspect, some embodiments of the disclosure relate to method for treating an individual having cancer, which includes administering to the individual an effective numbers of a phagocytic cells that has been modified to express a chimeric engulfment receptor having specific affinity for an antigen associated with a cancer cell. In some embodiments, the cell is a phagocytic cell selected from the group consisting of macrophages, dendritic cells, mast cells, monocytes, neutrophils, microglia, and astrocytes. In some embodiments, the phagocytic cell is a BMDM or a BMDC.

In some embodiments, the phagocytic cell is derived from the same individual having cancer, where phagocytes are removed from an individual (blood, tumor or ascites fluid), and modified so that they express the CAR-P receptors specific to a particular form of antigen associated with the individual's cancer. In yet some embodiments, the method further includes modifying the phagocytic cell to deliver an agent to a target, wherein the agent is selected from the group consisting of a nucleic acid, an antibiotic, an anti-inflammatory agent, an antibody or antibody fragments thereof, a growth factor, a cytokine, an enzyme, a protein, a peptide, a fusion protein, a synthetic molecule, an organic molecule, a carbohydrate or the like, a lipid, a hormone, a microsome, a derivative or a variation thereof, and any combination thereof.

In yet another aspect, some embodiments of the disclosure relate to method for treating an individual having cancer, which includes administering to the individual an effective amount or number of: (a) a chimeric polypeptide as described herein; (b) an isolated, synthetic, or recombinant nucleic acid molecule as described herein; (c) a recombinant cell as described herein; and/or a pharmaceutical composition as described herein. Accordingly, in some embodiments, the treatment method includes administering to the individual an effective amount of one or more chimeric polypeptides as described herein. In some embodiments, the treatment method includes administering to the individual an effective amount of one or more isolated, synthetic, or recombinant nucleic acid molecule as described herein. In some embodiments, the treatment method includes administering to the individual an effective numbers of one or more recombinant phagocytic cells as described herein.

In principle, there are no specific limitations with respect to the procedures and techniques that can be suitably employed for delivery of the chimeric polypeptides, nucleic acid molecules, and/or recombinant cells as described herein into the target cell. Non-limiting delivery procedures suitable for the methods disclosed herein include stable or transient transfection, lipofection, electroporation, microinjection, liposomes, iontophoresis, and infection with recombinant viral vectors. In some embodiments, the administration includes a viral-, particle-, liposome-, or exosome-based delivery procedure. In some embodiments, the administration includes delivering into endogenous cells ex vivo one or more gene-editing enzymes targeting (a) a chimeric polypeptide as described herein; and/or (b) an isolated, synthetic, or recombinant nucleic acid molecule as described herein. In some embodiments, the administration includes delivering into cells in vivo one or more gene-editing enzymes targeting (a) a chimeric polypeptide as described herein; and/or (b) an isolated, synthetic, or recombinant nucleic acid molecule as described herein. In some embodiments, the administration of the chimeric polypeptides, nucleic acid molecules, and/or recombinant cells as described herein activates phagocytosis of said cancer cell. In some embodiments, the activated phagocytosis includes whole-cell internalization. In some embodiments, the activated phagocytosis includes bite internalization. In some embodiments, the activated phagocytosis includes both whole-cell internalization and bite internalization.

Typically, a pharmaceutical composition is formulated to be compatible with its intended route of administration. The chimeric polypeptides, nucleic acid molecules, and/or pharmaceutical compositions of the disclosure may be given orally or by inhalation, but it is more likely that they will be administered through a parenteral route. Examples of parenteral routes of administration include, for example, intravenous, intradermal, subcutaneous, transdermal (topical), transmucosal, and rectal administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Dosage, toxicity and therapeutic efficacy of such subject chimeric polypeptides, nucleic acid molecules, and/or pharmaceutical compositions of the disclosure can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such chimeric polypeptides, nucleic acid molecules, and/or pharmaceutical compositions lies preferably within a range of circulating concentrations that include the ED50 with little or no toxicity. The dosage may vary within this range depending upon the dosage form employed and the route of administration utilized. For any molecules or compositions used in the methods of the disclosure, the therapeutically effective dose can be estimated initially from cell culture assays. A dose may be formulated in animal models to achieve a circulating plasma concentration range that includes the IC50 (e.g., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a "therapeutically effective amount or number" of a subject chimeric polypeptide or nucleic acid molecule or a recombinant cell of the disclosure (e.g., an effective dosage) depends on the polypeptide selected. For instance, single dose amounts in the range of approximately 0.001 to 0.1 mg/kg of patient body weight can be administered; in some embodiments, about 0.005, 0.01, 0.05 mg/kg may be administered. In some embodiments, 600,000 IU/kg is administered (IU can be determined by a lymphocyte proliferation bioassay and is expressed in International Units (IU) as established by the World Health Organization International Standard). The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount or number of the subject chimeric polypeptides, nucleic acid molecules, and/or recombinant cells of the disclosure can include a single treatment or, can include a series of treatments. In some embodiments, the compositions are administered every 8 hours for five days, followed by a rest period of 2 to 14 days, e.g., 9 days, followed by an additional five days of administration every 8 hours.

There are no specific limitations with respect to the cancers which can be treated by the compositions and methods of the present disclosure. Non-limiting examples of suitable cancers include ovarian cancer, renal cancer, breast cancer, prostate cancer, liver cancer, brain cancer, lymphoma, leukemia, cervical cancer, skin cancer, pancreatic cancer, colorectal cancer, lung cancer and the like. Other cancers that can be suitable treated with the compositions and methods of the present disclosure include, but are not limited to, AML, ALL, CML, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, transitional cell carcinoma, vaginal cancer, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, gallbladder cancer, gastrointestinal carcinoid tumors, gastrointestinal stromal tumors, gestational trophoblastic disease, Hodgkin's lymphoma, Kaposi's sarcoma, kidney cancer, laryngeal and hypopharyngeal cancer, liver cancer, lung cancer, lung carcinoid tumors, brain cancers, central nervous system (CNS) cancers, peripheral nervous system (PNS) cancers, breast cancer, cervical cancer, childhood Non-Hodgkin's lymphoma, colon and rectum cancer, Non-Hodgkin's lymphoma, malignant mesothelioma, multiple myeloma, myelodysplastic syndrome, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g., uterine sarcoma), transitional cell carcinoma, vaginal cancer, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g., uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, or Waldenstrom's macroglobulinemia. Particularly suitable cancers include, but are not limited to, breast cancer, ovarian cancer, lung cancer, pancreatic cancer, mesothelioma, leukemia, lymphoma, brain cancer, prostate cancer, multiple myeloma, melanoma, bladder cancer, bone sarcomas, soft tissue sarcomas, retinoblastoma, renal tumors, neuroblastoma, and carcinomas.

Accordingly, in some embodiments of the disclosure, the individual in need of treatment has or is suspected of having a cancer which is selected from the group consisting of breast cancer, ovarian cancer, lung cancer, pancreatic cancer, mesothelioma, leukemia, lymphoma, prostate cancer, multiple myeloma, melanoma, bladder cancer, bone sarcomas, soft tissue sarcomas, retinoblastoma, renal tumors, neuroblastoma, and carcinomas.

Kits

Some embodiments of the disclosure provide a kit that contains any of the above-described compositions, e.g. chimeric polypeptides, nucleic acid molecules, recombinant cells, and pharmaceutical compositions.

In some embodiments, a kit can further include instructions for using the components of the kit to practice the methods described herein. The instructions for practicing the methods are generally recorded on a suitable recording medium. For example, the instructions can be printed on a substrate, such as paper or plastic, etc. The instructions can be present in the kit as a package insert, in the labeling of the container of the kit or components thereof (e.g., associated with the packaging or subpackaging), etc. The instructions can be present as an electronic storage data file present on a suitable computer readable storage medium, e.g., CD-ROM, diskette, flash drive, etc. In some embodiments, the actual instructions are not present in the kit, but means for obtaining the instructions from a remote source (e.g., via the Internet), can be provided. An example of this embodiment is a kit that includes a web address where the instructions can be viewed and/or from which the instructions can be downloaded. As with the instructions, this means for obtaining the instructions can be recorded on a suitable substrate.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

EXAMPLES

The practice of the present disclosure will employ, unless otherwise indicated, conventional techniques of molecular biology, microbiology, cell biology, biochemistry, nucleic acid chemistry, and immunology, which are well known to those skilled in the art. Such techniques are explained fully in the literature, such as Sambrook, J., & Russell, D. W. (2012). *Molecular Cloning: A Laboratory Manual* (4th ed.). Cold Spring Harbor, N.Y.: Cold Spring Harbor Laboratory and Sambrook, J., & Russel, D. W. (2001). *Molecular Cloning: A Laboratory Manual* (3rd ed.). Cold Spring Harbor, N.Y.: Cold Spring Harbor Laboratory (jointly referred to herein as "Sambrook"); Ausubel, F. M. (1987). *Current Protocols in Molecular Biology*. New York, N.Y.: Wiley (including supplements through 2014); Bollag, D. M. et al. (1996). *Protein Methods*. New York, N.Y.: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, Calif.: Academic Press; Lefkovits, I. (1997). *The Immunology Methods Manual: The Comprehensive Sourcebook of Techniques*. San Diego, Calif.: Academic Press; Doyle, A. et al. (1998). *Cell and Tissue Culture: Laboratory Procedures in Biotechnology*. New York, N.Y.: Wiley; Mullis, K. B., Ferre, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, N.Y.: Cold Spring Harbor Laboratory Press; Beaucage, S. L. et al. (2000). *Current Protocols in Nucleic Acid Chemistry*. New York, N.Y.: Wiley, (including supplements through 2014); and Makrides, S. C. (2003). *Gene Transfer and Expression in Mammalian Cells*. Amsterdam, NL: Elsevier Sciences B.V., the disclosures of which are incorporated herein by reference. As appropriate, procedures involving the use of commercially available kits and reagents are generally carried out in accordance with manufacturer defined protocols and/or parameters unless otherwise noted.

Additional embodiments are disclosed in further detail in the following examples, which are provided by way of illustration and are not in any way intended to limit the scope of this disclosure or the claims.

Example 1

General Experimental Procedures

Constructions, Antibodies, Reagents, and Cell Lines

This section describes the construction of constructs and antibodies. Detailed information for all constructs, antibodies, reagents, and cell lines can be found in TABLE 1 (Key resources table). This table also includes the following information for various receptors developed in this study: signal peptide, extracellular antibody fragment, stalk/transmembrane domain, and cytosolic tail including appropriate accession numbers.

TABLE 1

| Reagent type (species) or resource | Designation | Source or reference | ID | Additional information |
|---|---|---|---|---|
| Cell line (*Mus musculus*) | J774A.1 Macrophages | UCSF Cell Culture Facility | | |
| Cell line (*Homo sapiens*) | Raji B Cells | Other | | Obtained from M. McManus, UCSF |
| Cell line (*Mus musculus*) | 3T3 Fibroblasts | UCSF Cell Culture Facility | | |
| Cell line (*Mus musculus*) | C57BL/6J | PMID: 21356739 | | Bone Marrow Derived Macrophages (BMDM) |
| Cell line (*Mus musculus*) | C57BL/6J | PMID: 7489412 | | Bone Marrow derived Dendritic Cells (BMDC) |
| Cell line (*Homo sapiens*) | HEK293T cells | UCSF Cell Culture Facility | | Lentivirus production |
| Genetic Reagent (*Mus musculus*) | OTI | PMID: 8287475 | | E. Roberts/M. Krummel Lab UCSF |
| Recombinant DNA reagent | CD19-mMegf10 CAR | this disclosure | | Signal peptide: aa 1-21 CD8 (Uniprot Q96QR6_HUMAN) Extracellular antibody sequence: V-L chain: aa 23-130 anti-CD19 CAR (Genbank AMZ04819) -- GS linker: ggtggcggtggctcgggcggtggtgggtcgg gt ggcggcggatct -- V-H chain: aa 148-267 anti-CD19 CAR (Genbank AMZ04819) Stalk/Transmembrane: aa 138-206 CD8 (Uniprot Q96QR6_HUMAN) Cytosolic sequence: aa 879-1147 Mouse Megf10 (Uniprot Q6DIB5 (MEG10_MOUSE)) Fluorophore: mGFP |

TABLE 1-continued

Key resource table

| Reagent type (species) or resource | Designation | Source or reference | ID | Additional information |
|---|---|---|---|---|
| Recombinant DNA reagent | CD19-FcGamma CAR | this disclosure | | Signal peptide: aa 1-21 CD8 (Uniprot Q96QR6_HUMAN) Extracellular antibody sequence: V-L chain: aa 23-130 anti-CD19 CAR (Genbank AMZ04819) -- GS linker: ggtggcggtggctcgggcggtggtgggtcgg gtggcggcggatct -- V-H chain: aa 148-267 anti-CD19 CAR (Genbank AMZ04819) Stalk/Transmembrane: aa 138-206 CD8 (Uniprot Q96QR6_HUMAN) Cytosolic sequence: aa 19-86 Mouse Fc ERG precursor (Uniprot P20491 (FCERG_MOUSE)) Fluorophore: mGFP |
| Recombinant DNA reagent | CD19-empty CAR | this disclosure | | Signal peptide: aa 1-21 CD8 (Uniprot Q96QR6_HUMAN) Extracellular antibody sequence: V-L chain: aa 23-130 anti-CD19 CAR (Genbank AMZ04819) -- GS linker: ggtggcggtggctcgggcggtggtgggtcgg g tggcggcggatct -- V-H chain: aa 148-267 anti-CD19 CAR (Genbank AMZ04819) Stalk/Transmembrane: aa 138-206 CD8 (Uniprot Q96QR6_HUMAN) Cytosolic sequence: basic linker NHRNRRR (nucleotide AACCACAGGAACCGAAGACG T) Fluorophore: mGFP |
| Recombinant DNA reagent | CD22-Megf10 CAR | this disclosure | | Signal peptide: aa 1-21 CSF2R (Uniprot P15509 (CSF2R_HUMAN)) Extracellular antibody sequence: aa 22-258 of translated JP 2016502512-A/1: M971 Chimeric Antigen (Genbank HZ530416.1) Stalk/Transmembrane: aa 138-206 CD8 (Uniprot Q96QR6_HUMAN) Cytosolic sequence: aa 879-1147 Mouse Megf10 (Uniprot Q6DIB5 (MEG10_MOUSE)) Fluorophore: mGFP |
| Recombinant DNA reagent | CD19-MerTK CAR | this disclosure | | Signal peptide: aa 1-21 CD8 (Uniprot Q96QR6_HUMAN) Extracellular antibody sequence: V-L chain: aa 23-130 anti-CD19 CAR (Genbank AMZ04819) -- GS linker: ggtg gcggtggctcgggcggtggtgggtcggtgg cggcggatct -- V-H chain: aa 148-267 anti-CD19 CAR (Genbank AMZ04819) Stalk/Transmembrane: aa 138-206 CD8 (Uniprot Q96QR6_HUMAN) Cytosolic sequence: aa 519-994 Mouse MerTK (Uniprot Q60805 (MERTK_MOUSE)) Fluorophore: mGFP |

TABLE 1-continued

Key resource table

| Reagent type (species) or resource | Designation | Source or reference | ID | Additional information |
|---|---|---|---|---|
| Recombinant DNA reagent | CD19-Bai1 CAR | this disclosure | | Signal peptide: aa 1-21 CD8 (Uniprot Q96QR6_HUMAN)Extracellular antibody sequence: V-L chain: aa 23-130 anti-CD19 CAR (Genbank AMZ04819)-- GS linker: ggtggcggtggctcgggcggtggtgggtcgg gtggcgg cggatct -- V-H chain: aa 148-267 anti-CD19 CAR (GenbankAMZ04819) Stalk/Transmembrane: aa 138-206 CD8 (UniprotQ96QR6_HUMAN) Cytosolic sequence: aa1188-1582 Mouse Bai1 (Uniprot Q3UHD1 (BAI1_MOUSE)) Fluorophore: mGFP |
| Recombinant DNA reagent | CD19-CD3 zeta CAR | this disclosure | | Signal peptide: aa 1-21 CD8 (Uniprot Q96QR6_HUMAN) Extracellular antibody sequence: V-L chain: aa 23-130 anti-CD19 CAR (Genbank AMZ04819) -- GS linker: ggtggcggtggctcg ggcggtggtgggtcggtggcggcggatct -- V-H chain: aa 148-267 anti-CD19 CAR (Genbank AMZ04819) Stalk/Transmembrane: aa 138-206 CD8 (Uniprot Q96QR6_HUMAN) Cytosolic sequence: aa 52-164, Human TCR CD3 zeta chain (Uniprot P20963) Fluorophore: sfGFP |
| Recombinant DNA reagent | CD19-PI3K CAR | this disclosure | | Signal peptide: aa 1-21 CD8 (Uniprot Q96QR6_HUMAN) Extracellular antibody sequence: V-L chain: aa 23-130 anti-CD19 CAR (Genbank AMZ04819) -- GS linker: ggtggcggtggct cgggcggtggtgggtcgggtggcggcggatc t -- V-H chain: aa 148-267 anti-CD19 CAR (Genbank AMZ04819) Stalk/Transmembrane: aa 138-206 CD8 (Uniprot Q96QR6_HUMAN) Cytosolic sequence: aa 500-534 Mouse CD19 (Uniprot CD19_MOUSE) Fluorophore: mCherry |
| Recombinant DNA reagent | CD19 tandem CAR | this disclosure | | Signal peptide: aa 1-21 CD8 (Uniprot Q96QR6_HUMAN) Extracellular antibody sequence: V-L chain: aa 23-130 anti-CD19 CAR (Genbank AMZ04819) -- GS linker: ggtggcggtggctc gggcggtggtgggtcgggtggcggcggatct -- V-H chain: aa 148-267 anti-CD19 CAR (Genbank AMZ04819) Stalk/Transmembrane: aa 138-206 CD8 (Uniprot Q96QR6_HUMAN) Cytosolic sequence: aa 500-534 Mouse CD19 (Uniprot CD19_MOUSE) fused to aa 19-86 Mouse Fc ERG precursor (FCERG_MOUSE) Fluorophore: mGFP |

TABLE 1-continued

Key resource table

| Reagent type (species) or resource | Designation | Source or reference | ID | Additional information |
|---|---|---|---|---|
| Recombinant DNA reagent | GFP-CaaX | this disclosure | | eGFP fused to a c terminal CaaX targeting sequence: aaaatgtccaaggatggta agaaaaagaagaagaagtcaaaaaccaagtgt gttatcatg |
| Recombinant DNA reagent | mCherry-CaaX | this disclosure | | mCherry fused to a c terminal CaaX targeting sequence: aaaatgtccaaggatggt aagaaaaagaagaagaagtcaaaaaccaagt gtgttatcatg |
| Recombinant DNA reagent | OVA/p2a/mCherry-CaaX | this disclosure | | Cytoplasmic Ovalbumin (UNIPROT: SERPINB14)/p2 a site: GGAAGCGGAGCTACTAA CTTCAGCCTGCTGAAGCAGG CTGGAGA CGTGGAGGAGAACCCTGGAC CT/followed by mCherry fused to a c terminal CaaX targeting sequence: aaaatgtccaaggatggtaagaaaaagaag aagaagtcaaaaaccaagtgtgttatcatg |
| Peptide, recombinant protein | His10-CD3 zeta | Hui and Vale (2014) PMID: 24463463 | | aa 52-164, Human TCR CD3 zeta chain (Uniprot CD3Z_HUMAN) fused to Hisx10 tag |
| Peptide, recombinant protein | His10-FcRγ | this disclosure | | aa 45-85, Human FcRγ (Uniprot FCERG_HUMAN) fused to Hisx10 tag |
| Peptide, recombinant protein | SNAP-Syk tSH2 | this disclosure | | aa 1-262, Mouse Syk (Uniprot KSYK_MOUSE) with N-term SNAP tag |
| Peptide, recombinant protein | His10-Lck Y505F | Hui and Vale (2014) PMID: 24463463 | | full length Human Lck with inhibitory Tyr 505 mutated to Phe (Uniprot LCK_HUMAN) fused to Hisx10 tag |
| Antibody | anti phospho-Tyrosine | Santa Cruz | PY20 | 1:100 IF primary |
| Antibody | anti mouse IgG coupled to Alexa Fluor 647 | Thermo Fisher Scientific/Lifetech | A21236 | 1:200 IF secondary |
| Antibody | anti mouse CD11c coupled to APC | BioLegend | 117313 | FACS |
| Antibody | anti mouse F4/80 coupled to APC/Cy7 | BioLegend | 123117 | FACS |
| Other | DMEM | Gibco | 11965-092 | |
| Other | Pen-Strep-Glutamine | Corning | 30-009 Cl | |
| Other | Fetal Bovine Serum (FBS) | Atlanta Biologicals | S1150H | |
| Other | RPMI | Gibco | 11875-093 | |
| Other | HEPES | Gibco | 1530080 | |
| Other | 2-Mercaptoethanol | Sigma | M6250-100 mL | |
| Commercial assay or kit | MycoAlert Mycoplasma Testing Kit | Lonza | LT07-318 | |
| Recombinant DNA reagent | pMD2.G lentiviral plasmid | other | Addgene 12259 | D. Stainier, Max Planck; VSV-G envelope |
| Recombinant DNA reagent | pCMV-dR8.91 | other | Current Addgene 8455 | |
| Recombinant DNA reagent | pHRSIN-CSGW | other | | As cited James and Vale (2012), PMID: 22763440 |
| Other | Lipofectamine LTX | Invitrogen | 15338-100 | Lentivirus production |
| Other | Lipofectamine | Invitrogen | 18324-012 | Added to spin infections to improve transduction |

TABLE 1-continued

Key resource table

| Reagent type (species) or resource | Designation | Source or reference | ID | Additional information |
|---|---|---|---|---|
| Other | Hamilton Gastight Syringes | Hamilton | 8 1100 | |
| Other | POPC | Avanti | 850457 | |
| Other | N12 + -DGS-NTA | Avanti | 790404 | |
| Other | PEG5000-PE | Avanti | 880230 | |
| Other | atto390 DOPE | ATTO-TEC GmbH | AD 390-161 | |
| Other | PBS (Tissue Culture Grade) | Gibco | 20012050 | |
| Other | Bioruptor Pico | Diagenode | | Used for producing SUVs |
| Other | 5 um silica microspheres | Bangs | SS05N | |
| Peptide, recombinant protein | CD19-His8 | Sino Biological | 11880H08H50 | |
| Peptide, recombinant protein | CD22-His8 | Sino Biological | 11958H08H50 | |
| Other | 2.5 um silica microspheres (size titration) | Corpuscular | C-SIO-2.5 | |
| Other | 5 um silica microspheres (size titration) | Corpuscular | C-SIO-5 | |
| Other | 10 um silica microspheres (size titration) | Corpuscular | C-SIO-10 | |
| Other | 15 um silica microspheres (size titration) | Corpuscular | C-SIO-15 | |
| Other | 20 um silica microspheres (size titration) | Corpuscular | C-SIO-20 | |
| Other | Low retention tubes for microsphere cleaning | Eppendorf | 22431081 | |
| Other | MatriPlate | Brooks | MGB096-1-2-LG-L | |
| Peptide, recombinant protein | M-CSF | Peprotech | 315-02 | |
| Other | IMDM | Thermo Fisher Scientific | 12440079 | |
| Other | Retronectin | Clontech | T100A | |
| Commercial assay or kit | CD8 + T cell purification kit | Stemcell | 19853 | |
| Other | eFluor670 proliferation dye | Thermo Fisher Scientific | 65-0840-85 | |
| Chemical compound, drug | phRSIN-CSGW | Sigma | L4516 | |
| Other | Fluorobrite DMEM | Gibco | A1896701 | |
| Other | DMEM minus phenol red | Gibco | A14430-01 | |
| Other | Rhodamine PE | Avanti | 810150C | |
| Other | DOPS | Avanti | 840035C | |
| Other | SNAP-Cell 505-Star | NEB | S9103S | |
| Other | PD MiniTrap G-25 column | GE Healthcare | 28-9225-29 AB | |
| Other | 6.4% Paraformaldehyde solution | Electron Microscopy Sciences | 50980495 | |
| Chemical compound, drug | AlexaFluor 647 Phalloidin | Thermo Fisher Scientific/ Molecular Probes | A22284 | |
| Software, algorithm | ImageJ | NIH | | |
| Software, algorithm | Illustrator | Adobe | CC, CS6 | |

TABLE 1-continued

Key resource table

| Reagent type (species) or resource | Designation | Source or reference | ID | Additional information |
|---|---|---|---|---|
| Software, algorithm | Photoshop | Adobe | CC, CS6 | |
| Software, algorithm | Fiji | https://fiji.sc/ | | |
| Software, algorithm | Prism | GraphPad | 7 | |
| Antibody | anti human CD19 (mouse antibody) | OriGene | TA506240 Clone OTI2F6 | IgG2a mouse monoclonal antibody |
| Antibody | anti human CD47 (mouse antibody) | BD Biosciences | 556044 Clone B6H12 | IgG1 mouse monoclonal antibody |
| Antibody | anti Ovalbumin (rabbit antibody) | Pierce | PAI-196 | IgG rabbit polyclonal antibody |

Cell Cultures

J774A.1 macrophages and NIH 3T3 fibroblasts were obtained from the UCSF cell culture facility and cultured in DMEM (Gibco, Catalog #11965-092) supplemented with 1×Pen-Strep-Glutamine (Corning, Catalog #30-009 Cl) and 10% fetal bovine serum (FBS) (Atlanta Biologicals, Catalog #511150H). Raji B cells were obtained from J. Blau (McManus lab, UCSF) and cultured in RPMI (Gibco, Catalog #11875-093) supplemented with 1×Pen-Strep-Glutamine (Corning, Catalog #30-009 Cl), 10% FBS (Atlanta Biologicals, Catalog #511150H), 10 mM HEPES (Gibco, Catalog #1530080), and 5 µM 2-Mercaptoethanol (Sigma, Catalog #M6250-100 mL). All cell lines used in this study were tested for *Mycoplasma* at least once per month using the Lonza MycoAlert Detection Kit (Lonza, Catalog #LT07-318) and control set (Lonza, Catalog #LT07-518).

Lentivirus Production and Infection

Lentiviral infection was used to stably express CAR-P constructs in all cell types. Lentivirus was produced by HEK293T cells transfected with pMD2.G (a gift from Didier Tronon, Addgene plasmid #12259 containing the VSV-G envelope protein), pCMV-dR8.91 (since replaced by second generation compatible pCMV-dR8.2, Addgene plasmid #8455), and a lentiviral backbone vector containing the construct of interest (derived from pHRSIN-CSGW) using lipofectamine LTX (Invitrogen, Catalog #15338-100). The media on the HEK293T cells was replaced with fresh media 8-16 hours post transfection to remove transfection reagent. At 50-72 hours post-transfection, the lentiviral media was filtered with a 0.45 µm filter and concentrated by centrifugation at 8000×g for 4 hours or overnight. The concentrated supernatant was applied directly to ~0.5×10$^6$ NIH 3T3 cells in 2 ml of fresh media. For J77A4.1 macrophages and Raji B cells, the concentrated supernatant was mixed with 2 ml of media and 2 µg lipofectamine (Invitrogen, Catalog #18324-012) and added to the cells. The cells were spun at 2200×g for 45 minutes at 37° C. Cells were analyzed a minimum of 72 hours later.

Preparation of CD19 and CD22.5 µm Silica Beads

Chloroform-suspended lipids were mixed in the following molar ratio using clean glass-tight Hamilton syringes (Hamilton, Catalog #8 1100): 97% POPC (Avanti, Catalog #850457), 2% Ni2+-DGS-NTA (Avanti, Catalog #790404), 0.5% PEG5000-PE (Avanti, Catalog #880230, and 0.5% atto390-DOPE (ATTO-TEC GmbH, Catalog #AD 390-161). Lipid mixes were dried under argon and desiccated overnight under foil. Dried lipids were resuspended in 1 ml tissue-culture grade PBS, pH 7.2 (Gibco, Catalog #20012050), and stored under argon gas. Small unilamellar vesicles were formed by five freeze-thaw cycles followed by 2×5 minutes of bath sonication (Bioruptor Pico, Diagenode), and cleared by ultracentrifugation (TLA120.1 rotor, 35,000 rpm/53,227×g, 35 min, 4° C.) or by 33 freeze thaw cycles. Lipid mixes were used immediately for form bilayers or shock frozen in liquid nitrogen and stored under argon at −80° C. To form bilayers on silica beads, 6×10$^8$ 5 µm silica microspheres (10% solids, Bangs Labs, Catalog #SS05N) were washed 2× in water, and 2× in PBS by sequential suspension in water and spinning at 800 rcf, followed by decanting. Cleaned beads were resuspended in 150 µl tissue-culture grade PBS, pH7.2 (Gibco, Catalog #20012050) and briefly vortexed. 30 µl cleared SUVs prepared as above as a 10 mM stock were added to bead suspension for a 2 mM final SUV concentration. Beads were vortexed for 10 seconds, covered in foil, and rotated for 30 minutes at room temperature to form bilayers. Bilayer-coated beads were washed 3× in PBS by sequential centrifugation at 800 rcf and decanting. Beads were resuspended in PBS+0.1% w/v BSA for blocking for 15 minutes rotating at room temperature under foil. 10 nM final concentration of CD19-his8 (Sino Biological, Catalog #11880H08H50) or CD22-his8 (Sino Biological, Catalog #11958H08H50) protein were added to blocked beads and proteins were allowed to bind during a 45 minutes incubation rotating under foil at room temperature. Beads were washed 3× in PBS +0.1% w/v BSA by sequential centrifugation at 300 rcf and decanting. Beads were resuspended in 120 µl PBS+0.1% w/v BSA.

Preparation of CD19 Silica Beads Over a Range of Diameters

Prior building bilayers on Silica beads ranging from 2.5 µm-20 µm in diameter (Microspheres-Nanospheres, Catalog #C-SIO-2.5, 5, 10, 15, 20), beads were RCA cleaned as follows: beads were pelleted at 2000×g in low retention tubes (Eppendorf, Catalog #022431081) and resuspended in acetone. Resuspended beads were sonicated for 60 minutes in a bath sonicator. Rinse and sonication were repeated in ethanol. Finally, rinse and sonication were repeated in water. Beads were then washed 2× in water to remove all traces of ethanol and left in a small volume after decanting. All further steps were performed in a 70-80° C. water bath prepared in a fume hood. Proper Personal Protective Equipment (PPE) was worn throughout the RCA cleaning protocol. Washed beads were added to 3 ml of hot 1.5 M KOH in a clean glass vial suspended in the water bath described above. 1 ml 30% $H_2O_2$ to bead solution and allowed to react for 10 min. Washed beads were cooled on ice, pelleted at 2000×g and rinsed 5× in ultrapure water. Used cleaning solution was saved for disposal by Environmental Health and Safety (EH and S). Cleaned beads were resuspended in 240 μl tissue-culture grade PBS, pH 7.2 (Gibco, Catalog #20012050) and briefly vortexed. The lipid mix used in this assay differed slightly from above. Here a mix of 93.5% POPC (Avanti, Catalog #850457), 5% Ni2+-DGS-NTA (Avanti, Catalog #790404), 1% PEG5000-PE (Avanti, Catalog #880230, and 0.5% atto390-DOPE (ATTO-TEC GmbH, Catalog #AD 390-161. Bilayers were built and proteins coupled as described above. The concentration of CD19 was scaled appropriately to account for the increased surface area of the larger beads.

Bead Engulfment Assay

Twelve to sixteen hours prior to imaging, $2.5 \times 10^4$ J774A.1 macrophages expressing the appropriate CAR-P or control construct were plated in a 96-well glass bottom MatriPlate (Brooks, Catalog #MGB096-1-2-LG-L). To assess engulfment, $0.5 \times 10^6$ CD19 or CD22-ligated beads were added to each well. Engulfment was allowed to proceed for 45 minutes at 37° C. incubator with $CO_2$. Cells were then imaged as described below.

Bites Assay—J774A.1 Macrophage, Dendritic Cell and NIH 3T3 Fibroblasts

On the day of imaging, $0.5 \times 10^6$ NIH 3T3 fibroblasts, dendritic cells or macrophages and 1.5 million Raji B cells were combined in a 1.5 ml Eppendorf tube and pelleted by centrifugation (800 rpm/68×g) for 5 minutes at room temperature. Culture media was decanted to ~100 μl volume and cells were gently resuspended, and allowed to interact in the small volume for 60 minutes in a 37° C. incubator with $CO_2$. After incubation cells and beads were diluted to a final volume of 1000 μl and 300 μl of this co-culture plated for imaging in a 96-well glass bottom MatriPlate (Brooks, Catalog #MGB096-1-2-LG-L), and imaged as described below.

Eating Assay Read by FACS-J774A.1 Macrophage and Raji B Cells 20,000 J774A.1 macrophages were plated into 96-well glass bottom MatriPlate (Brooks, Catalog #MGB096-1-2-LG-L) in a final volume of 300 μl complete DMEM (Gibco, Catalog #11965-092) supplemented with 1×Pen-Strep-Glutamine (Corning, Catalog #30-009 Cl) and 10% fetal bovine serum (FBS) (Atlanta Biologicals, Catalog #511150H). 52 hours prior to reading the assay macrophages were stimulated with 500 ng/ml LPS (Sigma, Catalog #L4516). 44 hours prior to imaging LPS was removed by three sequential gentle washes. After LPS removal 10,000 Rajis expressing mCherry-CAAX were added to the well containing stimulated macrophages. The co-culture was incubated for 44 hours in a 37° C. tissue culture incubator with 5% $CO_2$. After 44 hr, the remaining number of Raji B cells remaining was analyzed by FACS as follows: 10,000 counting beads were added to the well immediately prior to reading and the cell-counting bead mixture was harvested by pipetting up and down 8× with a p200 pipet. The assay was read on an LSRII (BD Biosciences) and Rajis were identified by the presence of mCherry fluorescence.

Primary Cell Transduction and Differentiation

Bone marrow derived macrophages (BMDMs) were produced as previously described (Weischenfeldt and Porse, 2008), except that L-929 conditioned media was replaced with purified 25 ng/ml M-CSF (Peprotech, Catalog #315-02). The BMDMs were lentivirally infected with concentrated lentivirus after 5 days of differentiation. Differentiation was confirmed by F4/80 staining on day seven and found to be >95% efficient for each replicate. Phagocytosis was measured on day nine in imaging media lacking M-CSF.

To produce CAR-P expressing dendritic cells, bone marrow-derived hematopoietic stem cells were lentivirally infected immediately after harvest by spinning with concentrated lentivirus in GMCSF-containing media (IMDM supplemented with 10% FBS and PSG) on retronectin (Clontech, Catalog #T100A)-coated plates at 2200×g for 45 minutes at 37° C. Dendritic cells were produced as previously described (Mayordomo et al., 1995) by culturing bone marrow cells for 8-11 days with GMCSF. IL-4 was added 2-3 days before use. Efficient differentiation into CD11c+ dendritic cells was verified by FACS, revealing >95% APC-CD11c+cells (Biolegend, Catalog #N418).

Antigen Cross-Presentation Assay

The ability of CAR-P to stimulate OTI T cell proliferation was tested using the co-culture assay shown as a schematic in FIGS. 8A-8D and described previously (Roberts et al., 2016). 10,000 CAR-P transduced CD11c+dendritic cells transduced and differentiated as above were plated in U bottom 96 well dishes (Falcon, Catalog #353077) and stimulated with 1 μg/ml LPS. 12 hours after LPS stimulation, 40,000 Raji B cells expressing soluble cytosolic ovalbumin (Raji B-OVA) were added to the culture. 24 hours after Raji B-OVA cell addition, 50,000 OTI CD8+ T cells isolated from lymph nodes of OTI TCR transgenic mice using a CD8+T cell purification kit (Stemcell, Catalog #19853) and labeled with e670 proliferation dye (Thermo Fisher Scientific, Catalog #65-0840-85) were added. 72 hours after OTI addition the percent of OTI cells divided was measured by eFluor670 signal using flow cytometry.

Confocal Imaging

All imaging in this study was performed using a spinning disk confocal microscope with environmental control (Nikon Ti-Eclipse inverted microscope with a Yokogawa spinning disk unit). For bead internalization assays, images were acquired using a 40×0.95 N/A air objective and unbiased live image acquisition was performed using the High Content Screening (HCS) Site Generator plugin in μManager3. Other images were acquired using either a 100×1.49 N/A oil immersion objective. All images were acquired using an Andor iXon EM-CCD camera. The open source μManager software package was used to control the microscope and acquire all images.

Quantification of Whole Cell Internalization 20,000 J774A.1 macrophages were plated into 96-well glass bottom MatriPlate (Brooks, Catalog #MGB096-1-2-LG-L). Four hours prior to imaging, the macrophages were stimulated with 500 ng/ml LPS (Sigma, Catalog #L4516). Immediately prior to imaging the LPS-containing media was replaced with Fluobrite DMEM (Thermo Fisher Scientific, Catalog #A1896701) containing 10% FBS. 40,000 Raji cells were added to the macrophages and the co-culture was imaged at 5 minutes intervals for 12 hr. For the antibody experiments, macrophages were washed into DMEM minus phenol red (A14430-01) containing 10% FBS just prior to addition of 40,000 Raji cells. Where indicated antibody was added to a final concentration of 20 μg/ml immediately after Raji cell addition and prior to imaging in order to limit antibody internalization. Because cells moved in and out of the field of view, only cells present after 8 hours of imaging were selected and quantified their B cell eating if they could be followed for four hours or more. Time-lapse analysis was used to ensure that the B cell appeared viable prior to engulfment by the macrophage. Engulfment of B cells with an apoptotic morphology was not counted as a whole cell eating event.

Quantification of Bite Internalization

During live cell image acquisition GFP-positive J774A.1 macrophages or NIH 3T3 cells were selected by the presence of GFP signal. A full z-stack including the entire cell was captured using 1 µm steps. All z sections were then manually inspected for internalized Raji B cell material. Cells containing one or more bites of fully internalized Raji B cell material >1 µm in diameter were scored as positive.

Liposome FRET Assay

Experiments were carried out as previously described (Alvey C M et al., Current Biology 27:2065-2077, 2017). Briefly, proteins were purified using a bacterial expression system. All protein components (1 mg/ml BSA, 100 nM tSH2-Syk SNAP-505, 0 to 500 nM His10-CD3ζ or His10-FcRγ intracellular chain, and 7.2 nM His10-Lck Y505F) were mixed into kinase buffer (50 mM HEPES-NaOH pH 6.8, 150 mM NaCl, 10 mM $MgCl_2$, and 1 mM TCEP). Liposomes prepared at the following molar ratios: 74.5% POPC (Avanti, Catalog #850457C), 10% DOGS-NTA (Nickel) (Avanti, Catalog #790404C, 0.5% Rhodamine PE (Avanti, Catalog #810150C), and 15% DOPS (Avanti, Catalog #840035C) were added and the mixture was incubated for 40-60 minutes at room temperature, during which the SNAP-505 fluorescence was monitored at 8 s intervals with 504 nm excitation and 540 nm emission. 1 mM ATP was then injected to trigger Lck mediated phosphorylation of CD3ζ t or FcRγ. Injection was followed by 5 seconds of automatic shaking of the plate, and the fluorescence was further monitored at 8 s intervals for at least 1 hr. Data were normalized by setting the average fluorescence value of the last 10 data points before ATP addition as 100% and background fluorescence as 0%. The final extent of fluorescence quenching (% fluorescence change) at each concentration of receptor was determined using the average of the last 20 data points after ensuring fully equilibrated binding. Nine reactions containing increasing concentrations of CD3ζ and nine reactions containing increasing concentrations of FcRγ were run in parallel. The final % fluorescence change was plotted against FcRγ or CD3ζ concentration. The apparent dissociation constants (Kd) of tSH2-Syk to FcRγ and CD3ζ were calculated by fitting the data with Graphpad Prism 6.0, using the "one site specific binding" model.

Protein Expression, Purification, and Labeling

The intracellular portion of the FcRγ-chain (amino acid residues (aa) 45-85, Human FcRγ, Uniprot FCERG HUMAN) was cloned into a modified pET28a vector containing a His10 upstream to the multiple cloning site using BamHI and EcoRI. The intracellular portion of CD3ζ (aa 52-164, Human CD3ζ, Uniprot CD3Z HUMAN) was also cloned into the His10 modified pET28a vector. A Lys-Cys-Lys-Lys sequence, originally present for fluorescent labeling, is also present between His10 and CD3ζ in this construct. SNAP-tSH2Syk (aa 1-262) was cloned into a pGEX6 vector using BamHI and EcoRI. His10-CD3ζ, His10-FcRγ-chain, and GST-SNAP-tSH2Syk were bacterially expressed in BL21 (DE3) RIPL strain of *Escherichia coli* as described previously (Alvey C M et al. 2017, supra). His10-Lck Y505F was expressed in SF9 cells using the Bac-to-Bac baculovirus system as described previously (Alvey C M et al., 2017). All cells were lysed in an Avestin Emulsiflex system. His10 proteins were purified by using Ni-NTA agarose (Qiagen, Catalog #30230) and GST-SNAP-tSH2Syk was purified by using glutathione-Sepharose beads (GE Healthcare, Catalog #17075601) as described previously (Alvey C M et al. 2017, supra). Soluble SNAP-tSH2 Syk was generated by cleaving the GST moiety via the PreScission Protease at 4° C. overnight. All proteins were subjected to gel-filtration chromatography using a Superdex 200 10/300 GL column (GE Healthcare, Catalog #17517501) in HEPES-buffered saline (HBS) containing 50 mM HEPES-NaOH (pH 6.8 for His10-CD3ζ, His10-FcR γ-chain, and GST-SNAP-tSH2Syk and pH 7.4 for His10-Lck Y505F), 150 mM NaCl, 5% glycerol, and 1 mM TCEP. The monomer fractions were pooled, frozen in liquid nitrogen and stored at −80° C. All gel-filtered proteins were quantified by SDS-PAGE and Coomassie staining, using BSA as a standard. To prepare fluorescently labeled tSH2 Syk, 10 µM SNAP-tSH2 Syk was incubated at a 1:2 ratio with SNAP-Cell 505-Star (NEB, Catalog #S9103S) overnight at 4° C. and run over a PD MiniTrap G-25 (GE Healthcare, Catalog #28-9225-29 AB) column to eliminate excess dye.

Phosphotyrosine and Phalloidin Staining

To fix and stain preparations described above in bead and bites assays for quantifying enrichment of phosphotyrosine staining, half the media (~150 µl) was gently removed from the imaging well and replaced with 150 µl 6.4% paraformaldehyde solution (prepared from 32% stock, Electron Microscopy Sciences, Catalog #50980495) in tissue culture grade PBS, pH7.2 (Gibco, Catalog #20012050). Cells were fixed for 15 minutes in a 37° C. incubator with $CO_2$. After fixation cells were washed 2× with PBS and permeabilized/blocked for 60 minutes at room temperature in freshly prepared, filter sterilized PBS+5% FBS+0.1% w/v saponin (PFS solution). After permeabilization, cells were washed 2×3 minutes with PFS solution. Following block, cells were incubated with 1:100 dilution of mouse anti-phosphotyrosine (pTyr) antibody to stain pan-pTyr (Santa Cruz, Catalog #PY20) diluted in PFS solution in the dark for 60 minutes at room temperature then washed 3×5 minutes in PFS solution. Washed cells were incubated with a 1:500 dilution of goat anti-mouse Alexa Fluor 647 antibody (Thermo Fisher Scientific/Molecular Probes, Catalog #A21236) in PFS solution in the dark for 60 minutes at room temperature. Wells were then washed 3×5 minutes in PFS solution. Cells were covered in 200 µl PBS. If not imaged immediately samples were wrapped in parafilm and foil and stored at 4° C. prior to microscopy. Phosphotyrosine enrichment at the synapse was calculated by dividing the mean Alexa Fluor 647 signal of a 5 pixel linescan at the synapse with bead or cell by a 5 pixel linescan on the cortex. For phalloidin staining, cells were fixed with 4% PFA for 15 minutes at room temperature, blocked and permeabilized with 5% BSA in TBS with 0.5% Triton X overnight, and incubated with AlexaFluor 647 Phalloidin (Thermo Fisher Scientific/Molecular Probes, Catalog #A22284) for 20 min. Cells were then washed with PBS, imaged and quantified using the method described above. Each data point represents a single cell, and the graphs reflect pooled results from three biological replicates.

Ovalbumin Antibody Staining

To fix and stain preparations described above for ovalbumin staining, half the media (~150 µl) was gently removed from the imaging well and replaced with 150 µl 8% paraformaldehyde solution (prepared from 32% stock, Electron Microscopy Sciences, Catalog #50980495) in tissue culture grade PBS, pH7.2 (Gibco, Catalog #20012050). Cells were fixed for 10 minutes in a 37° C. incubator with $CO_2$. After fixation cells were washed 2× with PBS and permeabilized/blocked for 60 minutes at room temperature in freshly prepared, filter sterilized PBS+0.1% w/v casein+ 0.1% w/v saponin (PCS solution). After permeabilization, cells were washed 1×3 minutes with PCS solution and blocked for 1 hour at room temperature in PCS. Following block, cells were incubated with 1:100 dilution of rabbit anti-ovalbumin (OVA) antibody to stain OVA (Thermo Fisher Scientific/Pierce, Catalog #PA1-196) diluted in PCS solution overnight at 4° C. Washed cells were incubated with a 1:200 dilution of goat anti-rabbit Alexa Fluor 647 antibody (Thermo Fisher Scientific/Molecular Probes, Catalog #A21235) and 3.3 nM 488 phallodin (dissolved at 6.6 µM in methanol) in PCS solution in the dark for 60 minutes at room temperature. Wells were then washed 3×5 minutes in PCS solution. Cells were covered in 200 µl PBS and immediately imaged. Ovalbumin signal was quantified as the corrected total cell fluorescence (CTCF). CTCF=Integrated Density −Area of Selected Cell*Mean Fluorescence of 3 Background Readings. Each data point represents a single cell, and the graphs reflect pooled results from three biological replicates.

Image Processing and Analysis

All image quantification was done on raw, unedited images. All images in figures were first analyzed in ImageJ, where a single Z-slice at the center of the cell was extracted. The image intensities were scaled to enhance contrast and cropped in Photoshop. For movies, background was subtracted in Fiji using a rolling ball radius of 50 µm and bleach corrected using the Histogram Matching plug in.

Statistics

All statistical analysis was performed in Prism 6.0 (GraphPad, Inc.). The statistical test used is indicated in each figure legend. Error bars throughout the paper denote 95% confidence intervals of the mean. * indicates p<0.0001;  indicates p<0.001 and * indicates p<0.01.

Example 2

Results

To program engulfment towards a target antigen, a CAR strategy was created using the CAR-T design as a guide (Fesnak et al., 2016). This new class of synthetic receptors is termed "Chimeric Antigen Receptors for Phagocytosis" (CAR-Ps). The CAR-P molecules contain the extracellular single-chain antibody variable fragment (scFv) recognizing the B cell antigen CD19 (αCD19) and the CD8 transmembrane domain present in the αCD19 CAR-T (Fesnak et al., 2016; Kochenderfer et al., 2009). To identify cytoplasmic domains capable of promoting phagocytosis, a screen was performed on a library of known murine phagocytic receptors: Megf10 (FIG. 1A), the common γ subunit of Fc receptors (FcRγ), Bai1, and MerTK (Penberthy and Ravichandran, 2016). FcR triggers engulfment of antibody-bound particles, while the other receptors recognize apoptotic corpses (Freeman and Grinstein, 2014; Penberthy and Ravichandran, 2016). A receptor containing an extracellular αCD19 antibody fragment and a cytoplasmic GFP, but no signaling domain, as constructed to test whether adhesion mediated by the αCD19 antibody fragment is sufficient to induce engulfment (FIG. 1A; CAR-P$^{GFP}$).

Figure 1B:
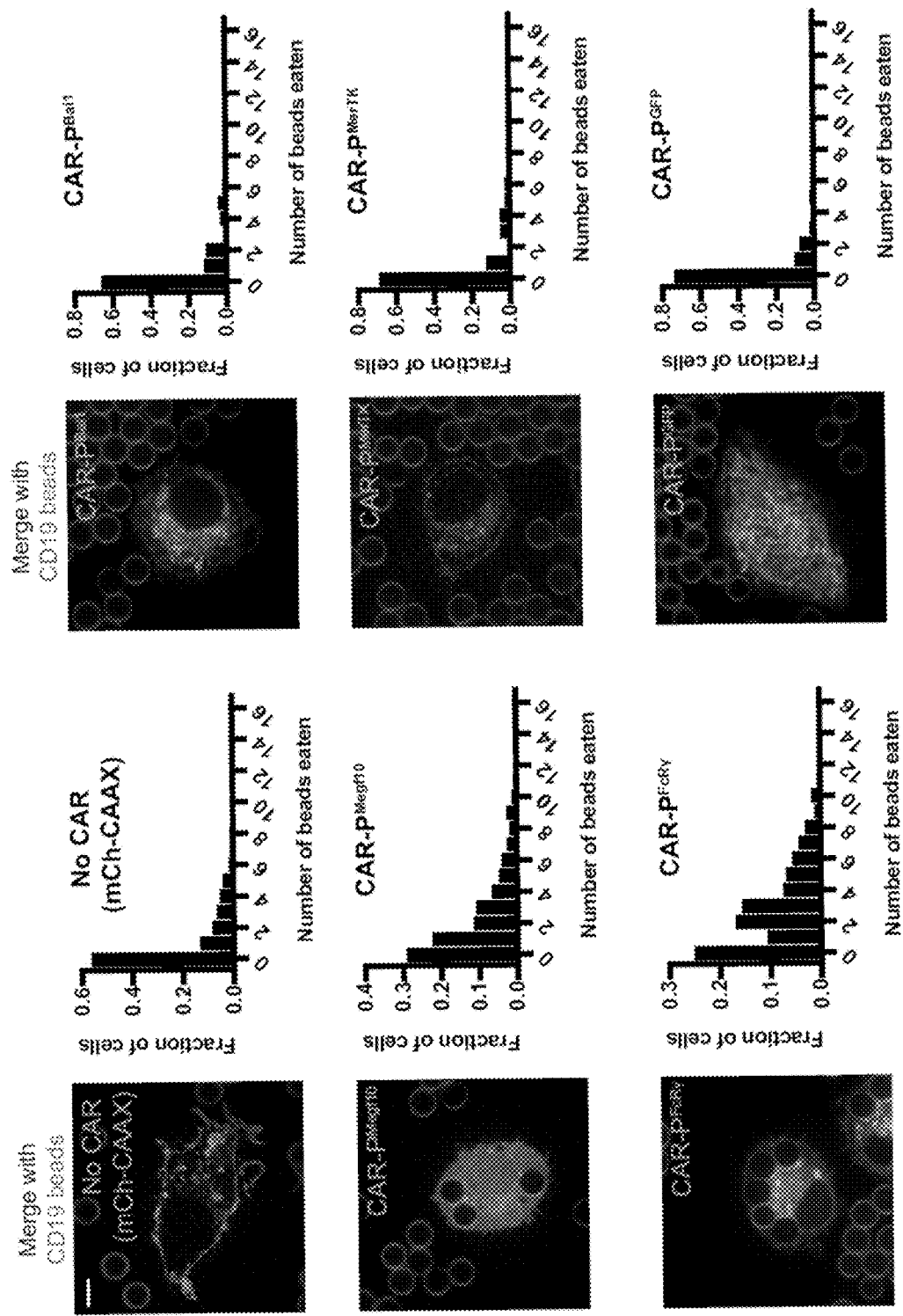
Figure 1C:
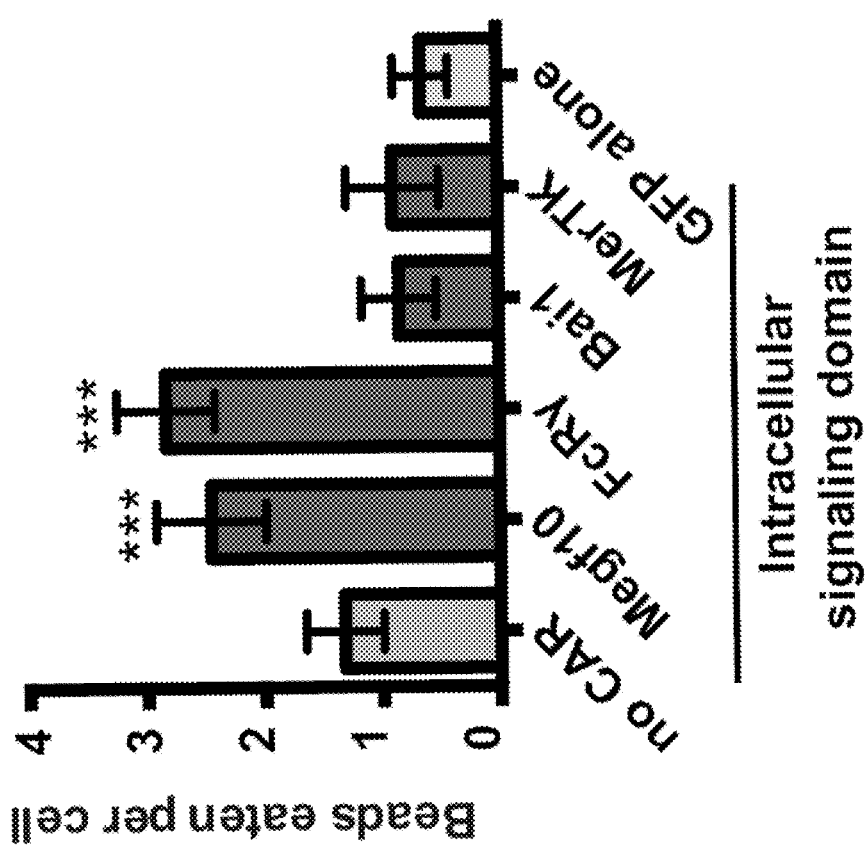

To assay the library of CAR-Ps, each CAR-P was introduced into J774A.1 murine macrophages by lentiviral infection. As an engulfment target, 5 µm diameter silica beads coated with a supported lipid bilayer was used. A His8-tagged extracellular domain of CD19 was bound to a NiNTA-lipid incorporated into the supported lipid bilayers. Macrophages expressing a CAR-P with the Megf10)(CAR-P$^{Megf10}$ or FcRγ (CAR-P$^{FcRγ}$) intracellular domain promoted significant engulfment of CD19 beads compared to macrophages with no CAR (FIGS. 1B-1C). A video clip showing a non-limiting example of engulfment of silica beads by a modified macrophage was also taken to show that a macrophage infected with αCD19 CAR-P$^{Megf10}$ engulfed 5 µm silica beads coated in a supported lipid bilayer (labeled with atto647) and ligated to His-tagged CD19 extracellular domain ((also see, FIG. 1—Supplemental Video 1 of Morrissey et al., 2018). The field of view used for this video clip was 43×43 µm. The video clip is a maximum intensity projection of 17 z-planes acquired at 0.5 µm intervals. Z-stacks were acquired every 30 seconds for 30 minutes. Images were acquired every 20 seconds for 30 minutes and time is indicated in the bottom right.

Figure 1D:
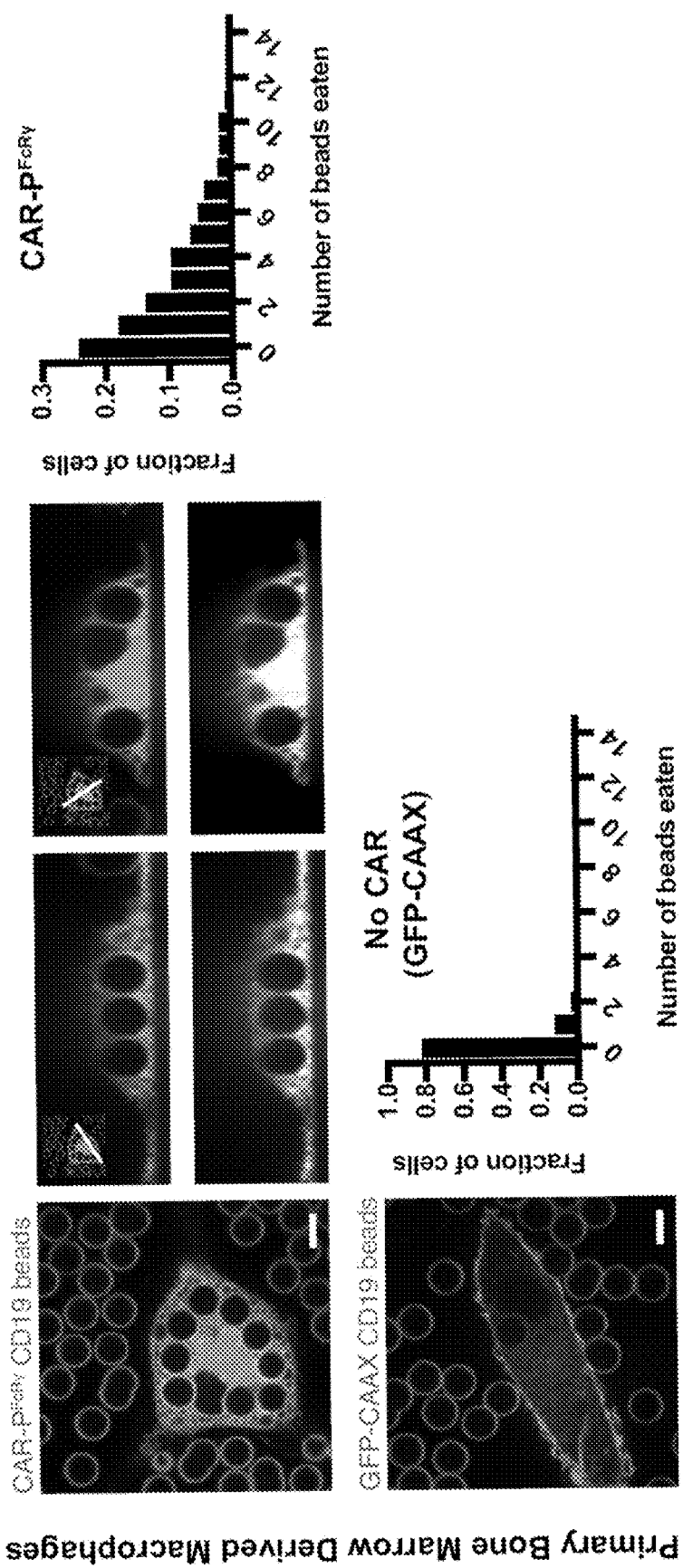
Figure 1E:
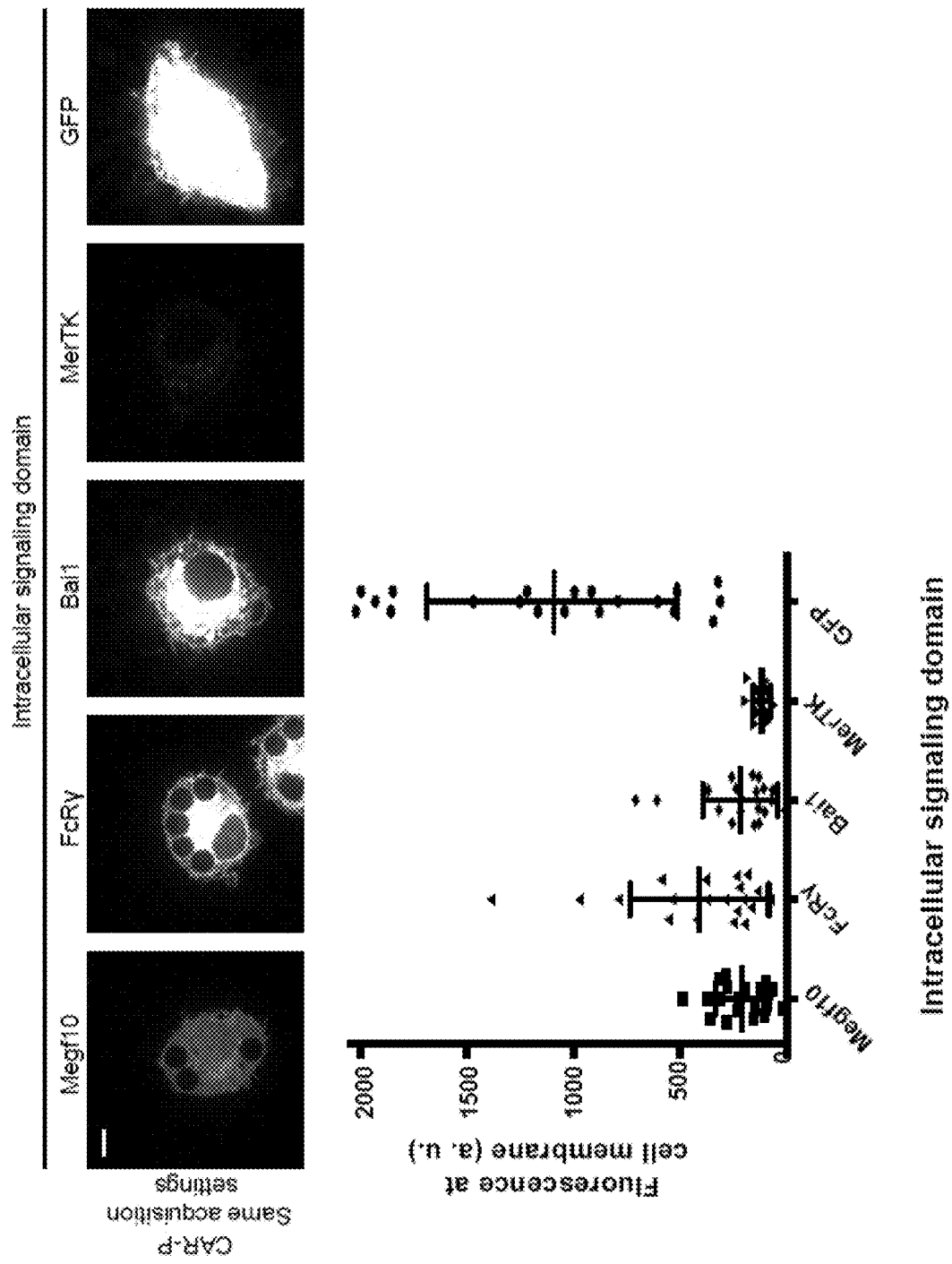

Macrophages expressing CAR-P$^{Bai1}$, CAR-P$^{MerTK}$, and the adhesion-only CAR-P$^{GFP}$ did not bind the CD19 beads even though these CAR-Ps are present at the cell surface (FIGS. 1B-1C and 1E). To confirm that the CAR-P was a viable strategy for redirecting primary macrophages, the CAR-P$^{FcRγ}$ was expressed in BMDMs and found that these transfected primary cells also were able to trigger engulfment of CD19 beads (FIG. 1D).

Figure 2A:
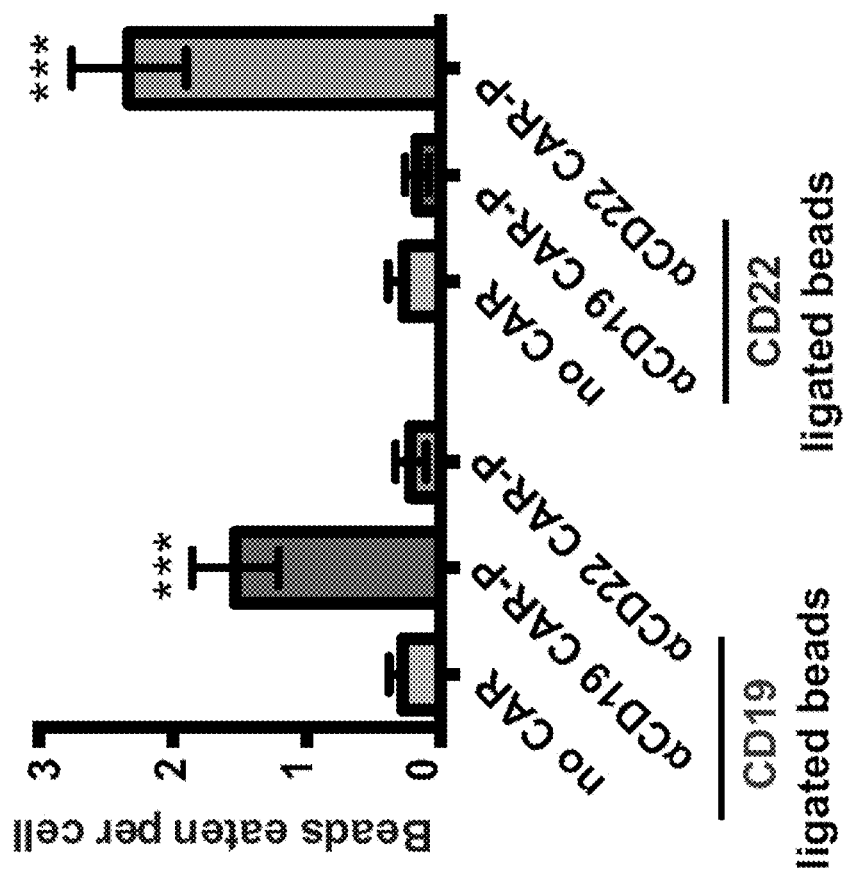
FIGS. 2A-2B illustrate a non-limiting example of specific engulfment of diverse beads driven by CAR-P expression.

The following experiments was performed to determine if the CAR-P strategy could target a different antigen. Because CAR-P$^{Megf10}$ performed well in the initial screen as described in FIG. 1A above, an αCD22 CAR-P$^{Megf10}$ was developed using a previously developed αCD22 antibody fragment (Xiao et al., 2009; Haso et al., 2013). Consistent with the results using αCD19-based CARs, it was observed that αCD22 CAR-P$^{Megf10}$ promoted engulfment of CD22 beads (FIG. 2A). To confirm antigen specificity of CAR-P, αCD19 CAR-P$^{Megf10}$ macrophages were incubated with CD22 beads, and αCD22 CAR-P$^{Megf10}$ macrophages with CD19 beads. CD19 beads were not eaten by αCD22 CAR-P$^{Megf10}$ macrophages, and CD22 beads were not eaten by αCD19 CAR-P$^{Megf10}$ macrophages (FIG. 2A). These data indicate that CAR-P$^{Megf10}$ specifically triggers engulfment in response to the target ligand and that the CAR-P strategy is able to target multiple cancer antigens.

Figure 2B:
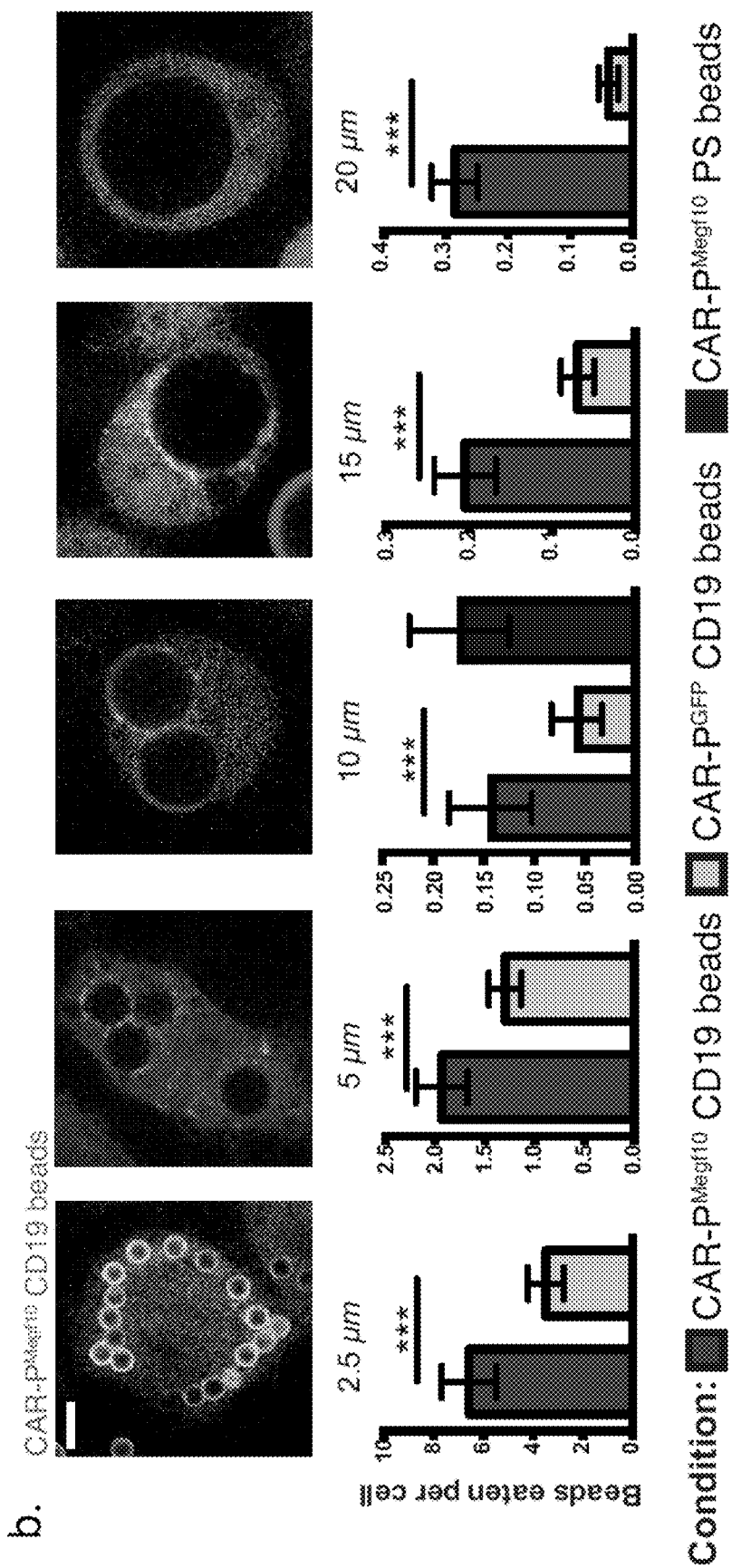

To further define the capabilities of the CAR-P, the capacity of CAR-P-expressing macrophages to engulf variably sized targets was assessed. It was found that CAR-P$^{Megf10}$ was able to trigger specific engulfment of beads ranging from 2.5 µm to 20 µm in diameter, with higher specificity above background engulfment being demonstrated for the larger beads (FIG. 2B). The high background in this assay is due to heterogeneity in the bilayers on beads purchased from a different manufacturer (Corpuscular) than previous assays. For the 10 µm bead condition, the phagocytic efficiency of beads containing the endogenous Megf10 ligand, phosphatidylserine was also tested. It was found that CAR-P$^{Megf10}$ macrophages engulfed CD19 beads and beads containing 10% phosphatidylserine and the adhesion molecule ICAM-1 at a similar frequency (FIG. 2B). This indicates that the CAR-P is comparably efficient to the endogenous system.

Figure 3A:
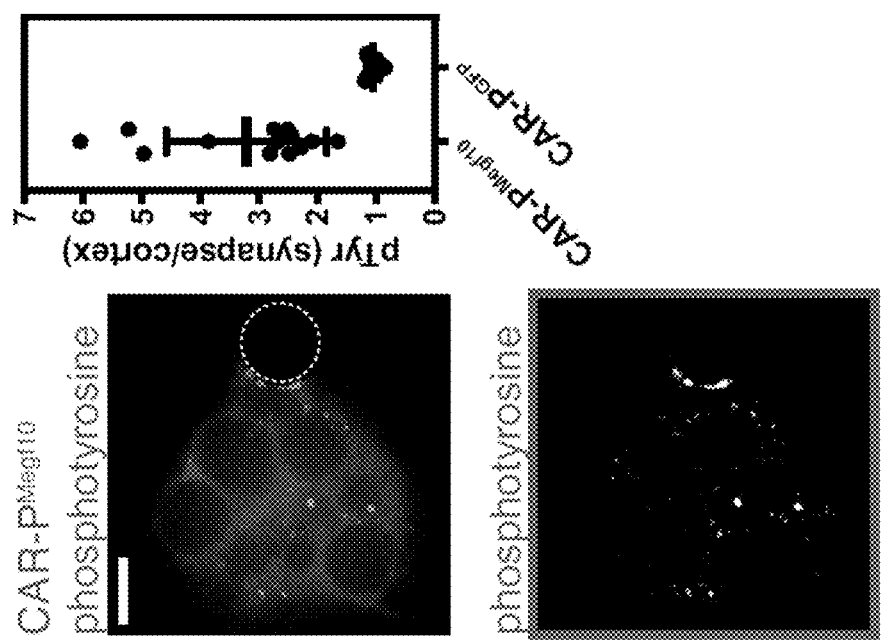
FIGS. 3A-3E illustrate a non-limiting example of engulfment driven by phosphorylated ITAM at the cell-target synapse.
Figure 3B:
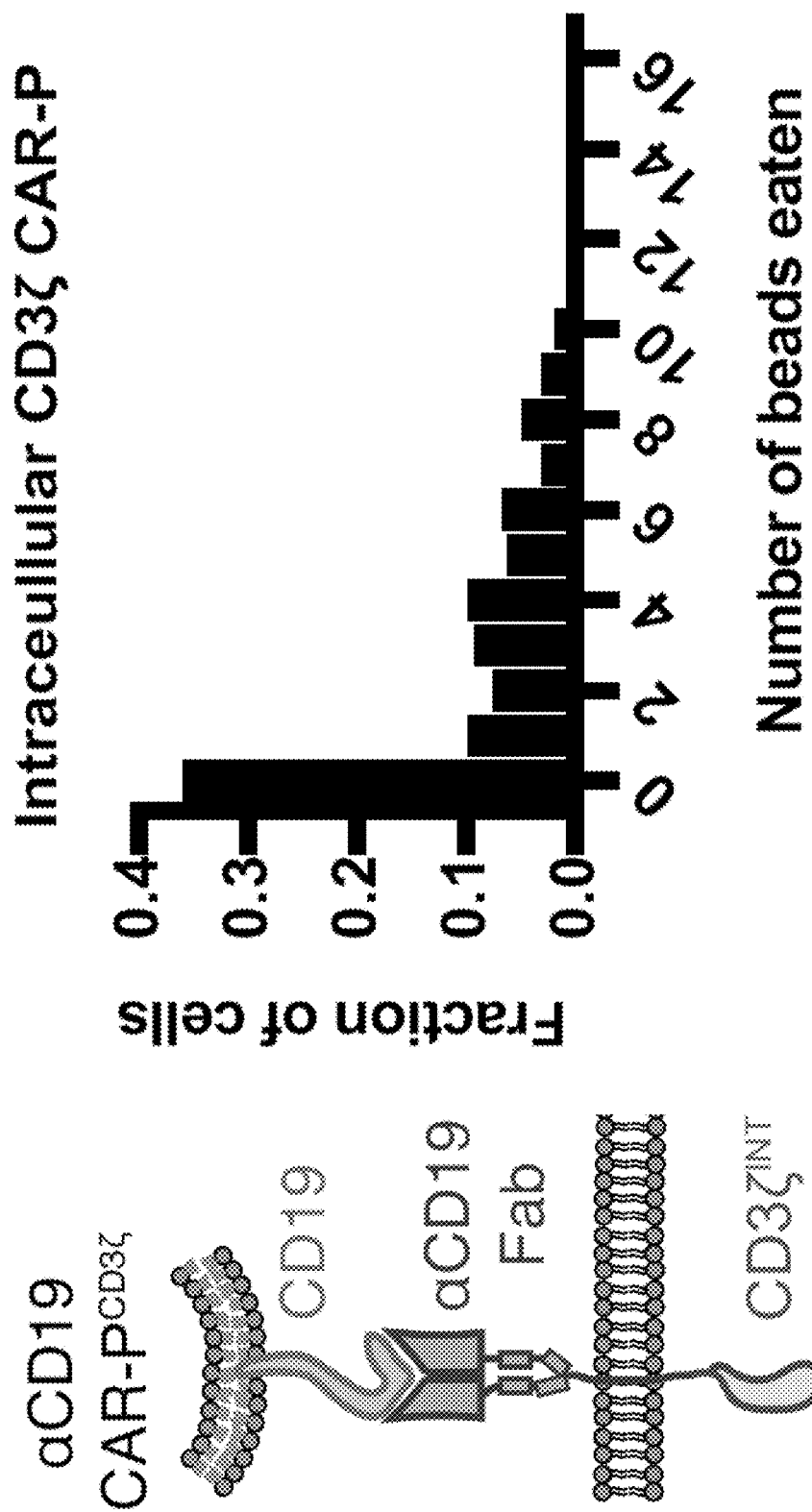
Figure 3C:
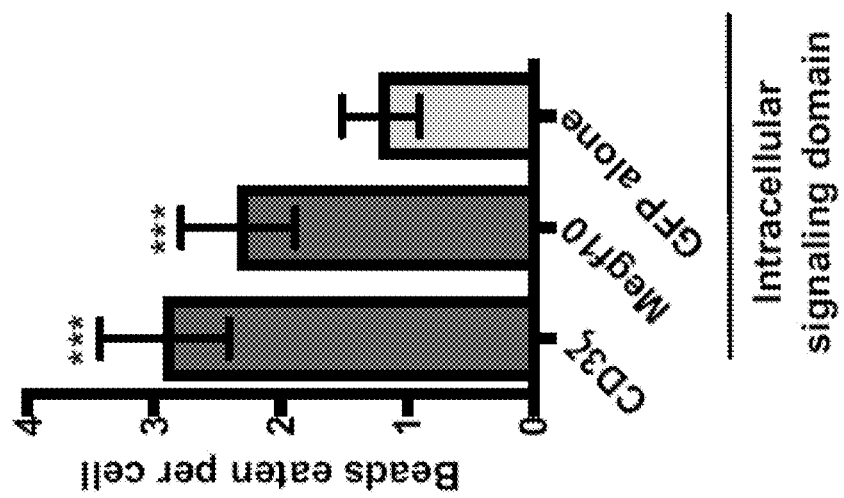
Figure 3D:
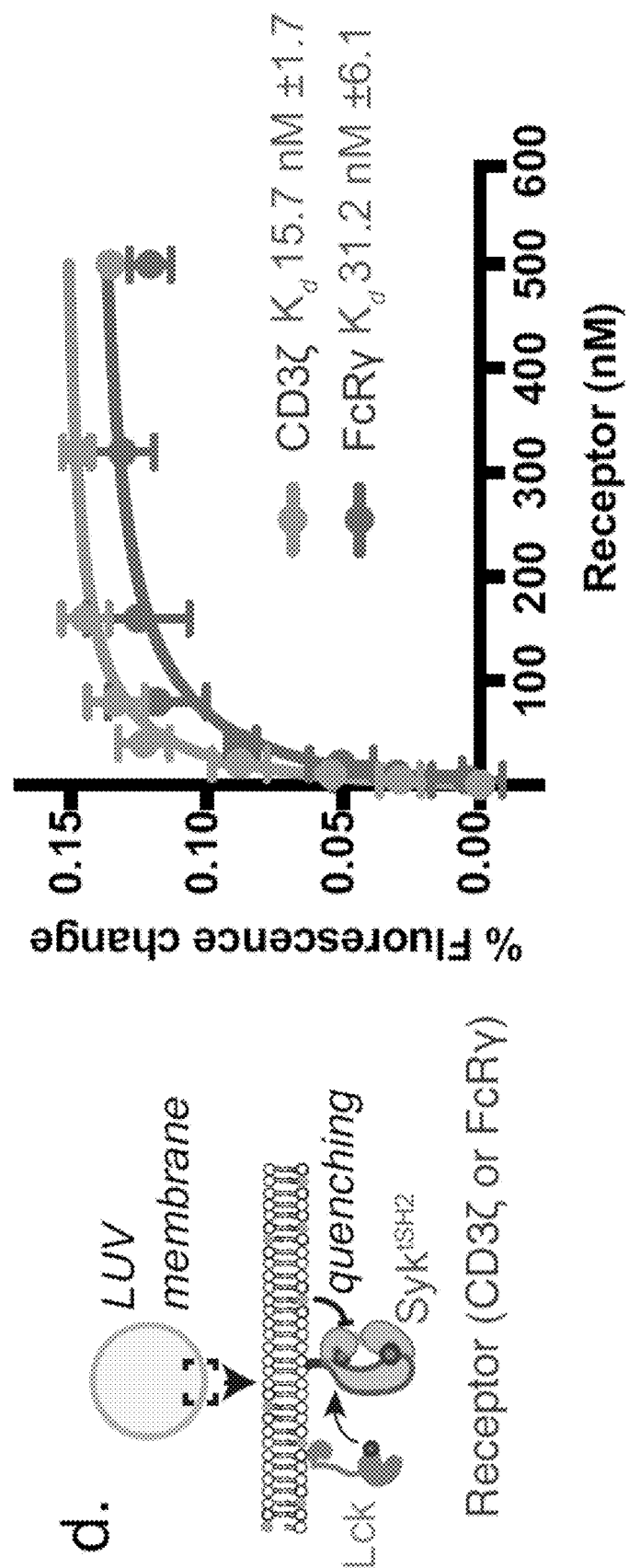
Figure 3E:
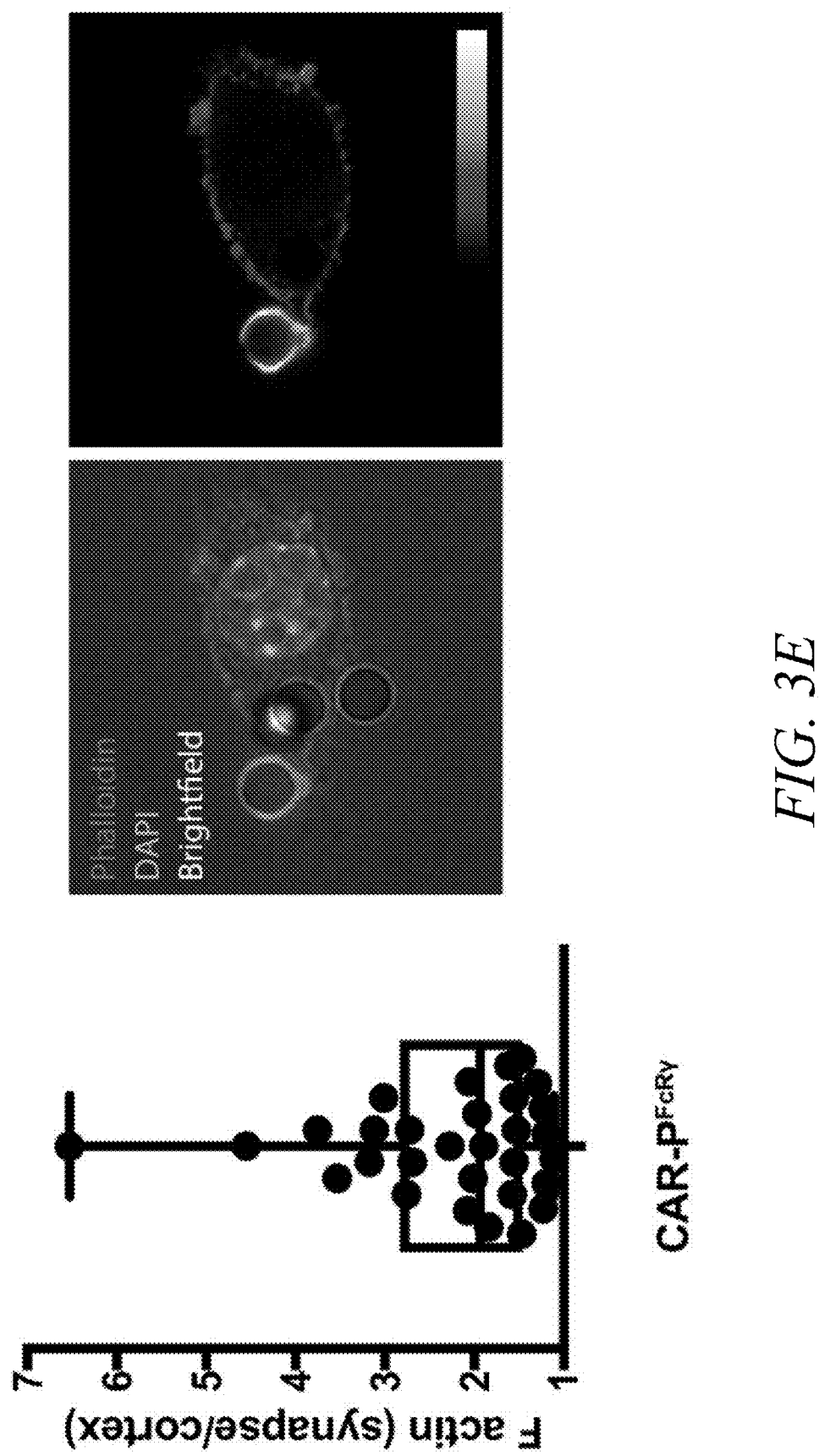

To determine if the CAR-P$^{Megf10}$ initiates active signaling at the synapse between the macrophage and target, a phosphotyrosine staining experiment was conducted. Macrophages expressing CAR-P$^{Megf10}$ exhibited an increase in phosphotyrosine at the synapse, while macrophages expressing CAR-P$^{GFP}$ did not show this enrichment (FIG. 3A). Consistent with previous reports, it was found that F-actin also was enriched at the cell bead synapse (FIG. 3E). Without being bound to any particular theory, this result suggests that CAR-P$^{Megf10}$ initiates engulfment through a localized signaling cascade involving tyrosine phosphorylation.

Both successful CAR-P intracellular domains (from FcRγ and Megf10) have cytosolic Immunoreceptor Tyrosine-based Activation Motifs (ITAMs) that are phosphorylated by Src family kinases. Without being bound to any particular theory, it was hypothesized, based on this observation, that the expression of an alternate ITAM-containing receptor might initiate phagocytosis when expressed in macrophages. The CD3ζ subunit of the T cell receptor contains three ITAM motifs. To test if the CD3ζ chain was able to activate phagocytic signaling, macrophages with the first generation CAR-T were transduced (FIG. 3B). The CAR-T was able to trigger engulfment of CD19 beads to a comparable extent as CAR-P$^{Megf10}$ (FIG. 3C). In T cells, phosphorylated ITAMs in CD3ζ bind to tandem SH2 domains (tSH2) in the kinase ZAP70. Zap70 is not expressed in macrophages, but Syk, a phagocytic signaling effector and tSH2 domain containing protein, is expressed at high levels (Andreu et al., 2017). Previous work suggested that Syk kinase can also bind to the CD3ζ ITAMs (Bu et al., 1995), indicating that the CAR-T may promote engulfment through a similar mechanism as CAR-P$^{FcR\gamma}$. To quantitatively compare the interaction between SyktSH2 and CD3ζ or FcRγ in a membrane proximal system recapitulating physiological geometry, a liposome-based assay was used (FIG. 3D [Hui and Vale, 2014]). In this system, His10-CD3ζ and His10-Lck (the kinase that phosphorylates CD3) are bound to a liposome via NiNTA-lipids and the binding of labeled tandem SH2 domains to phosphorylated CD3ζ was measured using fluorescence quenching. The results described herein demonstrate that Syk-tSH2 binds the CD3ζ and FcRγ with comparable affinity (~15 nM and ~30 nM respectively, FIG. 3D). Collectively, these results demonstrate that the TCR CD3ζ chain can promote phagocytosis in a CAR-P, likely through the recruitment of Syk kinase.

Figure 4A:
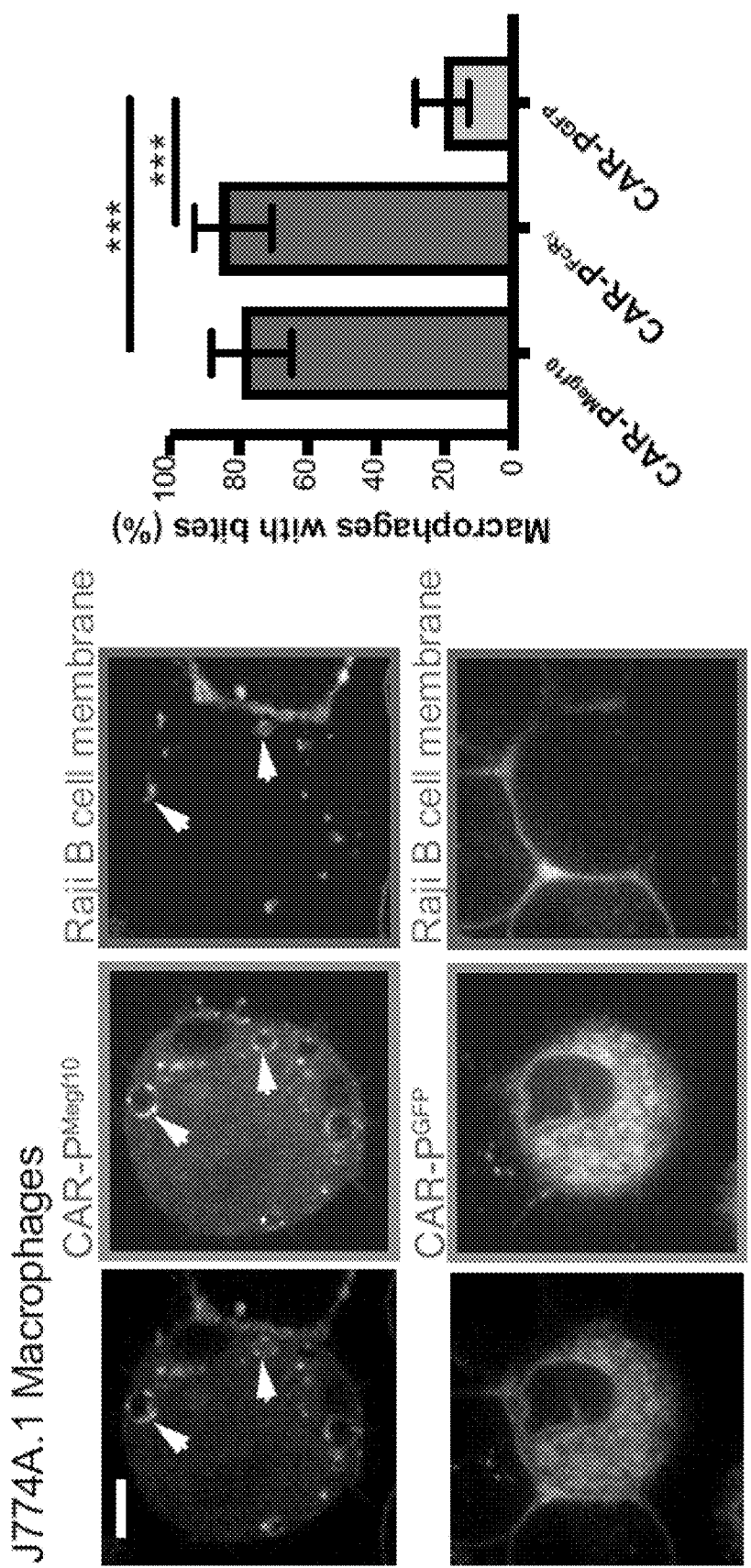
FIGS. 4A-4F illustrate a non-limiting example of CAR-P promoting trogocytosis and whole cell eating.
Figure 4B:
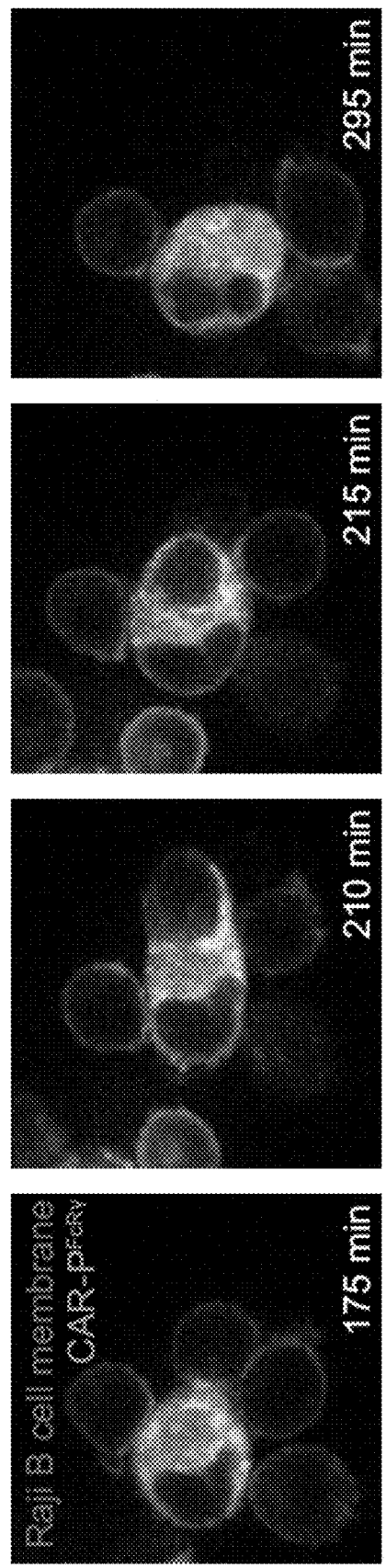
Figure 4C:
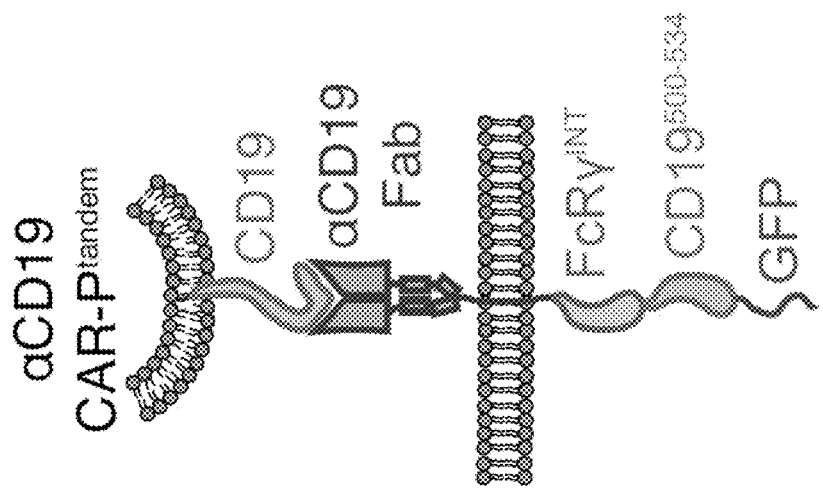

Additional experiments were performed to program engulfment towards a cellular target. In these experiments, the CAR-P$^{Megf10}$ and CAR-P$^{FcR\gamma}$ macrophages were incubated with cancerous Raji B cells that express high levels of endogenous CD19. Strikingly, the majority of CAR-P-expressing macrophages internalized bites of the target cell (FIG. 4A), 78% of CAR-P$^{Megf10}$ and 85% of CAR-P$^{FcR\gamma}$ macrophages internalized bites within 90 min). The biting phenotype resembles trogocytosis, or nibbling of live cells, which has been reported previously in immune cells (Joly and Hudrisier, 2003). This process was dependent on the ITAM-bearing intracellular signaling domain, as removing the signaling domain (CAR-P$^{GFP}$) dramatically reduced trogocytosis (FIG. 4A). A video clip showing the engagement of modified macrophage with Raji B cell was taken and described in Morrissey et al. (ELife, June 4; 7, 2018; see FIG. 4—Supplemental Video 1), which is hereby incorporated by referenced in its entirety. This video clip shows that a macrophage infected with αCD19 CAR-P$^{Megf10}$ engaged with a Raji B cell (labeled with mCherry-CAAX). The field of view used for this video clip was 43×43 μm. The video clip was a maximum intensity projection of 7 z-planes acquired at 1 μm intervals. Images were acquired every 20 seconds for 30 minutes. Images were acquired every 20 seconds for 30 minutes and time is indicated in the bottom right.

Figure 5:
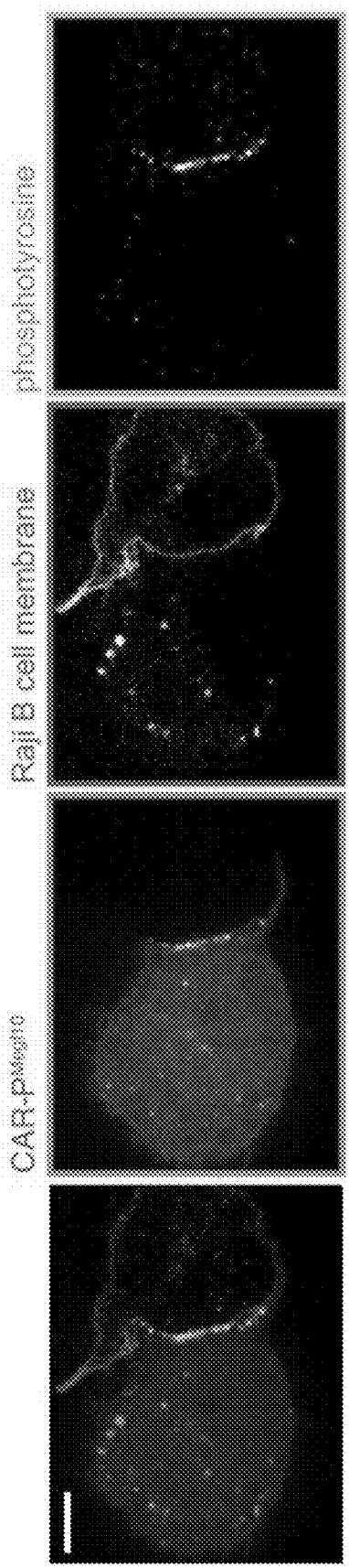
FIG. 5 pictorially summarizes the results of experiments performed to demonstrate that CAR-P localizes with pTyr at synapse with Raji B cell. Phosphotyrosine staining (teal) of macrophages expressing CAR-P$^{Megf10}$ in contact with Raji B cells (cell membrane visualized with mCherry-CAAX. Below, the enrichment at the synapse is quantified as the mean intensity of a five pixel width linescan at the synapse divided by the mean intensity at the adjacent cell cortex for at least 11 sites of contact. Each dot represents one cell-cell synapse, lines represent the mean±one standard deviation, and the graph is the pooled results of three biological replicates. The scale bar indicates 5 μm.
Figure 5:
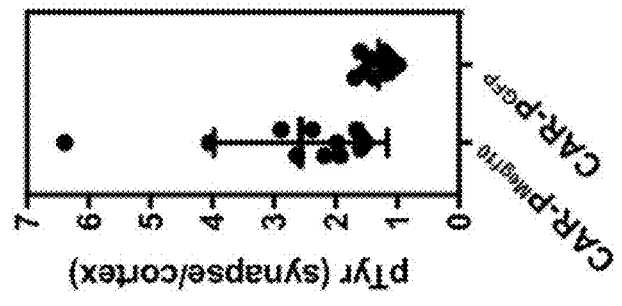
Figure 6:
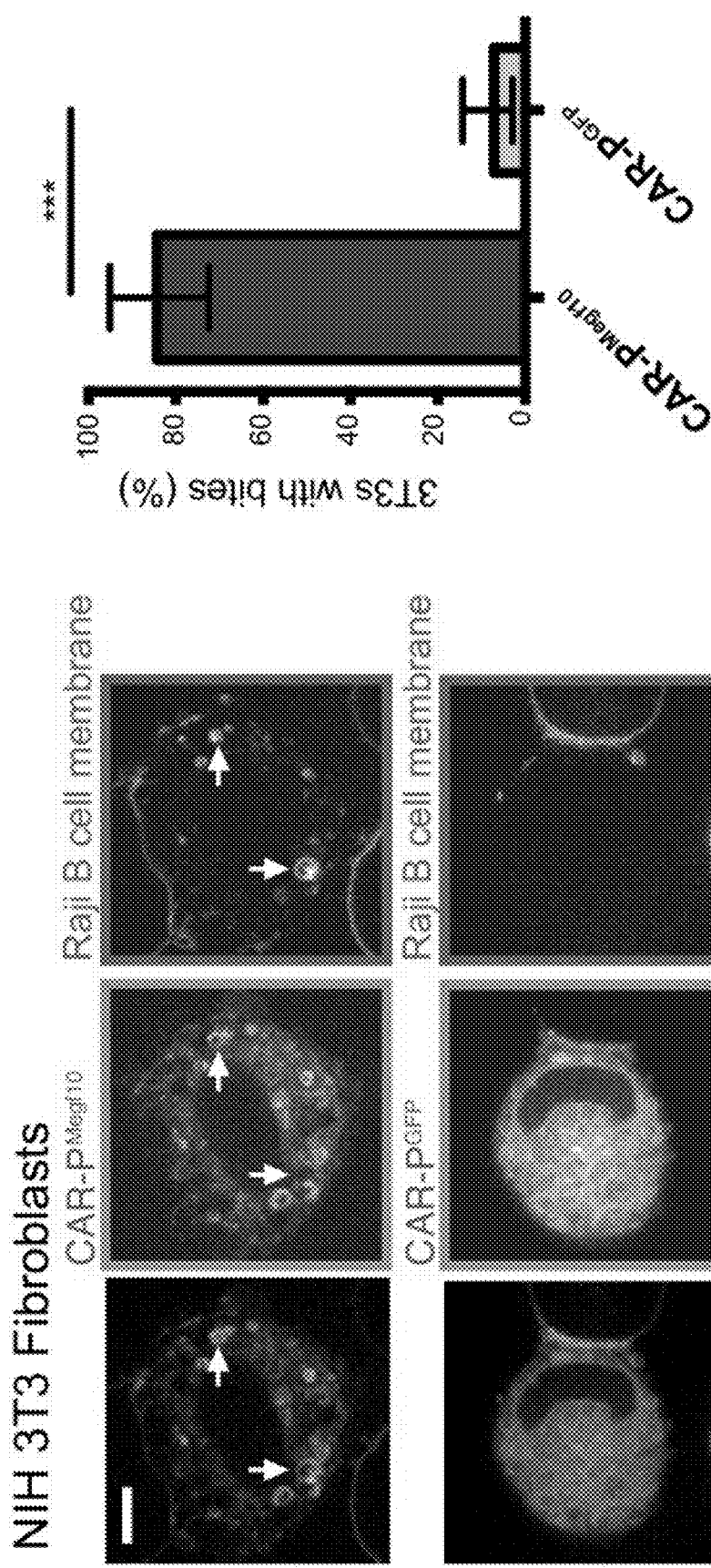
FIG. 6 pictorially summarizes the results of experiments demonstrating that NIH 3T3 cells internalize Raji B cell bites. NIH 3T3 cells expressing the αCD19 CAR-P$^{Megf10}$ (left; greyscale, center) engulf pieces of CD19+Raji B cells (labeled with mCherry-CAAX; magenta in merge, left; greyscale, right). The control αCD19 CAR-P$^{GFP}$-infected 3T3s are shown below. Arrows point to pieces of ingested Raji B cell. The proportion of cells taking at least one bite after 90 minutes co-incubation is graphed on the left (graphs show the pooled data of three separate experiments; n=111 CAR-P$^{Megf10}$3T3 cells and 121 CAR-P$^{GFP}$ 3T3; *** indicates p<0.0001 by two-tailed Fisher Exact Test; error bars denote 95% confidence intervals). Bites are defined as a fully internalized piece of mCherry-labeled material >1 μm in diameter.

Enrichment of phosphotyrosine at the cell-cell synapse further supports active signaling initiating trogocytosis (see, e.g., FIG. 5). The CAR-P module also was able to induce trogocytosis in non-professional phagocytes, human NIH 3T3 fibroblast cells (see, e.g., FIG. 6). This suggests that the CAR-P can promote cancer antigen-dependent engulfment by both professional and non-professional phagocytes.

The next focus involved engineering strategies to engulf whole human cancer cells. It was observed that macrophages expressing the CAR-P$^{Megf10}$ or CAR-P$^{FcR\gamma}$ were capable of engulfing whole Raji B cells (2 cancer cells eaten per 100 macrophages in a 4-8 hours window for both CAR-P$^{Megf10}$ or CAR-P$^{FcR\gamma}$) (see, FIGS. 4B and 4E). A video clip showing the engagement of modified macrophage with Raji B cell was taken and described in Morrissey et al., 2018, supra (see FIG. 4—Supplemental Video 2). This video clip shows that a macrophage infected with αCD19 CAR-P$^{FcR\gamma}$ engaged with a Raji B cell (labeled with mCherry-CAAX). The field of view used for this video clip was 53×53 μm. Images were acquired every 5 minutes. Time is indicated in the bottom right.

Figure 7:
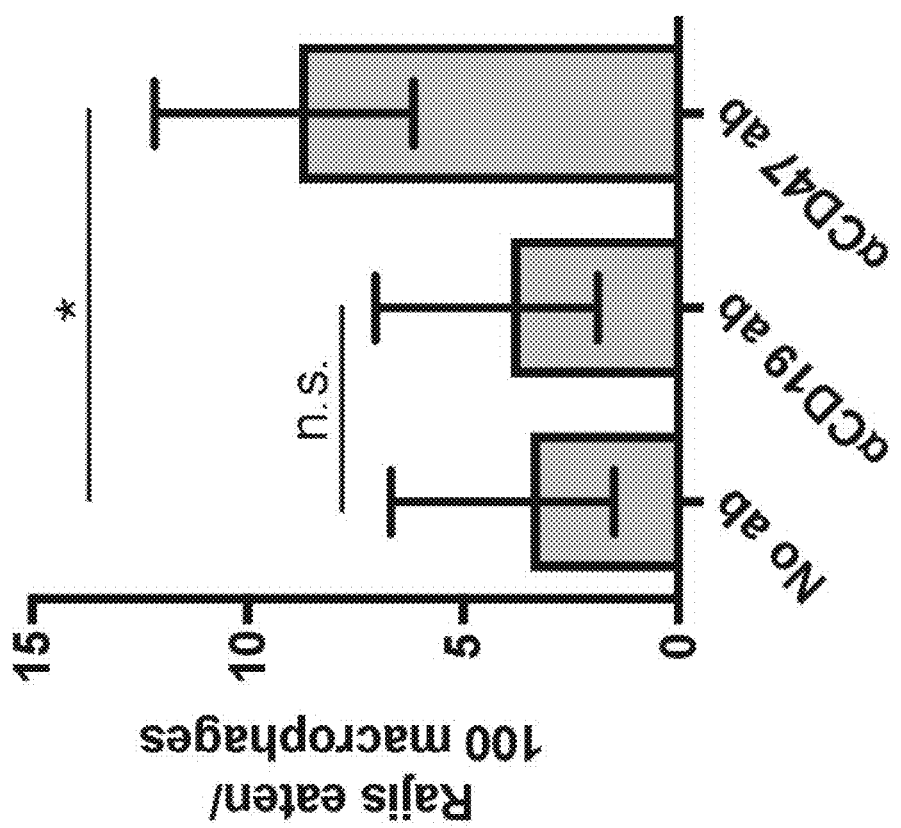
FIG. 7 graphically summarizes the results of experiments showing that opsonization by an anti-CD47 antibody enhances whole cell internalization through CAR-P Macrophages expressing CAR-P$^{FcRγ}$ and Raji B cells were incubated together at a 1:2 macrophage:Raji ratio (20,000 macrophages and 40,000 Rajis) without antibody addition (No ab) or in the presence of anti-CD19 or anti-CD47 antibodies as indicated. The number of whole Raji B cells eaten per 100 macrophages during 4-8 hours of imaging is graphed. Graph depicts pooled data from three independent experiments; n=232 with no antibody, n=257 with anti-CD19 antibody, n=347 with anti-CD47 antibody; * indicates p<0.05 by two-tailed Fisher Exact test.
Figure 8A:
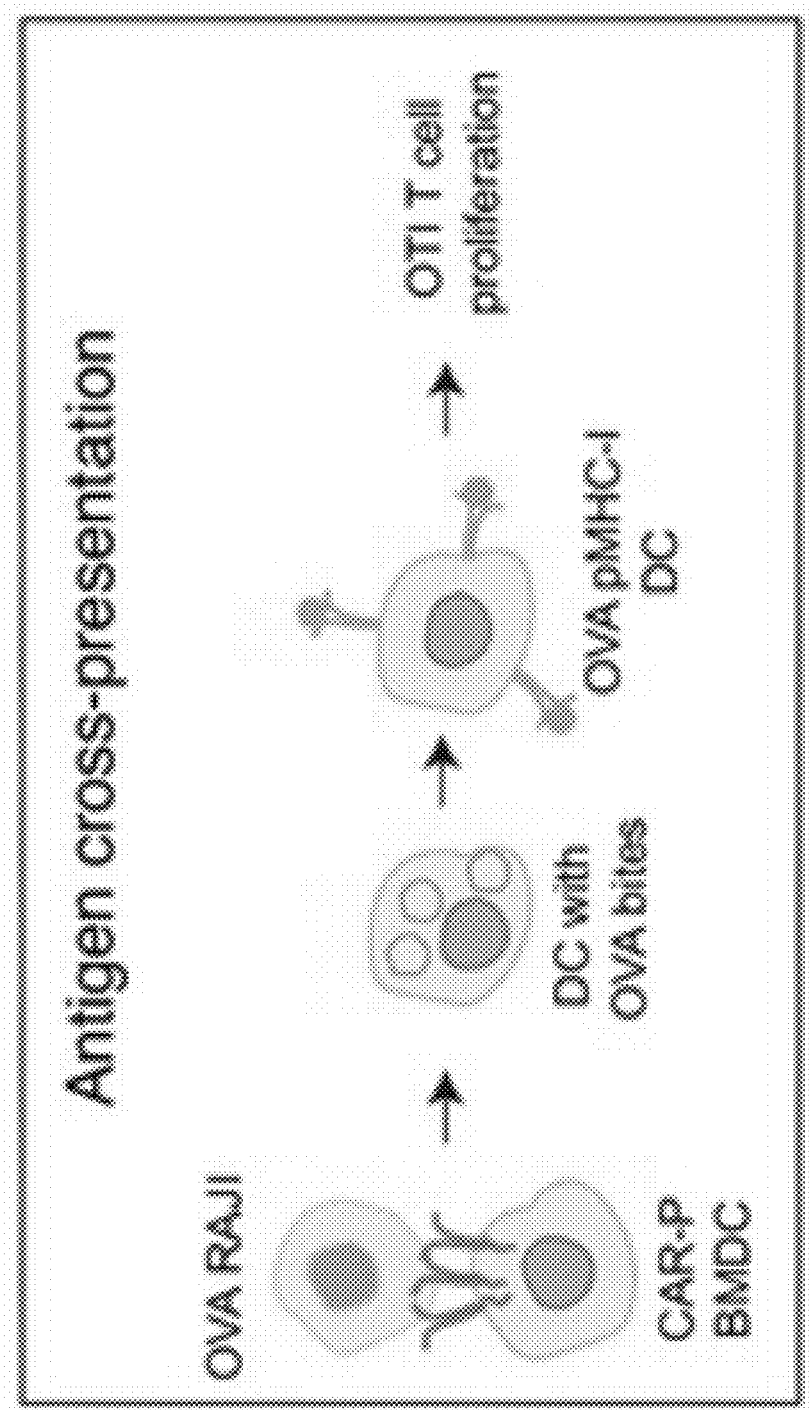
FIGS. 8A-8D summarize the results of experiments demonstrating that CAR-P promotes internalization of cancer antigen.
Figure 8B:
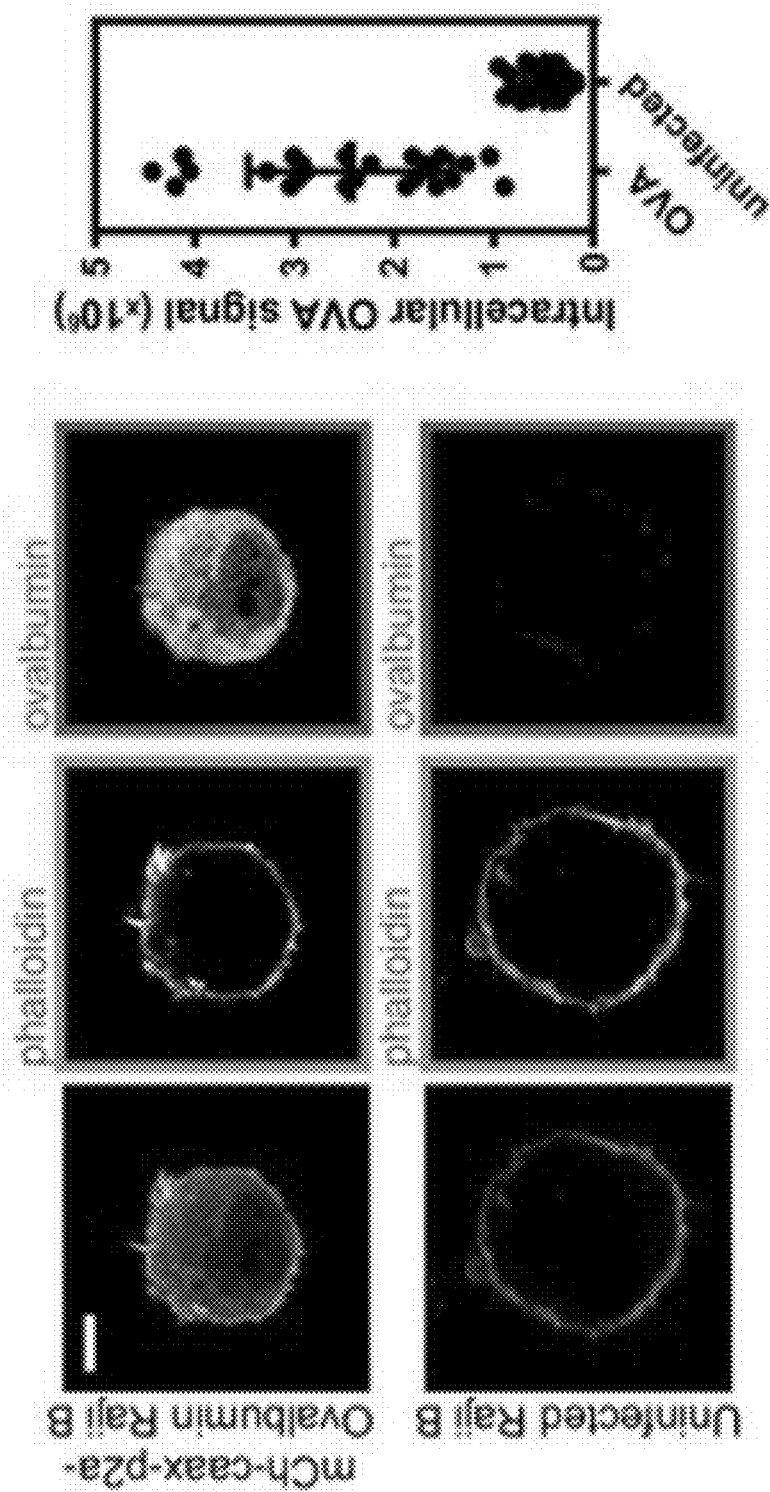
Figure 8C:
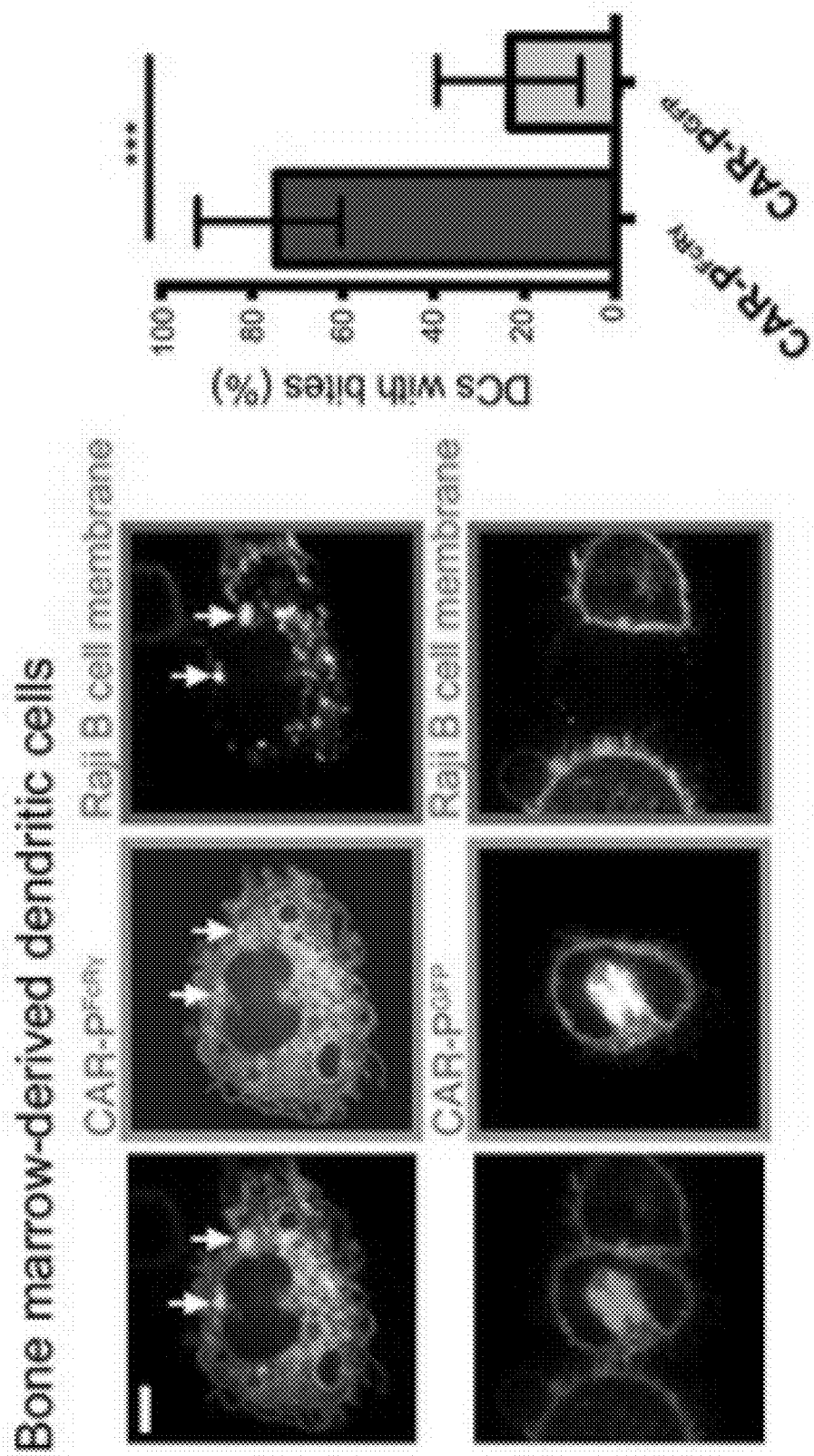
Figure 8D:
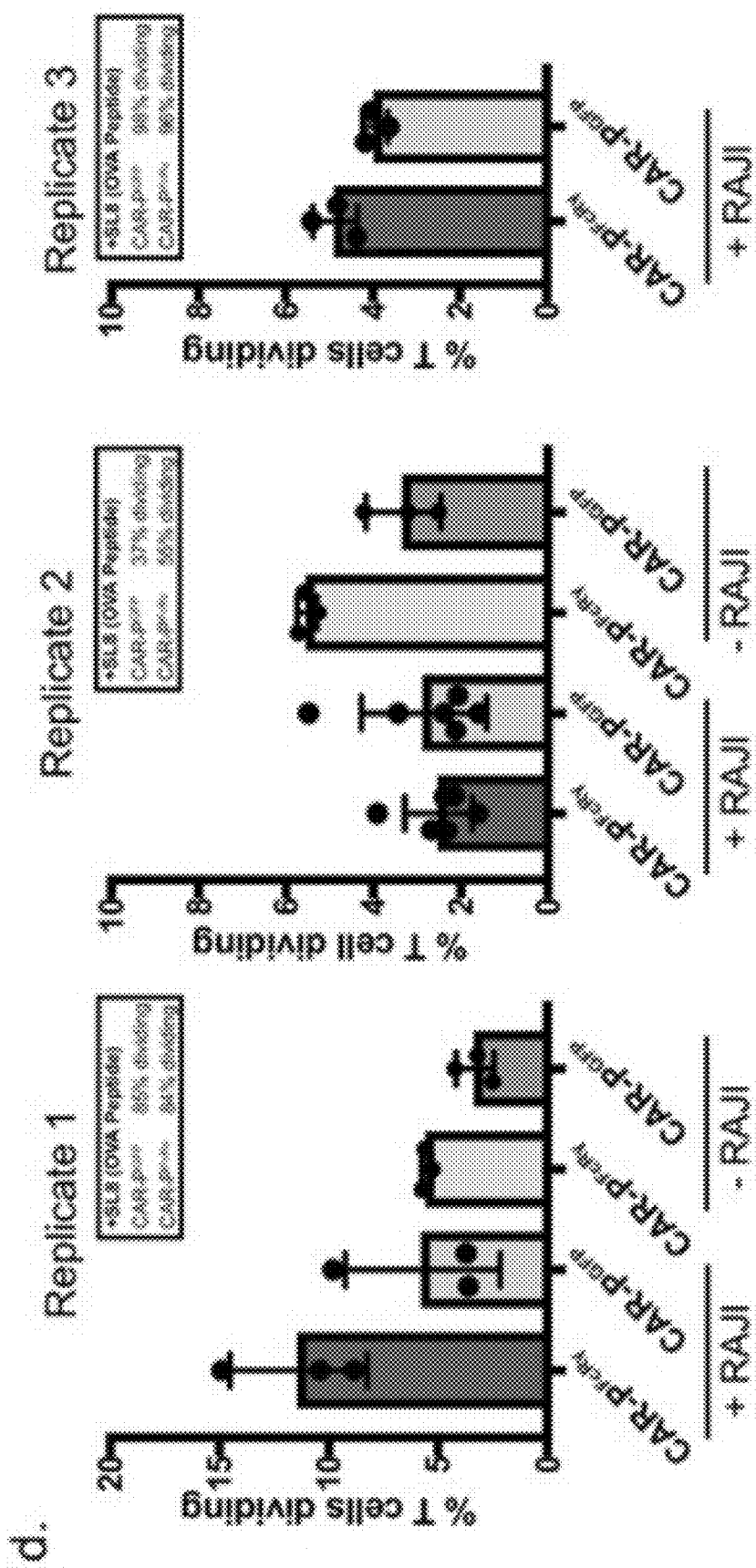

Whole cell engulfment was infrequent but trogocytosis was robust, suggesting that productive macrophage target interactions were frequently insufficient to trigger whole cell engulfment. To determine if whole cell eating could be enhanced by further opsonization of CD19, Raji B cells were opsonized with a mouse IgG2a anti-CD19 antibody. While addition of this antibody did not trigger additional whole cell internalization, blockade of the 'don't eat me' signal CD47 using the mouse IgG1 anti-human B6H12 clone resulted in a 2.5 fold increase of whole cell eating of opsonized Raji B cells (see, e.g., FIG. 7). Both endogenous FcR recognition of the anti-CD47 antibody and blockade of CD47 signaling may contribute to this effect.

Figure 4D:
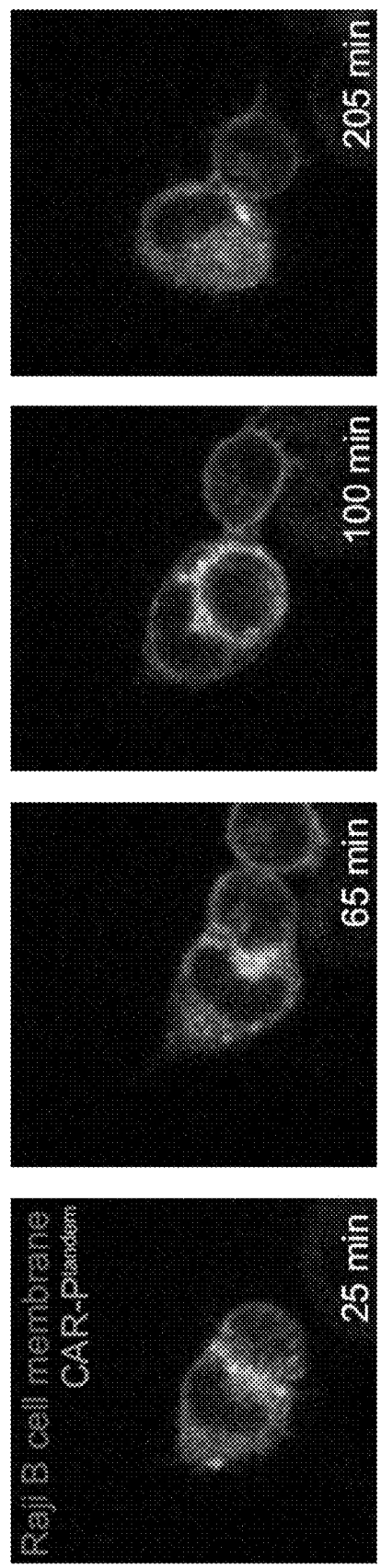
Figure 4E:
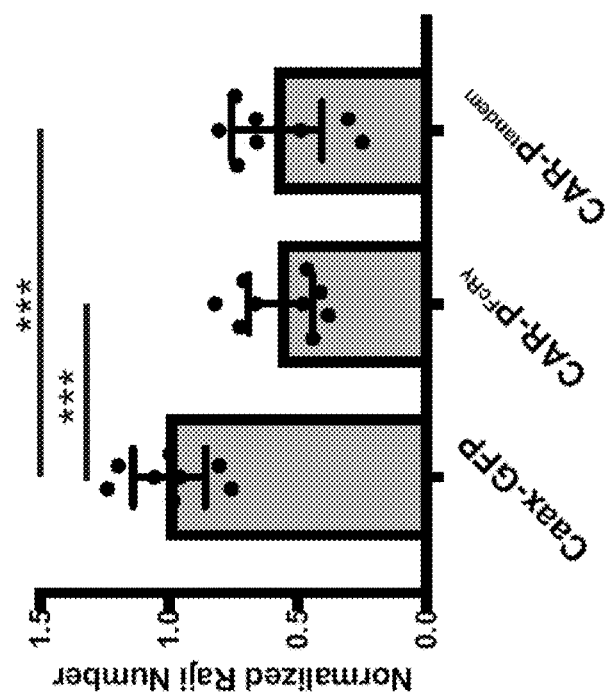

To develop a receptor to enhance whole cell eating, it was hypothesized that combining signaling motifs in a tandem array might increase the frequency of whole cell engulfment by specifically recruiting effectors required for the engulfment of large targets. Previous work demonstrated that PI3K signaling is important for internalization of large targets (Schlam et al., 2015). To increase PI3K recruitment to the CAR-P, the portion of the CD19 cytoplasmic domain (amino acids 500 to 534) that recruits the p85 subunit of PI3K was fused to the CAR-P$^{FcR\gamma}$ creating a 'tandem' CAR (CAR-P$^{tandem}$, FIG. 4C) (Tuveson et al., 1993; Brooks et al., 2004). A CAR-P containing the p85 recruitment motif alone (CAR-PPI3K) was able to induce some whole cell engulfment, comparable to the CAR-P$^{FcR\gamma}$ (FIG. 4E). Expression of CAR-P$^{tandem}$ tripled the ability of macrophages to ingest whole cells compared to CAR-P$^{GFP}$ (6 cancer cells eaten per 100 macrophages) (FIGS. 4D-4E). These data indicate that assembling an array of motifs designed to recruit distinct phagocytic effectors can increase CAR-P activity towards whole cells. A video clip showing the engagement of modified macrophage with Raji B cell was taken and described in Morrissey et al., 2018, supra (see FIG. 4—Supplemental Video 3). This video clip shows that a macrophage infected with αCD19 CAR-P$^{tandem}$ engaged with a Raji B cell (labeled with mCherry-CAAX). The field of view for this video clip was 53×53 μm. Images were acquired every 5 minutes. Time is indicated in the bottom right.

Figure 4F:
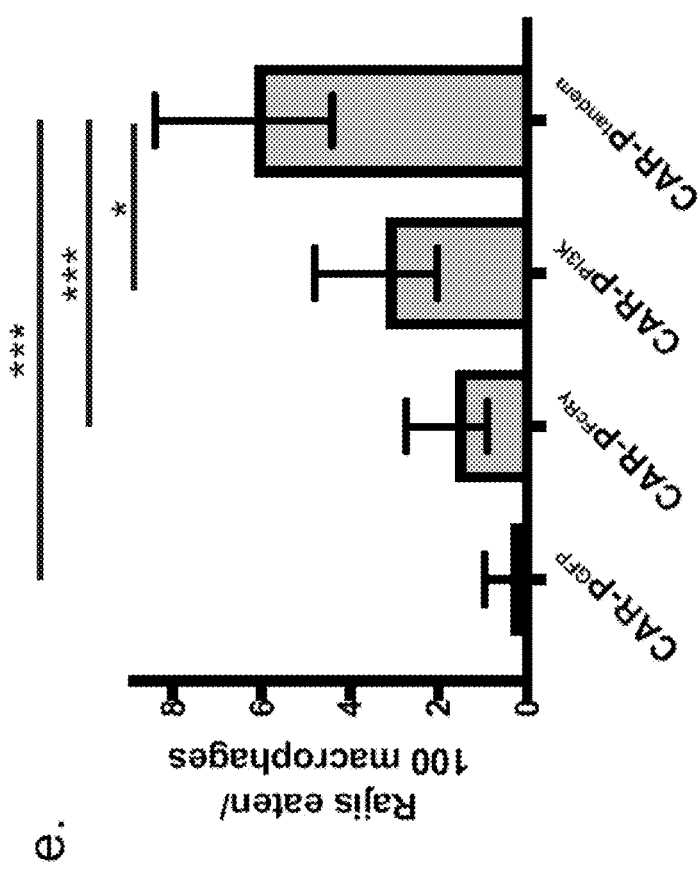

To determine if the combination of whole cell eating and trogocytosis was sufficient to drive a noticeable reduction in cancer cell number, CAR-P macrophages were incubated with Raji B cells for two days. After 44 hours of co-culture, it was found that CAR-P macrophages significantly reduced the number of Raji cells (FIG. 4F). Although the CAR-P$^{tandem}$ was much more efficient at whole cell eating, the CAR-P$^{FcR\gamma}$ performed nearly as well at eliminating Rajis. Importantly, the assay described herein does not distinguish between whole cell engulfment and death following trogocytosis, so it is possible both CAR-P activities are contributing to Raji death rates. Overall, these data suggest that the CAR-P is a successful strategy for directing macrophages towards cancer targets, and can initiate whole cell eating and trogocytosis leading to cancer cell elimination.

Figure 9:
FIG. 9 graphically summarizes the results of experiments illustrating that certain CAR-P provided in the present disclosure are effective in mouse primary macrophages (BMDMs) as demonstrated in a whole-cell eating assay.

In another demonstration, additional experiments were performed to show that the CAR-P described herein is also effective in mouse primary macrophages (BMDMs) as demonstrated in a whole-cell eating assay. The results of these experiments, which is summarized in FIG. 9, illustrate much higher efficacy of the tested CAR-P compared to the efficacy previously observed in cell lines. In these experiments, primary mouse BMDMs were transfected with the CAR-P$^{tandem}$. Macrophages and Raji B cells were incubated together at a 1:2 macrophage:Raji ratio, and the number of whole Raji B cells eaten by 100 macrophages during 4-8 hours of imaging is recorded and graphed. Data is from a single replicate of bone marrow derived macrophages.

In summary, the present disclosure provides engineered phagocytes that recognize and ingest targets through specific antibody-mediated interactions. This strategy can be directed towards multiple extracellular ligands (CD19 and CD22) and can be used with several intracellular signaling domains that contain ITAM motifs (Megf10, FcRγ, and CD3). Previous work has suggested that spatial segregation between Src-family kinases and an inhibitory phosphatase, driven by receptor ligation, is sufficient to trigger signaling by the T cell receptor (Davis and van der Merwe, 2006; James and Vale, 2012) and FcR (Freeman et al., 2016). The CAR-Ps described herein may similarly convert receptor-ligand binding into receptor phosphorylation of ITAM domains through partitioning of kinases and phosphatases at the membrane-membrane interface.

Further development of CAR-Ps will be useful on several therapeutic fronts. Targeting of tumor cells by macrophages has been suggested to cause tumor cell killing (Jaiswal et al., 2009; Majeti et al., 2009; Chao et al., 2010; Jadus et al., 1996), either through directly engulfing cancer cells or by stimulating antigen presentation and a T cell-mediated response (Liu et al., 2015; Tseng et al., 2013). Inhibition of the CD47-SIRPA 'Don't eat me' signaling pathway has also been shown to result in engulfment of cancer cells (Chen et al., 2017; Gardai et al., 2005; Jaiswal et al., 2009; Majeti et al., 2009; Chao et al., 2010). A recent study suggests that CD47 inhibition is most effective when combined with a positive signal to promote target engulfment, which raises the possibility of combining CAR-P expression with CD47 or SIRPA inhibition for an additive effect (Alvey et al., 2017).

Although the experiments described herein show that whole cell engulfment could be increased by recruiting the activating subunit of PI3K to the phagocytic synapse, the engulfment of larger 20 micron beads was more frequent than the engulfment of whole cells. Without being bound to any particular theory, it was hypothesized that this is due to differing physical properties of the engulfment target. Specifically, increased target stiffness has been shown to promote engulfment, suggesting that manipulating the physical properties of the engulfment target could also be a potential strategy for increasing CAR-P efficiency (Beningo and Wang, 2002; Cross et al., 2007).

Overall, the experiments described above demonstrate that the CAR approach is transferrable to biological processes beyond T cell activation and that the expression of an engineered receptor in phagocytic cells is sufficient to promote specific engulfment and elimination of cancer cells.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

REFERENCES

Alvey C, Discher D E. 2017. Engineering macrophages to eat Cancer: from "marker of self" CD47 and phagocytosis to differentiation. Journal of Leukocyte Biology 102:31-40.

Alvey C M, Spinler K R, Irianto J, Pfeifer C R, Hayes B, Xia Y, Cho S, Dingal P, Hsu J, Smith L, Tewari M, Discher D E. 2017. SIRPA-Inhibited, Marrow-Derived macrophages engorge, accumulate, and differentiate in Antibody-Targeted regression of solid tumors. Current Biology 27:2065-2077.

Andreesen R, Scheibenbogen C, Brugger W, Krause S, Meerpohl H G, Leser H G, Engler H, Lo⁻ hr G W. 1990. Adoptive transfer of tumor cytotoxic macrophages generated in vitro from circulating blood monocytes: a new approach to Cancer immunotherapy. Cancer Research 50:7450-7456.

Andreu N, Phelan J, de Sessions P F, Cliff J M, Clark T G, Hibberd M L. 2017. Primary macrophages and J774 cells respond differently to infection with *Mycobacterium tuberculosis*. Scientific Reports 7:42225.

Batista F D, Iber D, Neuberger M S. 2001. B cells acquire antigen from target cells after synapse formation. Nature 411:489-494.

Beningo K A, Wang Y L. 2002. Fc-receptor-mediated phagocytosis is regulated by mechanical properties of the target. Journal of Cell Science 115:849-856.

Brooks S R, Kirkham P M, Freeberg L, Carter R H. 2004. Binding of cytoplasmic proteins to the CD19 intracellular domain is high affinity, competitive, and multimeric. The Journal of Immunology 172:7556-7564.

Bu J Y, Shaw A S, Chan A C. 1995. Analysis of the interaction of ZAP-70 and syk protein-tyrosine kinases with the T-cell antigen receptor by plasmon resonance. PNAS 92:5106-5110.

Chao M P, Alizadeh A A, Tang C, Myklebust J H, Varghese B, Gill S, Jan M, Cha A C, Chan C K, Tan B T, Park C Y, Zhao F, Kohrt H E, Malumbres R, Briones J, Gascoyne R D, Lossos I S, Levy R, Weissman I L, Majeti R. 2010. Anti-CD47 antibody synergizes with rituximab to promote phagocytosis and eradicate non-Hodgkin lymphoma. Cell 142:699-713.

Chen J, Zhong M C, Guo H, Davidson D, Mishel S, Lu Y, Rhee I, Pe'rez-Quintero L A, Zhang S, Cruz-Munoz M E, Wu N, Vinh D C, Sinha M, Calderon V, Lowell C A, Danska J S, Veillette A. 2017. SLAMF7 is critical for phagocytosis of haematopoietic tumour cells via Mac-1 integrin. Nature 544:493-497.

Cross S E, Jin Y S, Rao J, Gimzewski J K. 2007. Nanomechanical analysis of cells from cancer patients. Nature Nanotechnology 2:780-783.

Davis S J, van der Merwe P A. 2006. The kinetic-segregation model: TCR triggering and beyond. Nature Immunology 7:803-809.

Edelstein A, Amodaj N, Hoover K, Vale R, Stuurman N. 2010. Computer control of microscopes using mmanager. Current Protocols in Molecular Biology 14:Unit 14.20.

Engel P, Zhou L J, Ord D C, Sato S, Koller B, Tedder T F. 1995. Abnormal B lymphocyte development, activation, and differentiation in mice that lack or overexpress the CD19 signal transduction molecule. Immunity 3:39-50.

Fesnak A D, June C H, Levine B L. 2016. Engineered T cells: the promise and challenges of cancer immunotherapy. Nature Reviews Cancer 16:566-581.

Freeman S A, Goyette J, Furuya W, Woods E C, Bertozzi C R, Bergmeier W, Hinz B, van der Merwe P A, Das R, Grinstein S. 2016. Integrins Form an Expanding Diffusional Barrier that Coordinates Phagocytosis. Cell 164: 128-140.

Freeman S A, Grinstein S. 2014. Phagocytosis: receptors, signal integration, and the cytoskeleton. Immunological Reviews 262:193-215.

Gardai S J, McPhillips K A, Frasch S C, Janssen W J, Starefeldt A, Murphy-Ullrich J E, Bratton D L, Oldenborg P A, Michalak M, Henson P M. 2005. Cell-surface calreticulin initiates clearance of viable or apoptotic cells through trans-activation of LRP on the phagocyte. Cell 123:321-334.

Harshyne L A, Watkins S C, Gambotto A, Barratt-Boyes S M. 2001. Dendritic cells acquire antigens from live cells for Cross-Presentation to CTL. The Journal of Immunology 166:3717-3723.

Harshyne L A, Zimmer M I, Watkins S C, Barratt-Boyes S M. 2003. A Role for Class A Scavenger Receptor in Dendritic Cell Nibbling from Live Cells. The Journal of Immunology 170:2302-2309.

Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. 2013. Anti-CD22-chimeric antigen receptors targeting B-cell precursor acute lymphoblastic leukemia. Blood 121:1165-1174.

Hui E, Vale R D. 2014. In vitro membrane reconstitution of the T-cell receptor proximal signaling network. Nature Structural & Molecular Biology 21:133-142.

Jadus M R, Irwin M C, Irwin M R, Horansky R D, Sekhon S, Pepper K A, Kohn D B, Wepsic H T. 1996. Macrophages can recognize and kill tumor cells bearing the membrane isoform of macrophage colony-stimulating factor. Blood 87:5232-5241.

Jaiswal S, Jamieson C H, Pang W W, Park C Y, Chao M P, Majeti R, Traver D, van Rooijen N, Weissman I L. 2009. CD47 is upregulated on circulating hematopoietic stem cells and leukemia cells to avoid phagocytosis. Cell 138:271-285.

James J R, Vale R D. 2012. Biophysical mechanism of T-cell receptor triggering in a reconstituted system. Nature 487: 64-69.

Joly E, Hudrisier D. 2003. What is trogocytosis and what is its purpose? Nature Immunology 4:815.

Kao G, Huang C C, Hedgecock E M, Hall D H, Wadsworth W G. 2006. The role of the laminin beta subunit in laminin heterotrimer assembly and basement membrane function and development in *C. elegans*. Developmental Biology 290:211-219.

Kochenderfer J N, Feldman S A, Zhao Y, Xu H, Black M A, Morgan R A, Wilson W H, Rosenberg S A. 2009. Construction and preclinical evaluation of an anti-CD19 chimeric antigen receptor. Journal of Immunotherapy 32:689-702.

Lacerna L V, Stevenson G W, Stevenson H C. 1988. Adoptive cancer immunotherapy utilizing lymphokine activated killer cells and gamma interferon activated killer monocytes. Pharmacology & Therapeutics 38:453-465.

Lee S, Kivimae S, Dolor A, Szoka F C. 2016. Macrophage-based cell therapies: the long and winding road. Journal of Controlled Release 240:527-540.

Lim W A, June C H, Huang J, Hodes R J. 2017. The Principles of Engineering Immune Cells to Treat Cancer. Cell 168:724-740.

Liu X, Pu Y, Cron K, Deng L, Kline J, Frazier W A, Xu H, Peng H, Fu Y X, Xu M M. 2015. CD47 blockade triggers T cell-mediated destruction of immunogenic tumors. Nature Medicine 21:1209-1215.

Majeti R, Chao M P, Alizadeh A A, Pang W W, Jaiswal S, Gibbs K D, van Rooijen N, Weissman I L. 2009. CD47 is an adverse prognostic factor and therapeutic antibody target on human acute myeloid leukemia stem cells. Cell 138:286-299.

Mayordomo J I, Zorina T, Storkus W J, Zitvogel L, Celluzzi C, Falo L D, Melief C J, Ildstad S T, Kast W M, Deleo A B. 1995. Bone marrow-derived dendritic cells pulsed with synthetic tumour peptides elicit protective and therapeutic antitumour immunity. Nature Medicine 1:1297-1302.

Morrissey M A, Williamson A P, Steinbach A M, Roberts E W, Kern N, Headley M B, Vale R D. 2018. Chimeric antigen receptors that trigger phagocytosis. Elife 1:1-10.

Penberthy K K, Ravichandran K S. 2016. Apoptotic cell recognition receptors and scavenger receptors. Immunological Reviews 269:44-59.

Ralston K S, Solga M D, Mackey-Lawrence N M, Somlata, Bhattacharya A, Petri W A. 2014. Trogocytosis by *Entamoeba histolytica* contributes to cell killing and tissue invasion. Nature 508:526-530.

Roberts E W, Broz M L, Binnewies M, Headley M B, Nelson A E, Wolf D M, Kaisho T, Bogunovic D, Bhardwaj N, Krummel M F. 2016. Critical Role for CD103(+)/CD141(+) Dendritic Cells Bearing CCR7 for Tumor Antigen Trafficking and Priming of T Cell Immunity in Melanoma. Cancer Cell 30:324-336.

Schlam D, Bagshaw R D, Freeman S A, Collins R F, Pawson T, Fairn G D, Grinstein S. 2015. Phosphoinositide 3-kinase enables phagocytosis of large particles by terminating actin assembly through Rac/Cdc42 GTPase-activating proteins. Nature Communications 6:8623.

Tseng D, Volkmer J P, Willingham S B, Contreras-Trujillo H, Fathman J W, Fernhoff N B, Seita J, Inlay M A, Weiskopf K, Miyanishi M, Weissman I L. 2013. Anti-CD47 antibody-mediated phagocytosis of cancer by macrophages primes an effective antitumor T-cell response. PNAS 110:11103-11108.

Tuveson D A, Carter R H, Soltoff S P, Fearon D T. 1993. CD19 of B cells as a surrogate kinase insert region to bindphosphatidylinositol 3-kinase. Science 260:986-989.

Weischenfeldt J, Porse B. 2008. Bone Marrow-Derived Macrophages (BMM): Isolation and Applications. Cold Spring Harbor Protocols 2008:pdb.prot5080.

Xiao X, Ho M, Zhu Z, Pastan I, Dimitrov D S. 2009. Identification and characterization of fully human anti-CD22 monoclonal antibodies. mAbs 1:297-303.

What is claimed is:

1. A pharmaceutical composition comprising
   (a) a cell comprising a recombinant polynucleotide, wherein the recombinant polynucleotide comprises a sequence encoding a recombinant polypeptide comprising:
      (i) an extracellular domain comprising an antigen-binding region specific for a cell surface antigen,
      (ii) a transmembrane domain,
      (iii) an intracellular domain comprising:
         (A) an intracellular signaling domain from FcRγ, CD3zeta or Megf10, and
         (B) a p85-recruitment domain that binds a p85 regulatory subunit of phosphoinositide 3-kinase (PI3K), wherein the p85-recruitment domain is from CD19; and
   (b) a pharmaceutically acceptable carrier.

2. The pharmaceutical composition of claim 1, wherein the antigen-binding region comprises an a single-chain variable fragment (scFv) or a single domain antibody (sdAb) variable domain.

3. The pharmaceutical composition of claim 1, wherein the cell surface antigen is selected from the group consisting of CD19, CD22, HER2 (ERBB2/neu), Mesothelin, PSCA, CD123, CD30, CD171, CD138, CS-1, CLECL1, CD33, CD79b, EGFRvIII, GD2, GD3, BCMA, PSMA, ROR1, FLT3, TAG72, CD38, CD44v6, CEA, EPCAM, B7H3 (CD276), KIT (CD117), CD213A2, IL-1 IRa, PRSS21, VEGFR2, FSHR, TROP2, CD24, MUC-16, PDGFR-beta, SSEA-4, CD20, MUC1, EGFR, NCAM, Prostase, PAP, ELF2M, Ephrin B2, FAP, EphA2, GM3, TEM1/CD248, TEM7R, CLDN6, TSHR, GPRC5D, CD97, CD179a, ALK, and IGLL1.

4. The pharmaceutical composition of claim 1, wherein the cell is selected from the group consisting of a macrophage, a dendritic cell, a mast cell, a monocyte, a neutrophil, a microglial cell and an astrocyte.

5. The pharmaceutical composition of claim 4, wherein the cell is a monocyte cell.

6. The pharmaceutical composition of claim 1, wherein the transmembrane domain comprises a stalk and/or transmembrane domain from CD8, Megf10, FcRγ, Bai1, MerTK, TIM4, Stabilin-1, Stabilin-2, RAGE, CD300f, Integrin subunit αv, Integrin subunit β5, CD36, LRP1, SCARF1, C1Qa, Axl, CD45 or CD86.

7. The pharmaceutical composition of claim 6, wherein the transmembrane domain comprises a transmembrane domain from CD8.

8. The pharmaceutical composition of claim 1, wherein the intracellular signaling domain comprises at least 1 ITAM motif.

9. The pharmaceutical composition of claim 1, wherein binding of the antigen-binding region to the cell surface antigen activates an endogenous phagocytic signaling pathway of the cell.

10. The pharmaceutical composition of claim 1, wherein the intracellular domain comprises the intracellular signaling domain from FcRγ.

11. The pharmaceutical composition of claim 1, wherein the intracellular domain comprises the intracellular signaling domain from CD3zeta.

12. The pharmaceutical composition of claim 1, wherein the intracellular domain comprises the intracellular signaling domain from Megf10.

13. The pharmaceutical composition of claim 1, wherein the p85-recruitment domain comprises amino acids 345-379 of SEQ ID NO: 4.

14. The pharmaceutical composition of claim 1, wherein the p85-recruitment domain is operably linked downstream to the intracellular signaling domain from FcRγ.

15. The pharmaceutical composition of claim 1, wherein the recombinant polypeptide comprises SEQ ID NO: 5.

16. The pharmaceutical composition of claim 1, wherein the sequence encoding the recombinant polypeptide comprises SEQ ID NO: 14.

17. The pharmaceutical composition of claim 1, wherein the extracellular domain comprises an scFv specific to CD19, CD22 or HER2 (ERBB2/neu); and wherein the transmembrane domain is a transmembrane domain from CD8.

18. A method of treating cancer in a subject in need thereof comprising administering the pharmaceutical composition of claim 1 to the subject, thereby treating the cancer in the subject.

19. The method of claim 18, wherein the cancer is a lymphoma.

* * * * *

SEQUENCE LISTING

<160> NUMBER OF SEQ ID NOS: 45

<210> SEQ ID NO 1
<211> LENGTH: 578
<212> TYPE: PRT
<213> ORGANISM: Artificial Sequence

```
<220> FEATURE:
<221> NAME/KEY: misc_feature
<222> LOCATION: (1)..(21)
<223> OTHER INFORMATION: signal peptide
<220> FEATURE:
<221> NAME/KEY: misc_feature
<222> LOCATION: (23)..(263)
<223> OTHER INFORMATION: extracellular antigen-binding sequence
<220> FEATURE:
<221> NAME/KEY: misc_feature
<222> LOCATION: (265)..(332)
<223> OTHER INFORMATION: stalk/transmembrane domain for plasma insertion
<220> FEATURE:
<221> NAME/KEY: misc_feature
<222> LOCATION: (333)..(339)
<223> OTHER INFORMATION: basic sequence to improve surface expression
<220> FEATURE:
<221> NAME/KEY: misc_feature
<222> LOCATION: (340)..(578)
<223> OTHER INFORMATION: fluophore
<220> FEATURE:
<221> NAME/KEY: misc_feature
<223> OTHER INFORMATION: CD19-empty CAR-P - control, basic region
      improves membrane expression
```

<400> SEQUENCE: 1

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu

```
                275                 280                 285
Ala Cys Arg Pro Ala Ala Gly Gly Ala Val His Thr Arg Gly Leu Asp
            290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Asn His Arg Asn
                325                 330                 335
Arg Arg Arg Met Val Ser Lys Gly Glu Glu Leu Phe Thr Gly Val Val
            340                 345                 350
Pro Ile Leu Val Glu Leu Asp Gly Asp Val Asn Gly His Lys Phe Ser
                355                 360                 365
Val Ser Gly Glu Gly Glu Gly Asp Ala Thr Tyr Gly Lys Leu Thr Leu
370                 375                 380
Lys Phe Ile Cys Thr Thr Gly Lys Leu Pro Val Pro Trp Pro Thr Leu
385                 390                 395                 400
Val Thr Thr Leu Thr Tyr Gly Val Gln Cys Phe Ser Arg Tyr Pro Asp
                405                 410                 415
His Met Lys Gln His Asp Phe Phe Lys Ser Ala Met Pro Glu Gly Tyr
            420                 425                 430
Val Gln Glu Arg Thr Ile Phe Phe Lys Asp Asp Gly Asn Tyr Lys Thr
            435                 440                 445
Arg Ala Glu Val Lys Phe Glu Gly Asp Thr Leu Val Asn Arg Ile Glu
450                 455                 460
Leu Lys Gly Ile Asp Phe Lys Glu Asp Gly Asn Ile Leu Gly His Lys
465                 470                 475                 480
Leu Glu Tyr Asn Tyr Asn Ser His Asn Val Tyr Ile Met Ala Asp Lys
                485                 490                 495
Gln Lys Asn Gly Ile Lys Val Asn Phe Lys Ile Arg His Asn Ile Glu
            500                 505                 510
Asp Gly Ser Val Gln Leu Ala Asp His Tyr Gln Gln Asn Thr Pro Ile
            515                 520                 525
Gly Asp Gly Pro Val Leu Leu Pro Asp Asn His Tyr Leu Ser Thr Gln
530                 535                 540
Ser Lys Leu Ser Lys Asp Pro Asn Glu Lys Arg Asp His Met Val Leu
545                 550                 555                 560
Leu Glu Phe Val Thr Ala Ala Gly Ile Thr Leu Gly Met Asp Glu Leu
                565                 570                 575
Tyr Lys

<210> SEQ ID NO 2
<211> LENGTH: 847
<212> TYPE: PRT
<213> ORGANISM: Artificial Sequence
<220> FEATURE:
<221> NAME/KEY: misc_feature
<222> LOCATION: (1)..(21)
<223> OTHER INFORMATION: signal peptide
<220> FEATURE:
<221> NAME/KEY: misc_feature
<222> LOCATION: (23)..(263)
<223> OTHER INFORMATION: extracellular antigen-binding sequence
<220> FEATURE:
<221> NAME/KEY: misc_feature
<222> LOCATION: (265)..(332)
<223> OTHER INFORMATION: stalk/transmembrane domain for plasma insertion
<220> FEATURE:
<221> NAME/KEY: misc_feature
<222> LOCATION: (333)..(601)
<223> OTHER INFORMATION: native phagocytosis receptor signaling domain
```

```
<220> FEATURE:
<221> NAME/KEY: misc_feature
<222> LOCATION: (609)..(847)
<223> OTHER INFORMATION: fluophore
<220> FEATURE:
<221> NAME/KEY: misc_feature
<223> OTHER INFORMATION: CD19-mMegf10 CAR-P

<400> SEQUENCE: 2
```

| | | | | | | | | | | | | | | | |
|---|---|---|---|---|---|---|---|---|---|---|---|---|---|---|---|
| Met | Ala | Leu | Pro | Val | Thr | Ala | Leu | Leu | Leu | Pro | Leu | Ala | Leu | Leu | Leu |
| 1 | | | | 5 | | | | | 10 | | | | | 15 | |
| His | Ala | Ala | Arg | Pro | Asp | Ile | Gln | Met | Thr | Gln | Thr | Thr | Ser | Ser | Leu |
| | | | | 20 | | | | | 25 | | | | | 30 | |
| Ser | Ala | Ser | Leu | Gly | Asp | Arg | Val | Thr | Ile | Ser | Cys | Arg | Ala | Ser | Gln |
| | | 35 | | | | | 40 | | | | | 45 | | | |
| Asp | Ile | Ser | Lys | Tyr | Leu | Asn | Trp | Tyr | Gln | Gln | Lys | Pro | Asp | Gly | Thr |
| 50 | | | | | 55 | | | | | 60 | | | | | |
| Val | Lys | Leu | Leu | Ile | Tyr | His | Thr | Ser | Arg | Leu | His | Ser | Gly | Val | Pro |
| 65 | | | | | 70 | | | | | 75 | | | | | 80 |
| Ser | Arg | Phe | Ser | Gly | Ser | Gly | Ser | Gly | Thr | Asp | Tyr | Ser | Leu | Thr | Ile |
| | | | | 85 | | | | | 90 | | | | | 95 | |
| Ser | Asn | Leu | Glu | Gln | Glu | Asp | Ile | Ala | Thr | Tyr | Phe | Cys | Gln | Gln | Gly |
| | | | | 100 | | | | | 105 | | | | | 110 | |
| Asn | Thr | Leu | Pro | Tyr | Thr | Phe | Gly | Gly | Gly | Thr | Lys | Leu | Glu | Ile | Thr |
| | | | | 115 | | | | | 120 | | | | | 125 | |
| Gly | Gly | Gly | Gly | Ser | Gly | Gly | Gly | Ser | Gly | Gly | Gly | Ser | Glu | | |
| 130 | | | | | 135 | | | | | 140 | | | | | |
| Val | Lys | Leu | Gln | Glu | Ser | Gly | Pro | Gly | Leu | Val | Ala | Pro | Ser | Gln | Ser |
| 145 | | | | | 150 | | | | | 155 | | | | | 160 |
| Leu | Ser | Val | Thr | Cys | Thr | Val | Ser | Gly | Val | Ser | Leu | Pro | Asp | Tyr | Gly |
| | | | | 165 | | | | | 170 | | | | | 175 | |
| Val | Ser | Trp | Ile | Arg | Gln | Pro | Pro | Arg | Lys | Gly | Leu | Glu | Trp | Leu | Gly |
| | | | 180 | | | | | 185 | | | | | 190 | | |
| Val | Ile | Trp | Gly | Ser | Glu | Thr | Thr | Tyr | Tyr | Asn | Ser | Ala | Leu | Lys | Ser |
| | | | 195 | | | | | 200 | | | | | 205 | | |
| Arg | Leu | Thr | Ile | Ile | Lys | Asp | Asn | Ser | Lys | Ser | Gln | Val | Phe | Leu | Lys |
| | 210 | | | | | 215 | | | | | 220 | | | | |
| Met | Asn | Ser | Leu | Gln | Thr | Asp | Asp | Thr | Ala | Ile | Tyr | Tyr | Cys | Ala | Lys |
| 225 | | | | | 230 | | | | | 235 | | | | | 240 |
| His | Tyr | Tyr | Tyr | Gly | Gly | Ser | Tyr | Ala | Met | Asp | Tyr | Trp | Gly | Gln | Gly |
| | | | | 245 | | | | | 250 | | | | | 255 | |
| Thr | Ser | Val | Thr | Val | Ser | Ser | Thr | Thr | Thr | Pro | Ala | Pro | Arg | Pro | Pro |
| | | | 260 | | | | | 265 | | | | | 270 | | |
| Thr | Pro | Ala | Pro | Thr | Ile | Ala | Ser | Gln | Pro | Leu | Ser | Leu | Arg | Pro | Glu |
| | | 275 | | | | | 280 | | | | | 285 | | | |
| Ala | Cys | Arg | Pro | Ala | Ala | Gly | Gly | Ala | Val | His | Thr | Arg | Gly | Leu | Asp |
| | 290 | | | | | 295 | | | | | 300 | | | | |
| Phe | Ala | Cys | Asp | Ile | Tyr | Ile | Trp | Ala | Pro | Leu | Ala | Gly | Thr | Cys | Gly |
| 305 | | | | | 310 | | | | | 315 | | | | | 320 |
| Val | Leu | Leu | Leu | Ser | Leu | Val | Ile | Thr | Leu | Tyr | Cys | Tyr | Arg | His | Lys |
| | | | | 325 | | | | | 330 | | | | | 335 | |
| Gln | Lys | Arg | Lys | Glu | Ser | Ser | Met | Pro | Ala | Val | Thr | Tyr | Thr | Pro | Ala |
| | | | 340 | | | | | 345 | | | | | 350 | | |
| Met | Arg | Val | Ile | Asn | Ala | Asp | Tyr | Thr | Ile | Ala | Glu | Thr | Leu | Pro | His |
| | | | 355 | | | | | 360 | | | | | 365 | | |

-continued

Ser Asn Gly Gly Asn Ala Asn Ser His Tyr Phe Thr Asn Pro Ser Tyr
370                 375                 380

His Thr Leu Ser Gln Cys Ala Thr Ser Pro His Val Asn Asn Arg Asp
385                 390                 395                 400

Arg Met Thr Ile Ala Lys Ser Lys Asn Asn Gln Leu Phe Val Asn Leu
                405                 410                 415

Lys Asn Val Asn Pro Gly Lys Arg Gly Thr Leu Val Asp Cys Thr Gly
            420                 425                 430

Thr Leu Pro Ala Asp Trp Lys Gln Gly Tyr Leu Asn Glu Leu Gly
        435                 440                 445

Ala Phe Gly Leu Asp Arg Ser Tyr Met Gly Lys Ser Leu Lys Asp Leu
450                 455                 460

Gly Lys Asn Ser Glu Tyr Asn Ser Ser Thr Cys Ser Leu Ser Ser Ser
465                 470                 475                 480

Glu Asn Pro Tyr Ala Thr Ile Lys Asp Pro Pro Ala Leu Leu Pro Lys
                485                 490                 495

Ser Ser Glu Cys Gly Tyr Val Glu Met Lys Ser Pro Ala Arg Arg Asp
            500                 505                 510

Ser Pro Tyr Ala Glu Ile Asn Asn Ser Thr Pro Ala Asn Arg Asn Val
        515                 520                 525

Tyr Glu Val Glu Pro Thr Val Ser Val Gln Gly Val Phe Ser Asn
530                 535                 540

Ser Gly His Val Thr Gln Asp Pro Tyr Asp Leu Pro Lys Asn Ser His
545                 550                 555                 560

Ile Pro Cys His Tyr Asp Leu Leu Pro Val Arg Asp Ser Ser Ser Ser
                565                 570                 575

Pro Lys Arg Glu Asp Gly Gly Ser Asn Ser Thr Ser Ser Asn Ser
            580                 585                 590

Thr Ser Ser Ser Ser Ser Ser Glu Ala Asp Pro Val Ala Thr
        595                 600                 605

Met Val Ser Lys Gly Glu Glu Leu Phe Thr Gly Val Val Pro Ile Leu
610                 615                 620

Val Glu Leu Asp Gly Asp Val Asn Gly His Lys Phe Ser Val Ser Gly
625                 630                 635                 640

Glu Gly Glu Gly Asp Ala Thr Tyr Gly Lys Leu Thr Leu Lys Phe Ile
                645                 650                 655

Cys Thr Thr Gly Lys Leu Pro Val Pro Trp Pro Thr Leu Val Thr Thr
            660                 665                 670

Leu Thr Tyr Gly Val Gln Cys Phe Ser Arg Tyr Pro Asp His Met Lys
        675                 680                 685

Gln His Asp Phe Phe Lys Ser Ala Met Pro Glu Gly Tyr Val Gln Glu
690                 695                 700

Arg Thr Ile Phe Phe Lys Asp Asp Gly Asn Tyr Lys Thr Arg Ala Glu
705                 710                 715                 720

Val Lys Phe Glu Gly Asp Thr Leu Val Asn Arg Ile Glu Leu Lys Gly
                725                 730                 735

Ile Asp Phe Lys Glu Asp Gly Asn Ile Leu Gly His Lys Leu Glu Tyr
            740                 745                 750

Asn Tyr Asn Ser His Asn Val Tyr Ile Met Ala Asp Lys Gln Lys Asn
        755                 760                 765

Gly Ile Lys Val Asn Phe Lys Ile Arg His Asn Ile Glu Asp Gly Ser
770                 775                 780

Val Gln Leu Ala Asp His Tyr Gln Gln Asn Thr Pro Ile Gly Asp Gly

```
                    785                 790                 795                 800

Pro Val Leu Leu Pro Asp Asn His Tyr Leu Ser Thr Gln Ser Lys Leu
                805                 810                 815

Ser Lys Asp Pro Asn Glu Lys Arg Asp His Met Val Leu Leu Glu Phe
                820                 825                 830

Val Thr Ala Ala Gly Ile Thr Leu Gly Met Asp Glu Leu Tyr Lys
                835                 840                 845

<210> SEQ ID NO 3
<211> LENGTH: 618
<212> TYPE: PRT
<213> ORGANISM: Artificial Sequence
<220> FEATURE:
<221> NAME/KEY: misc_feature
<222> LOCATION: (1)..(21)
<223> OTHER INFORMATION: signal peptide
<220> FEATURE:
<221> NAME/KEY: misc_feature
<222> LOCATION: (23)..(263)
<223> OTHER INFORMATION: extracellular antigen-binding sequence
<220> FEATURE:
<221> NAME/KEY: misc_feature
<222> LOCATION: (265)..(332)
<223> OTHER INFORMATION: stalk/transmembrane domain for plasma insertion
<220> FEATURE:
<221> NAME/KEY: misc_feature
<222> LOCATION: (334)..(377)
<223> OTHER INFORMATION: native phagocytosis receptor signaling domain
<220> FEATURE:
<221> NAME/KEY: misc_feature
<222> LOCATION: (380)..(618)
<223> OTHER INFORMATION: fluophore
<220> FEATURE:
<221> NAME/KEY: misc_feature
<223> OTHER INFORMATION: CD19-FcGamma CAR-P - Native receptor
      (non-optimized)

<400> SEQUENCE: 3

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Gly Ser Glu
        130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
                180                 185                 190
```

```
Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
        210                 215                 220

Met Asn Ser Leu Gln Thr Asp Thr Ala Ile Tyr Tyr Cys Ala Lys
225                 230                 235                 240

His Tyr Tyr Tyr Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Leu Lys
                325                 330                 335

Ile Gln Val Arg Lys Ala Ala Ile Ala Ser Arg Glu Lys Ala Asp Ala
            340                 345                 350

Val Tyr Thr Gly Leu Asn Thr Arg Ser Gln Glu Thr Tyr Glu Thr Leu
        355                 360                 365

Lys His Glu Lys Pro Pro Gln Gly Ser Gly Ser Met Val Ser Lys Gly
    370                 375                 380

Glu Glu Leu Phe Thr Gly Val Val Pro Ile Leu Val Glu Leu Asp Gly
385                 390                 395                 400

Asp Val Asn Gly His Lys Phe Ser Val Ser Gly Glu Gly Glu Gly Asp
                405                 410                 415

Ala Thr Tyr Gly Lys Leu Thr Leu Lys Phe Ile Cys Thr Thr Gly Lys
            420                 425                 430

Leu Pro Val Pro Trp Pro Thr Leu Val Thr Thr Leu Thr Tyr Gly Val
        435                 440                 445

Gln Cys Phe Ser Arg Tyr Pro Asp His Met Lys Gln His Asp Phe Phe
    450                 455                 460

Lys Ser Ala Met Pro Glu Gly Tyr Val Gln Glu Arg Thr Ile Phe Phe
465                 470                 475                 480

Lys Asp Asp Gly Asn Tyr Lys Thr Arg Ala Glu Val Lys Phe Glu Gly
                485                 490                 495

Asp Thr Leu Val Asn Arg Ile Glu Leu Lys Gly Ile Asp Phe Lys Glu
            500                 505                 510

Asp Gly Asn Ile Leu Gly His Lys Leu Glu Tyr Asn Tyr Asn Ser His
        515                 520                 525

Asn Val Tyr Ile Met Ala Asp Lys Gln Lys Asn Gly Ile Lys Val Asn
    530                 535                 540

Phe Lys Ile Arg His Asn Ile Glu Asp Gly Ser Val Gln Leu Ala Asp
545                 550                 555                 560

His Tyr Gln Gln Asn Thr Pro Ile Gly Asp Gly Pro Val Leu Leu Pro
                565                 570                 575

Asp Asn His Tyr Leu Ser Thr Gln Ser Lys Leu Ser Lys Asp Pro Asn
            580                 585                 590

Glu Lys Arg Asp His Met Val Leu Leu Glu Phe Val Thr Ala Ala Gly
        595                 600                 605

Ile Thr Leu Gly Met Asp Glu Leu Tyr Lys
```

-continued

```
           610                 615

<210> SEQ ID NO 4
<211> LENGTH: 620
<212> TYPE: PRT
<213> ORGANISM: Artificial Sequence
<220> FEATURE:
<221> NAME/KEY: misc_feature
<222> LOCATION: (1)..(21)
<223> OTHER INFORMATION: signal peptide
<220> FEATURE:
<221> NAME/KEY: misc_feature
<222> LOCATION: (23)..(263)
<223> OTHER INFORMATION: extracellular antigen-binding sequence
<220> FEATURE:
<221> NAME/KEY: misc_feature
<222> LOCATION: (265)..(332)
<223> OTHER INFORMATION: stalk/transmembrane domain for plasma insertion
<220> FEATURE:
<221> NAME/KEY: misc_feature
<222> LOCATION: (333)..(339)
<223> OTHER INFORMATION: basic sequence to improve surface expression
<220> FEATURE:
<221> NAME/KEY: misc_feature
<222> LOCATION: (345)..(379)
<223> OTHER INFORMATION: PI3K recruitment domain
<220> FEATURE:
<221> NAME/KEY: misc_feature
<222> LOCATION: (387)..(620)
<223> OTHER INFORMATION: fluophore
<220> FEATURE:
<221> NAME/KEY: misc_feature
<223> OTHER INFORMATION: CD19-PI3K CAR-P - Rationally designed ingest
      large targets

<400> SEQUENCE: 4

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220
```

```
Met Asn Ser Leu Gln Thr Asp Asp Thr Ala Ile Tyr Tyr Cys Ala Lys
225                 230                 235                 240

His Tyr Tyr Tyr Gly Ser Tyr Ala Met Asp Tyr Trp Gly Gln Gly
            245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Asn His Arg Asn
                325                 330                 335

Arg Arg Arg Gly Ser Gly Gly Ser Tyr Glu Asp Met Arg Gly Ile Leu
            340                 345                 350

Tyr Ala Ala Pro Gln Leu Arg Ser Ile Arg Gly Gln Pro Gly Pro Asn
            355                 360                 365

His Glu Glu Asp Ala Asp Ser Tyr Glu Asn Met Ser Gly Gly Ser Gly
            370                 375                 380

Ser Val Ser Lys Gly Glu Glu Asp Asn Met Ala Ile Ile Lys Glu Phe
385                 390                 395                 400

Met Arg Phe Lys Val His Met Glu Gly Ser Val Asn Gly His Glu Phe
                405                 410                 415

Glu Ile Glu Gly Glu Gly Glu Gly Arg Pro Tyr Glu Gly Thr Gln Thr
            420                 425                 430

Ala Lys Leu Lys Val Thr Lys Gly Gly Pro Leu Pro Phe Ala Trp Asp
            435                 440                 445

Ile Leu Ser Pro Gln Phe Met Tyr Gly Ser Lys Ala Tyr Val Lys His
450                 455                 460

Pro Ala Asp Ile Pro Asp Tyr Leu Lys Leu Ser Phe Pro Glu Gly Phe
465                 470                 475                 480

Lys Trp Glu Arg Val Met Asn Phe Glu Asp Gly Gly Val Val Thr Val
                485                 490                 495

Thr Gln Asp Ser Ser Leu Gln Asp Gly Glu Phe Ile Tyr Lys Val Lys
            500                 505                 510

Leu Arg Gly Thr Asn Phe Pro Ser Asp Gly Pro Val Met Gln Lys Lys
            515                 520                 525

Thr Met Gly Trp Glu Ala Ser Ser Glu Arg Met Tyr Pro Glu Asp Gly
            530                 535                 540

Ala Leu Lys Gly Glu Ile Lys Gln Arg Leu Lys Leu Lys Asp Gly Gly
545                 550                 555                 560

His Tyr Asp Ala Glu Val Lys Thr Thr Tyr Lys Ala Lys Lys Pro Val
                565                 570                 575

Gln Leu Pro Gly Ala Tyr Asn Val Asn Ile Lys Leu Asp Ile Thr Ser
            580                 585                 590

His Asn Glu Asp Tyr Thr Ile Val Glu Gln Tyr Glu Arg Ala Glu Gly
            595                 600                 605

Arg His Ser Thr Gly Gly Met Asp Glu Leu Tyr Lys
            610                 615                 620

<210> SEQ ID NO 5
<211> LENGTH: 656
```

```
<212> TYPE: PRT
<213> ORGANISM: Artificial Sequence
<220> FEATURE:
<221> NAME/KEY: misc_feature
<222> LOCATION: (1)..(21)
<223> OTHER INFORMATION: signal peptide
<220> FEATURE:
<221> NAME/KEY: misc_feature
<222> LOCATION: (23)..(263)
<223> OTHER INFORMATION: extracellular antigen-binding sequence
<220> FEATURE:
<221> NAME/KEY: misc_feature
<222> LOCATION: (265)..(332)
<223> OTHER INFORMATION: stalk/transmembrane domain for plasma insertion
<220> FEATURE:
<221> NAME/KEY: misc_feature
<222> LOCATION: (334)..(377)
<223> OTHER INFORMATION: native phagocytosis receptor signaling domain
<220> FEATURE:
<221> NAME/KEY: misc_feature
<222> LOCATION: (380)..(413)
<223> OTHER INFORMATION: PI3K recruitment domain
<220> FEATURE:
<221> NAME/KEY: misc_feature
<222> LOCATION: (419)..(656)
<223> OTHER INFORMATION: fluophore
<220> FEATURE:
<221> NAME/KEY: misc_feature
<223> OTHER INFORMATION: CD19-tandem CAR-P - Optimized CAR-P with tandem
      signaling domains (Fc-gamma and PI3K in a linear array)

<400> SEQUENCE: 5
```

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly

```
            245                 250                 255
Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Leu Lys
            325                 330                 335

Ile Gln Val Arg Lys Ala Ala Ile Ala Ser Arg Glu Lys Ala Asp Ala
            340                 345                 350

Val Tyr Thr Gly Leu Asn Thr Arg Ser Gln Glu Thr Tyr Glu Thr Leu
            355                 360                 365

Lys His Glu Lys Pro Pro Gln Gly Ser Gly Ser Tyr Glu Asp Met Arg
        370                 375                 380

Gly Ile Leu Tyr Ala Ala Pro Gln Leu Arg Ser Ile Arg Gly Gln Pro
385                 390                 395                 400

Gly Pro Asn His Glu Glu Asp Ala Asp Ser Tyr Glu Asn Met Gly Ser
                405                 410                 415

Gly Ser Met Val Ser Lys Gly Glu Glu Leu Phe Thr Gly Val Val Pro
            420                 425                 430

Ile Leu Val Glu Leu Asp Gly Asp Val Asn Gly His Lys Phe Ser Val
            435                 440                 445

Ser Gly Glu Gly Glu Gly Asp Ala Thr Tyr Gly Lys Leu Thr Leu Lys
    450                 455                 460

Phe Ile Cys Thr Thr Gly Lys Leu Pro Val Pro Trp Pro Thr Leu Val
465                 470                 475                 480

Thr Thr Leu Thr Tyr Gly Val Gln Cys Phe Ser Arg Tyr Pro Asp His
            485                 490                 495

Met Lys Gln His Asp Phe Phe Lys Ser Ala Met Pro Glu Gly Tyr Val
        500                 505                 510

Gln Glu Arg Thr Ile Phe Phe Lys Asp Asp Gly Asn Tyr Lys Thr Arg
    515                 520                 525

Ala Glu Val Lys Phe Glu Gly Asp Thr Leu Val Asn Arg Ile Glu Leu
    530                 535                 540

Lys Gly Ile Asp Phe Lys Glu Asp Gly Asn Ile Leu Gly His Lys Leu
545                 550                 555                 560

Glu Tyr Asn Tyr Asn Ser His Asn Val Tyr Ile Met Ala Asp Lys Gln
                565                 570                 575

Lys Asn Gly Ile Lys Val Asn Phe Lys Ile Arg His Asn Ile Glu Asp
            580                 585                 590

Gly Ser Val Gln Leu Ala Asp His Tyr Gln Gln Asn Thr Pro Ile Gly
            595                 600                 605

Asp Gly Pro Val Leu Leu Pro Asp Asn His Tyr Leu Ser Thr Gln Ser
        610                 615                 620

Lys Leu Ser Lys Asp Pro Asn Glu Lys Arg Asp His Met Val Leu Leu
625                 630                 635                 640

Glu Phe Val Thr Ala Ala Gly Ile Thr Leu Gly Met Asp Glu Leu Tyr
            645                 650                 655

<210> SEQ ID NO 6
```

```
<211> LENGTH: 842
<212> TYPE: PRT
<213> ORGANISM: Artificial Sequence
<220> FEATURE:
<221> NAME/KEY: misc_feature
<222> LOCATION: (1)..(21)
<223> OTHER INFORMATION: signal peptide
<220> FEATURE:
<221> NAME/KEY: misc_feature
<222> LOCATION: (23)..(258)
<223> OTHER INFORMATION: extracellular antigen-binding sequence
<220> FEATURE:
<221> NAME/KEY: misc_feature
<222> LOCATION: (260)..(327)
<223> OTHER INFORMATION: stalk/transmembrane domain for plasma insertion
<220> FEATURE:
<221> NAME/KEY: misc_feature
<222> LOCATION: (328)..(596)
<223> OTHER INFORMATION: native phagocytosis receptor signaling domain
<220> FEATURE:
<221> NAME/KEY: misc_feature
<222> LOCATION: (604)..(842)
<223> OTHER INFORMATION: fluophore
<220> FEATURE:
<221> NAME/KEY: misc_feature
<223> OTHER INFORMATION: CD22-Megf10 CAR-P

<400> SEQUENCE: 6

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
    130                 135                 140

Ser Ser Gly Gly Gly Gly Ser Asp Ile Gln Met Thr Gln Ser Pro Ser
145                 150                 155                 160

Ser Leu Ser Ala Ser Val Gly Asp Arg Val Thr Ile Thr Cys Arg Ala
                165                 170                 175

Ser Gln Thr Ile Trp Ser Tyr Leu Asn Trp Tyr Gln Gln Arg Pro Gly
            180                 185                 190

Lys Ala Pro Asn Leu Leu Ile Tyr Ala Ala Ser Ser Leu Gln Ser Gly
        195                 200                 205

Val Pro Ser Arg Phe Ser Gly Arg Gly Ser Gly Thr Asp Phe Thr Leu
    210                 215                 220

Thr Ile Ser Ser Leu Gln Ala Glu Asp Phe Ala Thr Tyr Tyr Cys Gln
225                 230                 235                 240

Gln Ser Tyr Ser Ile Pro Gln Thr Phe Gly Gln Gly Thr Lys Leu Glu
                245                 250                 255

Ile Lys Thr Thr Thr Pro Ala Pro Arg Pro Pro Thr Pro Ala Pro Thr
            260                 265                 270
```

```
Ile Ala Ser Gln Pro Leu Ser Leu Arg Pro Glu Ala Cys Arg Pro Ala
            275                 280                 285

Ala Gly Gly Ala Val His Thr Arg Gly Leu Asp Phe Ala Cys Asp Ile
            290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Tyr Arg His Lys Gln Lys Arg Lys Glu
                325                 330                 335

Ser Ser Met Pro Ala Val Thr Tyr Thr Pro Ala Met Arg Val Ile Asn
                340                 345                 350

Ala Asp Tyr Thr Ile Ala Glu Thr Leu Pro His Ser Asn Gly Gly Asn
            355                 360                 365

Ala Asn Ser His Tyr Phe Thr Asn Pro Ser Tyr His Thr Leu Ser Gln
            370                 375                 380

Cys Ala Thr Ser Pro His Val Asn Asn Arg Asp Arg Met Thr Ile Ala
385                 390                 395                 400

Lys Ser Lys Asn Asn Gln Leu Phe Val Asn Leu Lys Asn Val Asn Pro
                405                 410                 415

Gly Lys Arg Gly Thr Leu Val Asp Cys Thr Gly Thr Leu Pro Ala Asp
            420                 425                 430

Trp Lys Gln Gly Gly Tyr Leu Asn Glu Leu Gly Ala Phe Gly Leu Asp
            435                 440                 445

Arg Ser Tyr Met Gly Lys Ser Leu Lys Asp Leu Gly Lys Asn Ser Glu
            450                 455                 460

Tyr Asn Ser Ser Thr Cys Ser Leu Ser Ser Ser Glu Asn Pro Tyr Ala
465                 470                 475                 480

Thr Ile Lys Asp Pro Pro Ala Leu Leu Pro Lys Ser Ser Glu Cys Gly
                485                 490                 495

Tyr Val Glu Met Lys Ser Pro Ala Arg Arg Asp Ser Pro Tyr Ala Glu
                500                 505                 510

Ile Asn Asn Ser Thr Pro Ala Asn Arg Asn Val Tyr Glu Val Glu Pro
            515                 520                 525

Thr Val Ser Val Val Gln Gly Val Phe Ser Asn Ser Gly His Val Thr
            530                 535                 540

Gln Asp Pro Tyr Asp Leu Pro Lys Asn Ser His Ile Pro Cys His Tyr
545                 550                 555                 560

Asp Leu Leu Pro Val Arg Asp Ser Ser Ser Pro Lys Arg Glu Asp
                565                 570                 575

Gly Gly Gly Ser Asn Ser Thr Ser Ser Asn Ser Thr Ser Ser Ser Ser
            580                 585                 590

Ser Ser Ser Glu Ala Asp Pro Pro Val Ala Thr Met Val Ser Lys Gly
            595                 600                 605

Glu Glu Leu Phe Thr Gly Val Val Pro Ile Leu Val Glu Leu Asp Gly
            610                 615                 620

Asp Val Asn Gly His Lys Phe Ser Val Ser Gly Glu Gly Glu Gly Asp
625                 630                 635                 640

Ala Thr Tyr Gly Lys Leu Thr Leu Lys Phe Ile Cys Thr Thr Gly Lys
                645                 650                 655

Leu Pro Val Pro Trp Pro Thr Leu Val Thr Thr Leu Thr Tyr Gly Val
            660                 665                 670

Gln Cys Phe Ser Arg Tyr Pro Asp His Met Lys Gln His Asp Phe Phe
            675                 680                 685
```

```
Lys Ser Ala Met Pro Glu Gly Tyr Val Gln Glu Arg Thr Ile Phe Phe
    690                 695                 700
Lys Asp Asp Gly Asn Tyr Lys Thr Arg Ala Glu Val Lys Phe Glu Gly
705                 710                 715                 720
Asp Thr Leu Val Asn Arg Ile Glu Leu Lys Gly Ile Asp Phe Lys Glu
                725                 730                 735
Asp Gly Asn Ile Leu Gly His Lys Leu Glu Tyr Asn Tyr Asn Ser His
                740                 745                 750
Asn Val Tyr Ile Met Ala Asp Lys Gln Lys Asn Gly Ile Lys Val Asn
            755                 760                 765
Phe Lys Ile Arg His Asn Ile Glu Asp Gly Ser Val Gln Leu Ala Asp
770                 775                 780
His Tyr Gln Gln Asn Thr Pro Ile Gly Asp Gly Pro Val Leu Leu Pro
785                 790                 795                 800
Asp Asn His Tyr Leu Ser Thr Gln Ser Lys Leu Ser Lys Asp Pro Asn
                805                 810                 815
Glu Lys Arg Asp His Met Val Leu Leu Glu Phe Val Thr Ala Ala Gly
            820                 825                 830
Ile Thr Leu Gly Met Asp Glu Leu Tyr Lys
            835                 840
```

```
<210> SEQ ID NO 7
<211> LENGTH: 573
<212> TYPE: PRT
<213> ORGANISM: Artificial Sequence
<220> FEATURE:
<221> NAME/KEY: misc_feature
<222> LOCATION: (1)..(21)
<223> OTHER INFORMATION: signal peptide
<220> FEATURE:
<221> NAME/KEY: misc_feature
<222> LOCATION: (23)..(258)
<223> OTHER INFORMATION: extracellular antigen-binding sequence
<220> FEATURE:
<221> NAME/KEY: misc_feature
<222> LOCATION: (260)..(327)
<223> OTHER INFORMATION: stalk/transmembrane domain for plasma insertion
<220> FEATURE:
<221> NAME/KEY: misc_feature
<222> LOCATION: (328)..(334)
<223> OTHER INFORMATION: basic sequence to improve surface expression
<220> FEATURE:
<221> NAME/KEY: misc_feature
<222> LOCATION: (335)..(573)
<223> OTHER INFORMATION: fluophore
<220> FEATURE:
<221> NAME/KEY: misc_feature
<223> OTHER INFORMATION: CD22-empty CAR-P - control, baisc region
      improves membrane expression
```

```
<400> SEQUENCE: 7

Met Leu Leu Leu Val Thr Ser Leu Leu Leu Cys Glu Leu Pro His Pro
1               5                   10                  15
Ala Phe Leu Leu Ile Pro Gln Val Gln Leu Gln Gln Ser Gly Pro Gly
            20                  25                  30
Leu Val Lys Pro Ser Gln Thr Leu Ser Leu Thr Cys Ala Ile Ser Gly
        35                  40                  45
Asp Ser Val Ser Ser Asn Ser Ala Ala Trp Asn Trp Ile Arg Gln Ser
    50                  55                  60
Pro Ser Arg Gly Leu Glu Trp Leu Gly Arg Thr Tyr Tyr Arg Ser Lys
65                  70                  75                  80
Trp Tyr Asn Asp Tyr Ala Val Ser Val Lys Ser Arg Ile Thr Ile Asn
                85                  90                  95
```

```
Pro Asp Thr Ser Lys Asn Gln Phe Ser Leu Gln Leu Asn Ser Val Thr
            100                 105                 110
Pro Glu Asp Thr Ala Val Tyr Tyr Cys Ala Arg Glu Val Thr Gly Asp
        115                 120                 125
Leu Glu Asp Ala Phe Asp Ile Trp Gly Gln Gly Thr Met Val Thr Val
    130                 135                 140
Ser Ser Gly Gly Gly Gly Ser Asp Ile Gln Met Thr Gln Ser Pro Ser
145                 150                 155                 160
Ser Leu Ser Ala Ser Val Gly Asp Arg Val Thr Ile Thr Cys Arg Ala
                165                 170                 175
Ser Gln Thr Ile Trp Ser Tyr Leu Asn Trp Tyr Gln Gln Arg Pro Gly
            180                 185                 190
Lys Ala Pro Asn Leu Leu Ile Tyr Ala Ala Ser Ser Leu Gln Ser Gly
        195                 200                 205
Val Pro Ser Arg Phe Ser Gly Arg Gly Ser Gly Thr Asp Phe Thr Leu
    210                 215                 220
Thr Ile Ser Ser Leu Gln Ala Glu Asp Phe Ala Thr Tyr Tyr Cys Gln
225                 230                 235                 240
Gln Ser Tyr Ser Ile Pro Gln Thr Phe Gly Gln Gly Thr Lys Leu Glu
                245                 250                 255
Ile Lys Thr Thr Thr Pro Ala Pro Arg Pro Pro Thr Pro Ala Pro Thr
            260                 265                 270
Ile Ala Ser Gln Pro Leu Ser Leu Arg Pro Glu Ala Cys Arg Pro Ala
        275                 280                 285
Ala Gly Gly Ala Val His Thr Arg Gly Leu Asp Phe Ala Cys Asp Ile
    290                 295                 300
Tyr Ile Trp Ala Pro Leu Ala Gly Thr Cys Gly Val Leu Leu Leu Ser
305                 310                 315                 320
Leu Val Ile Thr Leu Tyr Cys Asn His Arg Asn Arg Arg Met Val
                325                 330                 335
Ser Lys Gly Glu Glu Leu Phe Thr Gly Val Val Pro Ile Leu Val Glu
            340                 345                 350
Leu Asp Gly Asp Val Asn Gly His Lys Phe Ser Val Ser Gly Glu Gly
        355                 360                 365
Glu Gly Asp Ala Thr Tyr Gly Lys Leu Thr Leu Lys Phe Ile Cys Thr
    370                 375                 380
Thr Gly Lys Leu Pro Val Pro Trp Pro Thr Leu Val Thr Thr Leu Thr
385                 390                 395                 400
Tyr Gly Val Gln Cys Phe Ser Arg Tyr Pro Asp His Met Lys Gln His
                405                 410                 415
Asp Phe Phe Lys Ser Ala Met Pro Glu Gly Tyr Val Gln Glu Arg Thr
            420                 425                 430
Ile Phe Phe Lys Asp Asp Gly Asn Tyr Lys Thr Arg Ala Glu Val Lys
        435                 440                 445
Phe Glu Gly Asp Thr Leu Val Asn Arg Ile Glu Leu Lys Gly Ile Asp
    450                 455                 460
Phe Lys Glu Asp Gly Asn Ile Leu Gly His Lys Leu Glu Tyr Asn Tyr
465                 470                 475                 480
Asn Ser His Asn Val Tyr Ile Met Ala Asp Lys Gln Lys Asn Gly Ile
                485                 490                 495
Lys Val Asn Phe Lys Ile Arg His Asn Ile Glu Asp Gly Ser Val Gln
            500                 505                 510
```

```
Leu Ala Asp His Tyr Gln Gln Asn Thr Pro Ile Gly Asp Gly Pro Val
            515                 520                 525

Leu Leu Pro Asp Asn His Tyr Leu Ser Thr Gln Ser Lys Leu Ser Lys
    530                 535                 540

Asp Pro Asn Glu Lys Arg Asp His Met Val Leu Leu Glu Phe Val Thr
545                 550                 555                 560

Ala Ala Gly Ile Thr Leu Gly Met Asp Glu Leu Tyr Lys
            565                 570

<210> SEQ ID NO 8
<211> LENGTH: 1054
<212> TYPE: PRT
<213> ORGANISM: Artificial Sequence
<220> FEATURE:
<221> NAME/KEY: misc_feature
<222> LOCATION: (1)..(21)
<223> OTHER INFORMATION: signal peptide
<220> FEATURE:
<221> NAME/KEY: misc_feature
<222> LOCATION: (23)..(263)
<223> OTHER INFORMATION: extracellular antigen-binding sequence
<220> FEATURE:
<221> NAME/KEY: misc_feature
<222> LOCATION: (265)..(332)
<223> OTHER INFORMATION: stalk/transmembrane domain for plasma insertion
<220> FEATURE:
<221> NAME/KEY: misc_feature
<222> LOCATION: (333)..(808)
<223> OTHER INFORMATION: native phagocytosis receptor signaling domain
<220> FEATURE:
<221> NAME/KEY: misc_feature
<222> LOCATION: (816)..(1054)
<223> OTHER INFORMATION: fluophore
<220> FEATURE:
<221> NAME/KEY: misc_feature
<223> OTHER INFORMATION: CD19-MerTK CAR-P - Poor CAR-P (no ITAM domain)

<400> SEQUENCE: 8

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190
```

```
Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
    210                 215                 220

Met Asn Ser Leu Gln Thr Asp Thr Ala Ile Tyr Tyr Cys Ala Lys
225                 230                 235                 240

His Tyr Tyr Tyr Gly Ser Tyr Ala Met Asp Tyr Trp Gly Gln Gly
                245                 250                 255

Thr Ser Val Thr Val Ser Ser Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Ala Leu Arg Arg
                325                 330                 335

Arg Val Gln Glu Thr Lys Phe Gly Gly Ala Phe Ser Glu Glu Asp Ser
            340                 345                 350

Gln Leu Val Val Asn Tyr Arg Ala Lys Lys Ser Phe Cys Arg Arg Ala
        355                 360                 365

Ile Glu Leu Thr Leu Gln Ser Leu Gly Val Ser Glu Glu Leu Gln Asn
    370                 375                 380

Lys Leu Glu Asp Val Val Ile Asp Arg Asn Leu Leu Val Leu Gly Lys
385                 390                 395                 400

Val Leu Gly Glu Gly Glu Phe Gly Ser Val Met Glu Gly Asn Leu Lys
                405                 410                 415

Gln Glu Asp Gly Thr Ser Gln Lys Val Ala Val Lys Thr Met Lys Leu
            420                 425                 430

Asp Asn Phe Ser Gln Arg Glu Ile Glu Glu Phe Leu Ser Glu Ala Ala
        435                 440                 445

Cys Met Lys Asp Phe Asn His Pro Asn Val Ile Arg Leu Leu Gly Val
450                 455                 460

Cys Ile Glu Leu Ser Ser Gln Gly Ile Pro Lys Pro Met Val Ile Leu
465                 470                 475                 480

Pro Phe Met Lys Tyr Gly Asp Leu His Thr Phe Leu Leu Tyr Ser Arg
                485                 490                 495

Leu Asn Thr Gly Pro Lys Tyr Ile His Leu Gln Thr Leu Leu Lys Phe
            500                 505                 510

Met Met Asp Ile Ala Gln Gly Met Glu Tyr Leu Ser Asn Arg Asn Phe
        515                 520                 525

Leu His Arg Asp Leu Ala Ala Arg Asn Cys Met Leu Arg Asp Asp Met
    530                 535                 540

Thr Val Cys Val Ala Asp Phe Gly Leu Ser Lys Lys Ile Tyr Ser Gly
545                 550                 555                 560

Asp Tyr Tyr Arg Gln Gly Arg Ile Ala Lys Met Pro Val Lys Trp Ile
                565                 570                 575

Ala Ile Glu Ser Leu Ala Asp Arg Val Tyr Thr Ser Lys Ser Asp Val
            580                 585                 590

Trp Ala Phe Gly Val Thr Met Trp Glu Ile Thr Thr Arg Gly Met Thr
        595                 600                 605

Pro Tyr Pro Gly Val Gln Asn His Glu Met Tyr Asp Tyr Leu Leu His
```

```
              610                 615                 620
Gly His Arg Leu Lys Gln Pro Glu Asp Cys Leu Asp Glu Leu Tyr Asp
625                 630                 635                 640

Ile Met Tyr Ser Cys Trp Ser Ala Asp Pro Leu Asp Arg Pro Thr Phe
                    645                 650                 655

Ser Val Leu Arg Leu Gln Leu Glu Lys Leu Ser Glu Ser Leu Pro Asp
                660                 665                 670

Ala Gln Asp Lys Glu Ser Ile Ile Tyr Ile Asn Thr Gln Leu Leu Glu
            675                 680                 685

Ser Cys Glu Gly Ile Ala Asn Gly Pro Ser Leu Thr Gly Leu Asp Met
690                 695                 700

Asn Ile Asp Pro Asp Ser Ile Ile Ala Ser Cys Thr Pro Gly Ala Ala
705                 710                 715                 720

Val Ser Val Val Thr Ala Glu Val His Glu Asn Asn Leu Arg Glu Glu
                725                 730                 735

Arg Tyr Ile Leu Asn Gly Gly Asn Glu Glu Trp Glu Asp Val Ser Ser
                740                 745                 750

Thr Pro Phe Ala Ala Val Thr Pro Glu Lys Asp Gly Val Leu Pro Glu
                755                 760                 765

Asp Arg Leu Thr Lys Asn Gly Val Ser Trp Ser His Ser Thr Leu
770                 775                 780

Pro Leu Gly Ser Pro Ser Pro Asp Glu Leu Leu Phe Val Asp Asp Ser
785                 790                 795                 800

Leu Glu Asp Ser Glu Val Leu Met Thr Ser Gly Gly Ser Gly Ser Met
                805                 810                 815

Val Ser Lys Gly Glu Glu Leu Phe Thr Gly Val Val Pro Ile Leu Val
                820                 825                 830

Glu Leu Asp Gly Asp Val Asn Gly His Lys Phe Ser Val Ser Gly Glu
                835                 840                 845

Gly Glu Gly Asp Ala Thr Tyr Gly Lys Leu Thr Leu Lys Phe Ile Cys
850                 855                 860

Thr Thr Gly Lys Leu Pro Val Pro Trp Pro Thr Leu Val Thr Thr Leu
865                 870                 875                 880

Thr Tyr Gly Val Gln Cys Phe Ser Arg Tyr Pro Asp His Met Lys Gln
                885                 890                 895

His Asp Phe Phe Lys Ser Ala Met Pro Glu Gly Tyr Val Gln Glu Arg
                900                 905                 910

Thr Ile Phe Phe Lys Asp Asp Gly Asn Tyr Lys Thr Arg Ala Glu Val
                915                 920                 925

Lys Phe Glu Gly Asp Thr Leu Val Asn Arg Ile Glu Leu Lys Gly Ile
                930                 935                 940

Asp Phe Lys Glu Asp Gly Asn Ile Leu Gly His Lys Leu Glu Tyr Asn
945                 950                 955                 960

Tyr Asn Ser His Asn Val Tyr Ile Met Ala Asp Lys Gln Lys Asn Gly
                965                 970                 975

Ile Lys Val Asn Phe Lys Ile Arg His Asn Ile Glu Asp Gly Ser Val
                980                 985                 990

Gln Leu Ala Asp His Tyr Gln Gln Asn Thr Pro Ile Gly Asp Gly Pro
                995                 1000                1005

Val Leu Leu Pro Asp Asn His Tyr Leu Ser Thr Gln Ser Lys Leu
        1010                1015                1020

Ser Lys Asp Pro Asn Glu Lys Arg Asp His Met Val Leu Leu Glu
        1025                1030                1035
```

Phe Val Thr Ala Ala Gly Ile Thr Leu Gly Met Asp Glu Leu Tyr
    1040                1045                1050

Lys

<210> SEQ ID NO 9
<211> LENGTH: 972
<212> TYPE: PRT
<213> ORGANISM: Artificial Sequence
<220> FEATURE:
<221> NAME/KEY: misc_feature
<222> LOCATION: (1)..(21)
<223> OTHER INFORMATION: signal peptide
<220> FEATURE:
<221> NAME/KEY: misc_feature
<222> LOCATION: (23)..(263)
<223> OTHER INFORMATION: extracellular antigen-binding sequence
<220> FEATURE:
<221> NAME/KEY: misc_feature
<222> LOCATION: (265)..(320)
<223> OTHER INFORMATION: stalk/transmembrane domain for plasma insertion
<220> FEATURE:
<221> NAME/KEY: misc_feature
<222> LOCATION: (321)..(729)
<223> OTHER INFORMATION: native phagocytosis receptor signaling domain
<220> FEATURE:
<221> NAME/KEY: misc_feature
<222> LOCATION: (734)..(972)
<223> OTHER INFORMATION: fluophore
<220> FEATURE:
<221> NAME/KEY: misc_feature
<223> OTHER INFORMATION: CD19-Bai1 CAR-P

<400> SEQUENCE: 9

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

```
Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Glu Val
            325                 330                 335

Gln Asp Ala Val Lys Cys Arg Val Val Asp Arg Gln Glu Glu Gly Asn
            340                 345                 350

Gly Asp Ser Gly Gly Ser Phe Gln Asn Gly His Ala Gln Leu Met Thr
            355                 360                 365

Asp Phe Glu Lys Asp Val Asp Leu Ala Cys Arg Ser Val Leu Asn Lys
            370                 375                 380

Asp Ile Ala Ala Cys Arg Thr Ala Thr Ile Thr Gly Thr Leu Lys Arg
385                 390                 395                 400

Pro Ser Leu Pro Glu Glu Lys Leu Lys Leu Ala His Ala Lys Gly
            405                 410                 415

Pro Pro Thr Asn Phe Asn Ser Leu Pro Ala Asn Val Ser Lys Leu His
            420                 425                 430

Leu His Gly Ser Pro Arg Tyr Pro Gly Gly Pro Leu Pro Asp Phe Pro
            435                 440                 445

Asn His Ser Leu Thr Leu Lys Arg Asp Lys Ala Pro Lys Ser Ser Phe
            450                 455                 460

Val Gly Asp Gly Asp Ile Phe Lys Lys Leu Asp Ser Glu Leu Ser Arg
465                 470                 475                 480

Ala Gln Glu Lys Ala Leu Asp Thr Ser Tyr Val Ile Leu Pro Thr Ala
            485                 490                 495

Thr Ala Thr Leu Arg Pro Lys Pro Lys Glu Pro Lys Tyr Ser Ile
            500                 505                 510

His Ile Asp Gln Met Pro Gln Thr Arg Leu Ile His Leu Ser Thr Ala
            515                 520                 525

Pro Glu Ala Ser Leu Pro Ala Arg Ser Pro Ser Arg Gln Pro Pro
            530                 535                 540

Ser Gly Gly Pro Pro Glu Ala Pro Ala Gln Pro Pro Pro Pro
545                 550                 555                 560

Pro Pro Pro Pro Pro Pro Gln Gln Pro Leu Pro Pro Pro Asn
            565                 570                 575

Leu Glu Pro Ala Pro Pro Ser Leu Gly Asp Pro Gly Glu Pro Ala Ala
            580                 585                 590

His Pro Gly Pro Ser Thr Gly Pro Ser Thr Lys Asn Glu Asn Val Ala
            595                 600                 605

Thr Leu Ser Val Ser Ser Leu Glu Arg Arg Lys Ser Arg Tyr Ala Glu
            610                 615                 620

Leu Asp Phe Glu Lys Ile Met His Thr Arg Lys Arg His Gln Asp Met
625                 630                 635                 640

Phe Gln Asp Leu Asn Arg Lys Leu Gln His Ala Ala Glu Lys Asp Lys
```

```
                        645                 650                 655
Glu Val Leu Gly Pro Asp Ser Lys Pro Glu Lys Gln Gln Thr Pro Asn
                660                 665                 670
Lys Arg Pro Trp Glu Ser Leu Arg Lys Ala His Gly Thr Pro Thr Trp
            675                 680                 685
Val Lys Lys Glu Leu Glu Pro Leu Gln Pro Ser Pro Leu Glu Leu Arg
        690                 695                 700
Ser Val Glu Trp Glu Arg Ser Gly Ala Thr Ile Pro Leu Val Gly Gln
705                 710                 715                 720
Asp Ile Ile Asp Leu Gln Thr Glu Val Gly Ser Gly Ser Met Val Ser
                725                 730                 735
Lys Gly Glu Glu Leu Phe Thr Gly Val Val Pro Ile Leu Val Glu Leu
                740                 745                 750
Asp Gly Asp Val Asn Gly His Lys Phe Ser Val Ser Gly Glu Gly Glu
            755                 760                 765
Gly Asp Ala Thr Tyr Gly Lys Leu Thr Leu Lys Phe Ile Cys Thr Thr
        770                 775                 780
Gly Lys Leu Pro Val Pro Trp Pro Thr Leu Val Thr Thr Leu Thr Tyr
785                 790                 795                 800
Gly Val Gln Cys Phe Ser Arg Tyr Pro Asp His Met Lys Gln His Asp
                805                 810                 815
Phe Phe Lys Ser Ala Met Pro Glu Gly Tyr Val Gln Glu Arg Thr Ile
            820                 825                 830
Phe Phe Lys Asp Asp Gly Asn Tyr Lys Thr Arg Ala Glu Val Lys Phe
        835                 840                 845
Glu Gly Asp Thr Leu Val Asn Arg Ile Glu Leu Lys Gly Ile Asp Phe
    850                 855                 860
Lys Glu Asp Gly Asn Ile Leu Gly His Lys Leu Glu Tyr Asn Tyr Asn
865                 870                 875                 880
Ser His Asn Val Tyr Ile Met Ala Asp Lys Gln Lys Asn Gly Ile Lys
                885                 890                 895
Val Asn Phe Lys Ile Arg His Asn Ile Glu Asp Gly Ser Val Gln Leu
            900                 905                 910
Ala Asp His Tyr Gln Gln Asn Thr Pro Ile Gly Asp Gly Pro Val Leu
        915                 920                 925
Leu Pro Asp Asn His Tyr Leu Ser Thr Gln Ser Lys Leu Ser Lys Asp
    930                 935                 940
Pro Asn Glu Lys Arg Asp His Met Val Leu Leu Glu Phe Val Thr Ala
945                 950                 955                 960
Ala Gly Ile Thr Leu Gly Met Asp Glu Leu Tyr Lys
                965                 970
```

<210> SEQ ID NO 10
<211> LENGTH: 1737
<212> TYPE: DNA
<213> ORGANISM: Artificial Sequence
<220> FEATURE:
<221> NAME/KEY: misc_feature
<223> OTHER INFORMATION: CD19-empty CAR-P - Control, basic region
      improves membrane expression
<220> FEATURE:
<221> NAME/KEY: misc_feature
<223> OTHER INFORMATION: encodes the polypeptide of SEQE ID NO: 1

<400> SEQUENCE: 10
atggccttac cagtgaccgc cttgctcctg ccgctggcct tgctgctcca cgccgccagg    60

```
ccggacatcc agatgacaca gactacatcc tccctgtctg cctctctggg agacagagtc      120
accatcagtt gcagggcaag tcaggacatt agtaaatatt taaattggta tcagcagaaa      180
ccagatggaa ctgttaaact cctgatctac catacatcaa gattacactc aggagtccca      240
tcaaggttca gtggcagtgg gtctggaaca gattattctc tcaccattag caacctggag      300
caagaagata ttgccactta cttttgccaa cagggtaata cgcttccgta cacgttcgga      360
gggggaccaa gctggagat cacaggtggc ggtggctcgg gcggtggtgg gtcgggtggc       420
ggcggatctg aggtgaaact gcaggagtca ggacctggcc tggtggcgcc ctcacagagc      480
ctgtccgtca catgcactgt ctcaggggtc tcattacccg actatggtgt aagctggatt      540
cgccagcctc cacgaaaggg tctggagtgg ctggagtaa tatggggtag tgaaaccaca       600
tactataatt cagctctcaa atccagactg accatcatca aggacaactc caagagccaa      660
gttttcttaa aaatgaacag tctgcaaact gatgacacag ccatttacta ctgtgccaaa      720
cattattact acggtggtag ctatgctatg gactactggg gccaaggaac ctcagtcacc      780
gtctcctcaa ccacgacgcc agcgccgcga ccaccaacac cggcgcccac catcgcgtcg      840
cagcccctgt ccctgcgccc agaggcgtgc cggccagcgg cggggggcgc agtgcacacg      900
agggggctgg acttcgcctg tgatatctac atctgggcgc ccttggccgg acttgtgggg      960
gtccttctcc tgtcactggt tatcacccctt tactgcaacc acaggaaccg aagacgtatg     1020
gtgagcaagg gcgaggagct gttcaccggg gtggtgccca tcctggtcga gctggacggc     1080
gacgtaaacg gccacaagtt cagcgtgtcc ggcgagggcg agggcgatgc cacctacggc     1140
aagctgaccc tgaagttcat ctgcaccacc ggcaagctgc ccgtgccctg gcccaccctc     1200
gtgaccaccc tgacctacgg cgtgcagtgc ttcagccgct accccgacca catgaagcag     1260
cacgacttct tcaagtccgc catgcccgaa ggctacgtcc aggagcgcac catcttcttc     1320
aaggacgacg gcaactacaa gacccgcgcc gaggtgaagt tcgagggcga caccctggtg     1380
aaccgcatcg agctgaaggg catcgacttc aaggaggacg gcaacatcct ggggcacaag     1440
ctggagtaca actacaacag ccacaacgtc tatatcatgg ccgacaagca gaagaacggc     1500
atcaaggtga acttcaagat ccgccacaac atcgaggacg gcagcgtgca gctcgccgac     1560
cactaccagc agaacacccc catcggcgac ggccccgtgc tgctgcccga caaccactac     1620
ctgagcaccc agtccaagct gagcaaagac cccaacgaga gcgcgatca catggtcctg      1680 ctggagttcg tgaccgccgc cgggatcact ctcggcatgg acgagctgta caagtaa       1737

<210> SEQ ID NO 11
<211> LENGTH: 2544
<212> TYPE: DNA
<213> ORGANISM: Artificial Sequence
<220> FEATURE:
<221> NAME/KEY: misc_feature
<223> OTHER INFORMATION: CD19-mMegf10 CAR-P
<220> FEATURE:
<221> NAME/KEY: misc_feature
<223> OTHER INFORMATION: encodes the polypeptide of SEQE ID NO: 2

<400> SEQUENCE: 11
atggccttac cagtgaccgc cttgctcctg ccgctggcct tgctgctcca cgccgccagg       60
ccggacatcc agatgacaca gactacatcc tccctgtctg cctctctggg agacagagtc      120
accatcagtt gcagggcaag tcaggacatt agtaaatatt taaattggta tcagcagaaa      180
ccagatggaa ctgttaaact cctgatctac catacatcaa gattacactc aggagtccca      240
tcaaggttca gtggcagtgg gtctggaaca gattattctc tcaccattag caacctggag      300
```

```
caagaagata ttgccactta cttttgccaa cagggtaata cgcttccgta cacgttcgga      360 gggggggacca agctggagat cacaggtggc ggtggctcgg gcggtggtgg gtcgggtggc      420
ggcggatctg aggtgaaact gcaggagtca ggacctggcc tggtggcgcc ctcacagagc      480
ctgtccgtca catgcactgt ctcaggggtc tcattacccg actatggtgt aagctggatt      540
cgccagcctc cacgaaaggg tctggagtgg ctgggagtaa tatgggggtag tgaaaccaca      600 tactataatt cagctctcaa atccagactg accatcatca aggacaactc caagagccaa      660
gttttcttaa aaatgaacag tctgcaaact gatgacacag ccatttacta ctgtgccaaa      720
cattattact acggtggtag ctatgctatg gactactggg gccaaggaac ctcagtcacc      780
gtctcctcaa ccacgacgcc agcgccgcga ccaccaacac cggcgcccac catcgcgtcg      840
cagcccctgt ccctgcgccc agaggcgtgc cggccagcgg cggggggcgc agtgcacacg      900 aggggggctgg acttcgcctg tgatatctac atctgggcgc ccttggccgg acttgtgggg      960
gtccttctcc tgtcactggt tatcacccct tactgctaca gacacaagca gaagaggaag     1020
gaatcaagca tgccggccgt gacctacacc cccgccatga gagtcatcaa tgcagactat     1080
accatcgcag aaaccctgcc tcacagcaat ggtggaaatg ccaacagcca ctactttacc     1140
aatcccagtt atcacacact tagccagtgt gccacatccc ctcatgtgaa caatagggac     1200
aggatgacca ttgcaaagtc aaaaaacaat cagctgtttg tgaatcttaa aaatgtgaat     1260
ccagggaaga gagggacatt ggtggactgc actgggacat tgccagctga ctggaagcaa     1320
ggaggctacc tcaatgagct tggtgctttc gggctggaca aagctacat gggaaagtcc     1380 ttaaaagatc tggggaagaa ctctgaatat aattcaagca cttgctcctt aagcagctct     1440
gaaaacccat atgccaccat taaagacccg cctgcactcc tgcctaaaag ctccgagtgc     1500
ggctacgtgg agatgaagtc gccggcgcgg agagactccc catatgcaga tcaacaac     1560 tcaactccag ccaacaggaa tgtctatgaa gtcgaaccta cagtgagcgt tgtgcaagga     1620
gtattcagca acagcggtca cgtcacccaa gacccatatg accttccaaa gaacagtcac     1680
atcccttgcc attatgacct gctgccagta agggacagtt catcctcccc aaagagagag     1740
gatggtggtg gcagcaacag caccagcagc aacagcacca gcagcagcag cagcagcagt     1800
gaagcggatc caccggtcgc caccatggtg agcaagggcg aggagctgtt caccggggtg     1860
gtgcccatcc tggtcgagct ggacggcgac gtaaacggcc acaagttcag cgtgtccggc     1920
gagggcgagg gcgatgccac ctacggcaag ctgaccctga agttcatctg caccaccggc     1980
aagctgcccg tgccctggcc caccctcgtg accaccctga cctacggcgt gcagtgcttc     2040
agccgctacc ccgaccacat gaagcagcac gacttcttca gtccgccat gcccgaaggc     2100 tacgtccagg agcgcaccat cttcttcaag gacgacggca actacaagac ccgcgccgag     2160
gtgaagttcg agggcgacac cctggtgaac cgcatcgagc tgaagggcat cgacttcaag     2220
gaggacggca acatcctggg gcacaagctg gagtacaact acaacagcca caacgtctat     2280
atcatggccg acaagcagaa gaacggcatc aaggtgaact tcaagatccg ccacaacatc     2340
gaggacggca gcgtgcagct cgccgaccac taccagcaga caccccccat cggcgacggc     2400
cccgtgctgc tgcccgacaa ccactacctg agcacccagt ccaagctgag caaagacccc     2460
aacgagaagc gcgatcacat ggtcctgctg gagttcgtga ccgccgccgg gatcactctc     2520
ggcatggacg agctgtacaa gtaa                                             2544

<210> SEQ ID NO 12
```

<211> LENGTH: 1832
<212> TYPE: DNA
<213> ORGANISM: Artificial Sequence
<220> FEATURE:
<221> NAME/KEY: misc_feature
<223> OTHER INFORMATION: CD19-FcGamma CAR-P - Native receptor (non-optimized)
<220> FEATURE:
<221> NAME/KEY: misc_feature
<223> OTHER INFORMATION: encodes the polypeptide of SEQE ID NO: 3

<400> SEQUENCE: 12

```
atggccttac cagtgaccgc cttgctcctg ccgctggcct tgctgctcca cgccgccagg     60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa caggtaata cgcttccgta cacgttcgga    360
ggggggacca agctggagat cacaggtggc ggtggctcgg cggtggtgg gtcgggtggc    420
ggcggatctg aggtgaaact gcaggagtca ggacctggcc tggtggcgcc ctcacagagc    480
ctgtccgtca catgcactgt ctcaggggtc tcattacccg actatggtgt aagctggatt    540
cgccagcctc cacgaaaggg tctggagtgg ctgggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcag gcggtggcgg ttcgggtggc ggcgggtcgg gcggtggagg ctctctggga    840
gagccgcagc tctgctatat cctggatgct gtcctgtttt tgtatggtat tgtccttacc    900
ctactctact gtcgactcaa gatccaggtc gaaaggcag ctatagccag ccgtgagaaa    960
gcagatgctg tctacacggg cctgaacacc cggagccagg agacatatga gactctgaag   1020
catgagaaac accccagggg atccggaagt atggtgagca agggcgagga gctgttcacc   1080
ggggtggtgc ccatcctggt cgagctggac ggcgacgtaa acggccacaa gttcagcgtg   1140
tccggcgagg gcgagggcga tgccacctac ggcaagctga ccctgaagtt catctgcacc   1200
accggcaagc tgcccgtgcc ctggcccacc ctcgtgacca cctgaccta cggcgtgcag   1260
tgcttcagcc gctaccccga ccacatgaag cagcacgact tcttcaagtc cgccatgccc   1320
gaaggctacg tccaggagcg caccatcttc ttcaaggacg acggcaacta caagacccgc   1380
gccgaggtga agttcgaggg cgacaccctg gtgaaccgca tcgagctgaa gggcatcgac   1440
ttcaaggagg acggcaacat cctggggcac aagctggagt acaactacaa cagccacaac   1500
gtctatatca tggccgacaa gcagaagaac ggcatcaagg tgaacttcaa gatccgccac   1560
aacatcgagg acggcagcgt gcagctcgcc gaccactacc agcagaacac ccccatcggc   1620
gacggccccg tgctgctgcc cgacaaccac tacctgagca cccagtccaa gctgagcaaa   1680
gaccccaacg agaagcgcga tcacatggtc ctgctggagt tcgtgaccgc cgccgggatc   1740
actctcggca tggacgagct gtacaagtaa agcggccgcg actctagagt cgacctgcag   1800
gcatgcaagc ttgatatcaa gcttatcgat aa                                 1832
```

<210> SEQ ID NO 13
<211> LENGTH: 1863
<212> TYPE: DNA

<213> ORGANISM: Artificial Sequence
<220> FEATURE:
<221> NAME/KEY: misc_feature
<223> OTHER INFORMATION: CD19-PI3K CAR-P
<220> FEATURE:
<221> NAME/KEY: misc_feature
<223> OTHER INFORMATION: encodes the polypeptide of SEQE ID NO: 4

<400> SEQUENCE: 13

| | | | | | |
|---|---|---|---|---|---|
| atggccttac | cagtgaccgc | cttgctcctg | ccgctggcct | tgctgctcca | cgccgccagg | 60 |
| ccggacatcc | agatgacaca | gactacatcc | tccctgtctg | cctctctggg | agacagagtc | 120 |
| accatcagtt | gcagggcaag | tcaggacatt | agtaaatatt | taaattggta | tcagcagaaa | 180 |
| ccagatggaa | ctgttaaact | cctgatctac | catacatcaa | gattacactc | aggagtccca | 240 |
| tcaaggttca | gtggcagtgg | gtctggaaca | gattattctc | tcaccattag | caacctggag | 300 |
| caagaagata | ttgccactta | cttttgccaa | cagggtaata | cgcttccgta | cacgttcgga | 360 |
| ggggggacca | agctggagat | cacaggtggc | ggtggctcgg | gcggtggtgg | gtcgggtggc | 420 |
| ggcggatctg | aggtgaaact | gcaggagtca | ggacctggcc | tggtggcgcc | ctcacagagc | 480 |
| ctgtccgtca | catgcactgt | ctcaggggtc | tcattacccg | actatggtgt | aagctggatt | 540 |
| cgccagcctc | cacgaaaggg | tctggagtgg | ctggagtaa | tatggggtag | tgaaaccaca | 600 |
| tactataatt | cagctctcaa | atccagactg | accatcatca | aggacaactc | caagagccaa | 660 |
| gttttcttaa | aaatgaacag | tctgcaaact | gatgacacag | ccatttacta | ctgtgccaaa | 720 |
| cattattact | acggtggtag | ctatgctatg | gactactggg | gccaaggaac | ctcagtcacc | 780 |
| gtctcctcaa | ccacgacgcc | agcgccgcga | ccaccaacac | cggcgcccac | catcgcgtcg | 840 |
| cagcccctgt | ccctgcgccc | agaggcgtgc | cggccagcgg | cggggggcgc | agtgcacacg | 900 |
| aggggggctgg | acttcgcctg | tgatatctac | atctgggcgc | ccttggccgg | acttgtgggg | 960 |
| gtccttctcc | tgtcactggt | tatcacccttt | tactgcaacc | acaggaaccg | aagacgtgga | 1020 |
| tccgaggca | gttatgagga | tatgagagga | atcctgtatg | cagcccccca | gctccgctcc | 1080 |
| attcggggcc | agcctggacc | caatcatgag | gaagatgcag | actcttatga | gaacatgagt | 1140 |
| ggtggatccg | gaagtgtgag | caagggcgag | gaggataaca | tggccatcat | caaggagttc | 1200 |
| atgcgcttca | aggtgcacat | ggagggctcc | gtgaacggcc | acgagttcga | gatcgagggc | 1260 |
| gagggcgagg | gccgcccta | cgagggcacc | cagaccgcca | gctgaaggt | gaccaagggt | 1320 |
| ggccccctgc | ccttcgcctg | ggacatcctg | tcccctcagt | tcatgtacgg | ctccaaggcc | 1380 |
| tacgtgaagc | accccgccga | catccccgac | tacttgaagc | tgtccttccc | cgagggcttc | 1440 |
| aagtgggagc | gcgtgatgaa | cttcgaggac | ggcggcgtgg | tgaccgtgac | ccaggactcc | 1500 |
| tccctgcagg | acggcgagtt | catctacaag | gtgaagctgc | gcggcaccaa | cttcccctcc | 1560 |
| gacggccccg | taatgcagaa | gaagaccatg | ggctgggagg | cctcctccga | gcggatgtac | 1620 |
| cccgaggacg | cgccctgaa | gggcgagatc | aagcagaggc | tgaagctgaa | ggacggcggc | 1680 |
| cactacgacg | ctgaggtcaa | gaccacctac | aaggccaaga | agcccgtgca | gctgcccggc | 1740 |
| gcctacaacg | tcaacatcaa | gttggacatc | acctcccaca | acgaggacta | caccatcgtg | 1800 |
| gaacagtacg | aacgcgccga | gggccgccac | tccaccggcg | gcatggacga | gctgtacaag | 1860 |
| taa | | | | | | 1863 |

<210> SEQ ID NO 14
<211> LENGTH: 1974
<212> TYPE: DNA
<213> ORGANISM: Artificial Sequence
<220> FEATURE:
<221> NAME/KEY: misc_feature
<223> OTHER INFORMATION: CD19-tandem CAR-P
<220> FEATURE:
<221> NAME/KEY: misc_feature
<223> OTHER INFORMATION: encodes the polypeptide of SEQE ID NO: 5

<400> SEQUENCE: 14

```
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa cagggtaata cgcttccgta cacgttcgga     360
gggggaccca agctggagat cacaggtggc ggtggctcgg cggtggtgg tcgggtggc      420
ggcggatctg aggtgaaact gcaggagtca ggacctggcc tggtggcgcc ctcacagagc     480
ctgtccgtca catgcactgt ctcagggtc tcattacccg actatggtgt aagctggatt     540
cgccagcctc cacgaaaggg tctggagtgg ctgggagtaa tatggggtag tgaaaccaca     600
tactataatt cagctctcaa atccagactg accatcatca aggacaactc caagagccaa     660
gttttcttaa aaatgaacag tctgcaaact gatgacacag ccatttacta ctgtgccaaa     720
cattattact acggtggtag ctatgctatg gactactggg gccaaggaac ctcagtcacc     780
gtctcctcaa ccacgacgcc agcgccgcga ccaccaacac cggcgcccac catcgcgtcg     840
cagcccctgt ccctgcgccc agaggcgtgc cggccagcgg cgggggcgc agtgcacacg     900
agggggctgg acttcgcctg tgatatctac atctgggcgc ccttggccgg acttgtggg     960
gtccttctcc tgtcactggt tatcaccctt tactgcagac gactcaagat ccaggtccga    1020
aaggcagcta tagccagccg tgagaaagca gatgctgtct acacgggcct gaacaccc gg    1080
agccaggaga catatgagac tctgaagcat gagaaaccac cccagggatc cggaagttat    1140
gaggatatga ggaatcct gtatgcagcc cccagctcc gctccattcg gggccagcct    1200
ggacccaatc atgaggaaga tgcagactct tatgagaaca tgggatccgg aagtatggtg    1260
agcaagggcg aggagctgtt caccggggtg gtgcccatcc tggtcgagct ggacggcgac    1320
gtaaacggcc acaagttcag cgtgtccggc gagggcgagg gcgatgccac ctacggcaag    1380
ctgaccctga agttcatctg caccaccggc aagctgcccg tgccctggcc caccctcgtg    1440
accaccctga cctacggcgt gcagtgcttc agccgctacc ccgaccacat gaagcagcac    1500
gacttcttca gtccgccat gcccgaaggc tacgtccagg agcgcaccat cttcttcaag    1560
gacgacggca actacaagac ccgcgccgag gtgaagttcg agggcgacac cctggtgaac    1620
cgcatcgagc tgaagggcat cgacttcaag gaggacggca acatcctggg gcacaagctg    1680
gagtacaact acaacagcca caacgtctat atcatggccg acaagcagaa gaacggcatc    1740
aaggtgaact tcaagatccg ccacaacatc gaggacggca gcgtgcagct cgccgaccac    1800
taccagcaga acacccccat cggcgacggc cccgtgctgc tgcccgacaa ccactacctg    1860
agcacccagt ccaagctgag caaagacccc aacgagaagc gcgatcacat ggtcctgctg    1920
gagttcgtga ccgccgccgg gatcactctc ggcatggacg agctgtacaa gtaa           1974
```

<210> SEQ ID NO 15
<211> LENGTH: 2529
<212> TYPE: DNA

<213> ORGANISM: Artificial Sequence
<220> FEATURE:
<221> NAME/KEY: misc_feature
<223> OTHER INFORMATION: CD22-Megf10 CAR-P
<220> FEATURE:
<221> NAME/KEY: misc_feature
<223> OTHER INFORMATION: encodes the polypeptide of SEQ ID NO: 6

<400> SEQUENCE: 15

| | | | | | |
|---|---|---|---|---|---|
| atgcttctgc | tcgtgacaag | cctgctgctg | tgcgagctgc | cccaccctgc | ctttctgctg | 60 |
| atccctcagg | tgcagctgca | gcagtctggc | cctggcctcg | tgaagcctag | ccagaccctg | 120 |
| agcctgacct | gtgccatcag | cggcgatagc | gtgtccagca | atagcgccgc | ctggaactgg | 180 |
| atcagacaga | gccctagcag | aggcctggaa | tggctgggcc | ggacctacta | ccggtccaag | 240 |
| tggtacaacg | actacgccgt | gtccgtgaag | tcccggatca | ccatcaaccc | cgacaccagc | 300 |
| aagaaccagt | tctccctgca | gctgaacagc | gtgacccccg | aggataccgc | cgtgtactac | 360 |
| tgcgccagag | aagtgaccgg | cgacctggaa | gatgccttcg | acatctgggg | ccagggcaca | 420 |
| atggtcaccg | tgtctagcgg | aggcggcgga | agcgacatcc | agatgacaca | gagccccagc | 480 |
| tccctgagcg | ccagcgtggg | agacagagtg | accatcacct | gtcgggccag | ccagaccatc | 540 |
| tggtcctacc | tgaactggta | tcagcagcgg | cctggcaagg | cccccaacct | gctgatctat | 600 |
| gccgccagct | cactgcagag | cggcgtgccc | agcagatttt | ccggcagagg | cagcggcacc | 660 |
| gacttcaccc | tgacaatcag | ttccctgcag | gccgaggact | tcgccaccta | ctactgccag | 720 |
| cagagctaca | gcatcccccca | gaccttcggc | caggggacca | agctggaaat | caaaaccacg | 780 |
| acgccagcgc | cgcgaccacc | aacaccggcg | cccaccatcg | cgtcgcagcc | cctgtccctg | 840 |
| cgcccagagg | cgtgccggcc | agcggcgggg | ggcgcagtgc | acacgagggg | gctggacttc | 900 |
| gcctgtgata | tctacatctg | ggcgcccttg | gccgggactt | gtggggtcct | tctcctgtca | 960 |
| ctggttatca | ccctttactg | ctacagacac | aagcagaaga | ggaaggaatc | aagcatgccg | 1020 |
| gccgtgacct | acacccccgc | catgagagtc | atcaatgcag | actataccat | cgcagaaacc | 1080 |
| ctgcctcaca | gcaatggtgg | aaatgccaac | agccactact | ttaccaatcc | cagttatcac | 1140 |
| acacttagcc | agtgtgccac | atcccctcat | gtgaacaata | gggacaggat | gaccattgca | 1200 |
| aagtcaaaaa | acaatcagct | gtttgtgaat | cttaaaaatg | tgaatccagg | aagagagggg | 1260 |
| acattggtgg | actgcactgg | gacattgcca | gctgactgga | agcaaggagg | ctacctcaat | 1320 |
| gagcttggtg | ctttcgggct | ggacagaagc | tacatgggaa | agtccttaaa | agatctgggg | 1380 |
| aagaactctg | aatataattc | aagcacttgc | tccttaagca | gctctgaaaa | cccatatgcc | 1440 |
| accattaaag | acccgcctgc | actcctgcct | aaaagctccg | agtgcggcta | cgtggagatg | 1500 |
| aagtcgccgg | cgcggagaga | ctccccatat | gcagagatca | caactcaac | tccagccaac | 1560 |
| aggaatgtct | atgaagtcga | acctacagtg | agcgttgtgc | aaggagtatt | cagcaacagc | 1620 |
| ggtcacgtca | cccaagaccc | atatgaccct | tcaaagaaca | gtcacatccc | ttgccattat | 1680 |
| gacctgctgc | cagtaaggga | cagttcatcc | tccccaaaga | gagaggatgg | tggtggcagc | 1740 |
| aacagcacca | gcagcaacag | caccagcagc | agcagcagca | gcagtgaagc | ggatccaccg | 1800 |
| gtcgccacca | tggtgagcaa | gggcgaggag | ctgttcaccg | gggtggtgcc | catcctggtc | 1860 |
| gagctggacg | gcgacgtaaa | cggccacaag | ttcagcgtgt | ccggcgaggg | cgagggcgat | 1920 |
| gccacctacg | gcaagctgac | cctgaagttc | atctgcacca | ccggcaagct | gcccgtgccc | 1980 |
| tggcccaccc | tcgtgaccac | cctgacctac | ggcgtgcagt | gcttcagccg | ctaccccgac | 2040 |
| cacatgaagc | agcacgactt | cttcaagtcc | gccatgcccg | aaggctacgt | ccaggagcgc | 2100 |

```
accatcttct tcaaggacga cggcaactac aagacccgcg ccgaggtgaa gttcgagggc   2160
gacaccctgg tgaaccgcat cgagctgaag ggcatcgact tcaaggagga cggcaacatc   2220
ctggggcaca agctggagta caactacaac agccacaacg tctatatcat ggccgacaag   2280
cagaagaacg gcatcaaggt gaacttcaag atccgccaca acatcgagga cggcagcgtg   2340
cagctcgccg accactacca gcagaacacc cccatcggcg acggccccgt gctgctgccc   2400
gacaaccact acctgagcac ccagtccaag ctgagcaaag accccaacga gaagcgcgat   2460
cacatggtcc tgctggagtt cgtgaccgcc gccgggatca ctctcggcat ggacgagctg   2520
tacaagtaa                                                          2529

<210> SEQ ID NO 16
<211> LENGTH: 1722
<212> TYPE: DNA
<213> ORGANISM: Artificial Sequence
<220> FEATURE:
<221> NAME/KEY: misc_feature
<223> OTHER INFORMATION: CD22-empty CAR-P
<220> FEATURE:
<221> NAME/KEY: misc_feature
<223> OTHER INFORMATION: encodes the polypeptide of SEQ ID NO: 7

<400> SEQUENCE: 16
atgcttctgc tcgtgacaag cctgctgctg tgcgagctgc cccaccctgc ctttctgctg     60
atccctcagg tgcagctgca gcagtctggc cctggcctcg tgaagcctag ccagaccctg    120
agcctgacct gtgccatcag cggcgatagc gtgtccagca atagcgccgc ctggaactgg    180
atcagacaga gccctagcag aggcctggaa tggctgggcc ggacctacta ccggtccaag    240
tggtacaacg actacgccgt gtccgtgaag tccggatca ccatcaaccc cgacaccagc    300
aagaaccagt tctccctgca gctgaacagc gtgaccccg aggataccgc cgtgtactac    360
tgcgccagag aagtgaccgg cgacctgaa gatgccttcg acatctgggg ccagggcaca    420
atggtcaccg tgtctagcgg aggcggcgga agcgacatcc agatgacaca gagccccagc    480
tccctgagcg ccagcgtggg agacagagtg accatcacct gtcgggccag ccagaccatc    540
tggtcctacc tgaactggta tcagcagcgg cctggcaagg cccccaacct gctgatctat    600
gccgccagct cactgcagag cggcgtgccc agcagatttt ccggcagagg cagcggcacc    660
gacttcaccc tgacaatcag ttccctgcag gccgaggact cgccaccta ctactgccag    720 cagagctaca gcatccccca gaccttcggc caggggacca agctggaaat caaaaccacg    780
acgccagcgc cgcgaccacc aacaccggcg cccaccatcg cgtcgcagcc cctgtccctg    840
cgcccagagg cgtgccggcc agcggcgggg ggcgcagtgc acacgagggg gctggacttc    900
gcctgtgata tctacatctg gcgcccttg ccgggacttg tgggtcct tctcctgtca    960 ctggttatca ccctttactg caaccacagg aaccgaagac gtatggtgag caagggcgag   1020
gagctgttca ccggggtggt gcccatcctg gtcgagctgg acggcgacgt aaacggccac   1080
aagttcagcg tgtccggcga gggcgagggc gatgccacct acggcaagct gaccctgaag   1140
ttcatctgca ccaccggcaa gctgcccgtg ccctggccca cccctgtgac cacctgacc   1200 tacggcgtgc agtgcttcag ccgctacccc gaccacatga agcagcacga cttcttcaag   1260
tccgccatgc ccgaaggcta cgtccaggag cgcaccatct tcttcaagga cgacggcaac   1320
tacaagaccc gcgccgaggt gaagttcgag ggcgacaccc tggtgaaccg catcgagctg   1380
aagggcatcg acttcaagga ggacggcaac atcctggggc acaagctgga gtacaactac   1440
```

```
aacagccaca acgtctatat catggccgac aagcagaaga acggcatcaa ggtgaacttc   1500
aagatccgcc acaacatcga ggacggcagc gtgcagctcg ccgaccacta ccagcagaac   1560
acccccatcg gcgacggccc cgtgctgctg cccgacaacc actacctgag cacccagtcc   1620
aagctgagca agacccccaa cgagaagcgc gatcacatgg tcctgctgga gttcgtgacc   1680
gccgccggga tcactctcgg catggacgag ctgtacaagt aa                     1722
```

<210> SEQ ID NO 17
<211> LENGTH: 3165
<212> TYPE: DNA
<213> ORGANISM: Artificial Sequence
<220> FEATURE:
<221> NAME/KEY: misc_feature
<223> OTHER INFORMATION: CD19-MerTK CAR-P
<220> FEATURE:
<221> NAME/KEY: misc_feature
<223> OTHER INFORMATION: encodes the polypeptide of SEQE ID NO: 8

<400> SEQUENCE: 17

```
atggccttac cagtgaccgc cttgctcctg ccgctggcct tgctgctcca cgccgccagg     60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa cagggtaata cgcttccgta cacgttcgga    360
ggggggacca agctggagat cacaggtggc ggtggctcgg gcggtggtgg gtcgggtggc    420
ggcggatctg aggtgaaact gcaggagtca ggacctggcc tggtggcgcc ctcacagagc    480
ctgtccgtca catgcactgt ctcaggggtc tcattacccg actatggtgt aagctggatt    540
cgccagcctc cacgaaaggg tctggagtgg ctgggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cggggggcgc agtgcacacg    900
agggggctgg acttcgcctg tgatatctac atctgggcgc ccttggccgg acttgtgggg    960
gtccttctcc tgtcactggt tatcaccctt tactgcgccc tcagaaggag agtccaggaa   1020
acaaagtttg ggggagcatt tctgaggag gattcccaac tggtcgtaaa ttatagagcg    1080
aagaagtcct tctgccggcg agccatcgag cttaccttgc agagcctggg agtgagcgag   1140
gagctgcaga ataagctgga agatgttgtg attgacagaa accttctggt tctcggcaaa   1200
gttctgggtg aaggagagtt tgggtctgta atggaaggaa atttgaagca agaagatggg   1260
acttctcaga aggtggcagt gaagaccatg aagttggaca cttttctcac acgggagatc   1320
gaggagtttc tcagcgaagc agcatgcatg aaagacttca accacccaaa tgtcatccga   1380
cttctaggcg tgtgtataga actgagctct caaggcatcc cgaagcccat ggtgattta   1440 cccttcatga atacggaga cctccacacc ttcctgttat attcccgatt aaacacagga   1500
cccaagtaca ttcacctgca gacactactg aagttcatga tggacattgc ccagggaatg   1560
gagtatctga gcaacaggaa ttttcttcat agggatttgg cagctcgaaa ctgcatgttg    1620
cgggatgaca tgactgtctg cgtggcagac tttggcctct caaagaagat ttacagtggt    1680
```

```
gattattacc gccaaggccg cattgccaaa atgcctgtga agtggatcgc catcgagagc      1740
ctggcggacc gagtctacac aagcaaaagt gacgtgtggg cttttggcgt gaccatgtgg      1800
gaaataacaa cacggggaat gactccctat cccggagttc agaaccatga gatgtacgac      1860
taccttctcc acggccacag gctgaagcag cctgaggact gcttggatga actgtatgac      1920
atcatgtact cttgctggag tgctgatccc ttggatcgac ccaccttctc tgtgttgagg      1980
ctgcagctgg aaaagctctc cgagagtttg cctgatgcgc aggacaaaga atccatcatc      2040
tacatcaata cccagttgct agagagctgc gagggcatag ccaatgggcc ctcactcacg      2100
gggctagaca tgaacattga ccctgactcc atcattgcct cttgcacacc aggcgctgcc      2160
gtcagcgtgg tcacggcaga agttcacgag aacaaccttc gtgaggaaag atacatcttg      2220
aatgggggca atgaggaatg gaagatgtg tcctccactc cttttgctgc agtcacacct      2280
gaaaaggatg gtgtcttacc ggaggacaga ctcaccaaaa atggcgtctc ctggtctcac      2340
catagtacac tacccttggg gagcccatca ccagatgaac tttatttgt agatgactcc      2400 ttggaagact ctgaagttct gatgactagt ggtggatccg gaagtatggt gagcaagggc      2460
gaggagctgt tcaccggggt ggtgcccatc ctggtcgagc tggacggcga cgtaaacggc      2520
cacaagttca gcgtgtccgg cgagggcgag ggcgatgcca cctacggcaa gctgaccctg      2580
aagttcatct gcaccaccgg caagctgccc gtgccctggc ccaccctcgt gaccaccctg      2640
acctacggcg tgcagtgctt cagccgctac cccgaccaca tgaagcagca cgacttcttc      2700
aagtccgcca tgcccgaagg ctacgtccag gagcgcacca tcttcttcaa ggacgacggc      2760
aactacaaga cccgcgccga ggtgaagttc gagggcgaca ccctggtgaa ccgcatcgag      2820
ctgaagggca tcgacttcaa ggaggacggc aacatcctgg ggcacaagct ggagtacaac      2880
tacaacagcc acaacgtcta tatcatggcc gacaagcaga agaacggcat caaggtgaac      2940
ttcaagatcc gccacaacat cgaggacggc agcgtgcagc tcgccgacca ctaccagcag      3000
aacaccccca tcggcgacgg ccccgtgctg ctgcccgaca accactacct gagcacccag      3060
tccaagctga gcaaagaccc caacgagaag cgcgatcaca tggtcctgct ggagttcgtg      3120
accgccgccg ggatcactct cggcatggac gagctgtaca agtaa                     3165
```

<210> SEQ ID NO 18
<211> LENGTH: 2919
<212> TYPE: DNA
<213> ORGANISM: Artificial Sequence
<220> FEATURE:
<221> NAME/KEY: misc_feature
<223> OTHER INFORMATION: CD19-Bai1 CAR-P
<220> FEATURE:
<221> NAME/KEY: misc_feature
<223> OTHER INFORMATION: encodes the polypeptide of SEQE ID NO: 9

<400> SEQUENCE: 18

```
atggccttac cagtgaccgc cttgctcctg ccgctggcct tgctgctcca cgccgccagg       60
ccggacatcc agatgacaca gactacatcc tccctgtctg cctctctggg agacagagtc      120
accatcagtt gcagggcaag tcaggacatt agtaaatatt taaattggta tcagcagaaa      180
ccagatggaa ctgttaaact cctgatctac catacatcaa gattacactc aggagtccca      240
tcaaggttca gtggcagtgg gtctggaaca gattattctc tcaccattag caacctggag      300
caagaagata ttgccactta cttttgccaa cagggtaata cgcttccgta cacgttcgga      360
ggggggacca agctggagat cacaggtggc ggtggctcgg gcggtggtgg gtcgggtggc      420
```

```
ggcggatctg aggtgaaact gcaggagtca ggacctggcc tggtggcgcc ctcacagagc    480
ctgtccgtca catgcactgt ctcaggggtc tcattacccg actatggtgt aagctggatt    540
cgccagcctc cacgaaaggg tctggagtgg ctggagtaa  tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cggggggcgc agtgcacacg    900 aggggggctgg acttcgcctg tgatatctac atctgggcgc ccttggccgg gacttgtggg    960
gtccttctcc tgtcactggt tatcacccctt tactgcagaa gagaagtcca ggacgccgtc   1020
aaatgtcgag tggtagacag gcaggaggag ggtaacggtg attctggtgg gtcctttcag   1080
aacggccacg ctcagctcat gaccgatttt gagaaagacg tggatctggc atgtagaagt   1140
gtactgaaca aggacatcgc cgcatgtcgc actgcaacaa taacaggtac tctcaaacgg   1200
ccaagcctcc ccgaagaaga aaaacttaag ctggcacacg ccaagggccc accaacaaac   1260
ttcaatagtc tgccagctaa cgtgagtaag ctccatctcc atggcagtcc ccgctatcct   1320
ggcggacctc tccccgattt tcctaatcac agtcttactc tgaagagaga caaggctcct   1380
aaaagttcct ttgtagggga cggtgacata ttcaagaaac tggacagtga gctctctcga   1440
gcacaggaaa aggccttgga taccagctat gtgattctgc ccacagctac cgccacactg   1500
cggccaaagc caaagagga  gccaaaatat agtatccata tagaccaaat gccacaaacc   1560
cgactgatac acttgtcaac cgccccgaa  gctagccttc ccgctaggtc accacccagt   1620
cggcaacctc cctccggtgg tcctcctgag gcccctccag cccagccccc accacctcct   1680
cctccacctc ctcctccccc ccagcagcct ttgcctcccc caccaaatct tgagcctgct   1740
ccaccaagcc tcggggaccc cggggagcct gccgcacatc ctgggccaag taccggacca   1800
tctactaaga acgagaacgt agcaacactc tctgtttcat ctctggagcg ccgcaaatca   1860
agatatgcag agcttgattt cgagaagatc atgcatacta ggaaaagaca tcaagacatg   1920
ttccaagacc tgaatcggaa gctgcagcac gccgcagaga aggataaaga ggttctcgga   1980
cccgatagta agcctgaaaa acaacaaacc cccaataaaa ggccctggga aagtcttagg   2040
aaagcccatg gtacccctac ctgggttaag aaagagctgg aaccacttca accatcacca   2100
ttggagttga ggtcagtgga gtgggaaagg tcagggggcaa ccatacccctt ggtaggacaa   2160 gatatcatag acctgcagac tgaagtcggg tccggaagta tggtgagcaa gggcgaggag   2220
ctgttcaccg gggtggtgcc catcctggtc gagctggacg gcgacgtaaa cggccacaag   2280
ttcagcgtgt ccggcgaggg cgagggcgat gccacctacg gcaagctgac cctgaagttc   2340
atctgcacca ccggcaagct gcccgtgccc tggcccaccc tcgtgaccac cctgacctac   2400
ggcgtgcagt gcttcagccg ctaccccgac cacatgaagc agcacgactt cttcaagtcc   2460
gccatgcccg aaggctacgt ccaggagcgc accatcttct tcaaggacga cggcaactac   2520
aagacccgcg ccgaggtgaa gttcgagggc gacaccctgg tgaaccgcat cgagctgaag   2580
ggcatcgact tcaaggagga cggcaacatc ctggggcaca gctggagta  caactacaac   2640 agccacaacg tctatatcat ggccgacaag cagaagaacg gcatcaaggt gaacttcaag   2700
atccgccaca catcgagga  cggcagcgtg cagctcgccg accactacca gcagaacacc   2760
cccatcggcg acggccccgt gctgctgccc gacaaccact acctgagcac ccagtccaag   2820
```

```
ctgagcaaag accccaacga gaagcgcgat cacatggtcc tgctggagtt cgtgaccgcc    2880
gccgggatca ctctcggcat ggacgagctg tacaagtaa                          2919
```

<210> SEQ ID NO 19
<211> LENGTH: 4
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 19

Gly Gly Gly Ser
1

<210> SEQ ID NO 20
<211> LENGTH: 4
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 20

Ser Gly Gly Gly
1

<210> SEQ ID NO 21
<211> LENGTH: 5
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 21

Gly Gly Gly Gly Ser
1               5

<210> SEQ ID NO 22
<211> LENGTH: 5
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 22

Ser Gly Gly Gly Gly
1               5

<210> SEQ ID NO 23
<211> LENGTH: 6
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 23

Gly Gly Gly Gly Gly Ser
1               5

<210> SEQ ID NO 24
<211> LENGTH: 6
<212> TYPE: PRT

```
<213> ORGANISM: Artificial Sequence
<220> FEATURE:
<221> NAME/KEY: misc_feature
<223> OTHER INFORMATION: peptide linker

<400> SEQUENCE: 24

Ser Gly Gly Gly Gly Gly
1               5

<210> SEQ ID NO 25
<211> LENGTH: 7
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 25

Gly Gly Gly Gly Gly Gly Ser
1               5

<210> SEQ ID NO 26
<211> LENGTH: 7
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 26

Ser Gly Gly Gly Gly Gly Gly
1               5

<210> SEQ ID NO 27
<211> LENGTH: 5
<212> TYPE: PRT
<213> ORGANISM: Artificial Sequence
<220> FEATURE:
<221> NAME/KEY: misc_feature
<223> OTHER INFORMATION: peptide linker
<220> FEATURE:
<221> NAME/KEY: misc_feature
<222> LOCATION: (1)..(5)
<223> OTHER INFORMATION: This polypeptide sequence may be present one or
      more times

<400> SEQUENCE: 27

Gly Gly Gly Gly Ser
1               5

<210> SEQ ID NO 28
<211> LENGTH: 5
<212> TYPE: PRT
<213> ORGANISM: Artificial Sequence
<220> FEATURE:
<221> NAME/KEY: misc_feature
<223> OTHER INFORMATION: peptide linker
<220> FEATURE:
<221> NAME/KEY: misc_feature
<222> LOCATION: (1)..(5)
<223> OTHER INFORMATION: This polypeptide sequence may be present one or
      more times

<400> SEQUENCE: 28

Ser Gly Gly Gly Gly
1               5

<210> SEQ ID NO 29
<211> LENGTH: 25
```

```
<212> TYPE: PRT
<213> ORGANISM: Artificial Sequence
<220> FEATURE:
<221> NAME/KEY: misc_feature
<223> OTHER INFORMATION: peptide linker
<220> FEATURE:
<221> NAME/KEY: misc_feature
<223> OTHER INFORMATION: Xaa is any amino acid that can be
      inserted into the sequence and not result in a polypeptide
      including the sequence "GSG"
<220> FEATURE:
<221> NAME/KEY: misc_feature
<222> LOCATION: (1)..(20)
<223> OTHER INFORMATION: These residues may be present or absent

<400> SEQUENCE: 29

Gly Gly Gly Xaa Xaa Gly Gly Xaa Xaa Gly Gly Gly Xaa Xaa Gly
1               5                   10                  15

Gly Gly Xaa Xaa Gly Gly Gly Gly Ser
            20                  25

<210> SEQ ID NO 30
<211> LENGTH: 25
<212> TYPE: PRT
<213> ORGANISM: Artificial Sequence
<220> FEATURE:
<221> NAME/KEY: misc_feature
<223> OTHER INFORMATION: peptide linker
<220> FEATURE:
<221> NAME/KEY: misc_feature
<223> OTHER INFORMATION: Xaa is any amino acid that can be
      inserted into the sequence and not result in a polypeptide
      including the sequence "GSG".
<220> FEATURE:
<221> NAME/KEY: misc_feature
<222> LOCATION: (6)..(25)
<223> OTHER INFORMATION: These residues may be present or absent

<400> SEQUENCE: 30

Gly Gly Gly Gly Ser Xaa Gly Gly Ser Xaa Gly Gly Ser Xaa
1               5                   10                  15

Gly Gly Gly Ser Xaa Gly Gly Gly Ser
            20                  25

<210> SEQ ID NO 31
<211> LENGTH: 25
<212> TYPE: PRT
<213> ORGANISM: Artificial Sequence
<220> FEATURE:
<221> NAME/KEY: misc_feature
<223> OTHER INFORMATION: peptide linker
<220> FEATURE:
<221> NAME/KEY: misc_feature
<222> LOCATION: (1)..(20)
<223> OTHER INFORMATION: These residues may be present or absent

<400> SEQUENCE: 31

Gly Gly Gly Pro Ser Gly Gly Pro Ser Gly Gly Pro Ser Gly
1               5                   10                  15

Gly Gly Pro Ser Gly Gly Gly Gly Ser
            20                  25

<210> SEQ ID NO 32
<211> LENGTH: 25
<212> TYPE: PRT
<213> ORGANISM: Artificial Sequence
<220> FEATURE:
<221> NAME/KEY: misc_feature
<223> OTHER INFORMATION: peptide linker
<220> FEATURE:
```

```
<221> NAME/KEY: misc_feature
<222> LOCATION: (1)..(20)
<223> OTHER INFORMATION: These residues may be present or absent

<400> SEQUENCE: 32

Gly Gly Gly Gly Gln Gly Gly Gly Gln Gly Gly Gly Gln Gly
1               5                   10                  15

Gly Gly Gly Gln Gly Gly Gly Gly Ser
            20                  25

<210> SEQ ID NO 33
<211> LENGTH: 25
<212> TYPE: PRT
<213> ORGANISM: Artificial Sequence
<220> FEATURE:
<221> NAME/KEY: misc_feature
<223> OTHER INFORMATION: peptide linker
<220> FEATURE:
<221> NAME/KEY: misc_feature
<222> LOCATION: (1)..(20)
<223> OTHER INFORMATION: These residues may be present or absent

<400> SEQUENCE: 33

Gly Gly Gly Gly Ala Gly Gly Gly Ala Gly Gly Gly Ala Gly
1               5                   10                  15

Gly Gly Gly Ala Gly Gly Gly Gly Ser
            20                  25

<210> SEQ ID NO 34
<211> LENGTH: 25
<212> TYPE: PRT
<213> ORGANISM: Artificial Sequence
<220> FEATURE:
<221> NAME/KEY: misc_feature
<223> OTHER INFORMATION: peptide linker
<220> FEATURE:
<221> NAME/KEY: misc_feature
<222> LOCATION: (6)..(25)
<223> OTHER INFORMATION: These residues may be present or absent

<400> SEQUENCE: 34

Gly Gly Gly Gly Ser Pro Gly Gly Gly Ser Pro Gly Gly Gly Ser Pro
1               5                   10                  15

Gly Gly Gly Ser Pro Gly Gly Gly Ser
            20                  25

<210> SEQ ID NO 35
<211> LENGTH: 15
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 35

Gly Gly Gly Gly Ala Gly Gly Gly Gly Ala Gly Gly Gly Gly Ser
1               5                   10                  15

<210> SEQ ID NO 36
<211> LENGTH: 15
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 36
```

Gly Gly Gly Gly Gln Gly Gly Gly Gln Gly Gly Gly Ser
1               5                   10                  15

<210> SEQ ID NO 37
<211> LENGTH: 15
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 37

Gly Gly Gly Pro Ser Gly Gly Pro Ser Gly Gly Gly Gly Ser
1               5                   10                  15

<210> SEQ ID NO 38
<211> LENGTH: 15
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 38

Gly Gly Gly Gly Ser Pro Gly Gly Ser Pro Gly Gly Ser
1               5                   10                  15

<210> SEQ ID NO 39
<211> LENGTH: 5
<212> TYPE: PRT
<213> ORGANISM: Artificial Sequence
<220> FEATURE:
<221> NAME/KEY: misc_feature
<223> OTHER INFORMATION: peptide linker

<400> SEQUENCE: 39

Gly Ser Gly Gly Ser
1               5

<210> SEQ ID NO 40
<211> LENGTH: 6
<212> TYPE: PRT
<213> ORGANISM: Artificial Sequence
<220> FEATURE:
<223> OTHER INFORMATION: peptide linker

<400> SEQUENCE: 40

Ser Gly Gly Ser Gly Ser
1               5

<210> SEQ ID NO 41
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 41
ggtggcggtg gctcgggcgg tggtgggtcg ggtggcggcg gatct          45

<210> SEQ ID NO 42
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 42

```
Asn His Arg Asn Arg Arg Arg
1               5

<210> SEQ ID NO 43
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 43
aaccacagga accgaagacg t                                              21

<210> SEQ ID NO 44
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 44
aaaatgtcca aggatggtaa gaaaaagaag aagaagtcaa aaaccaagtg tgttatcatg    60

<210> SEQ ID NO 45
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 45
ggaagcggag ctactaactt cagcctgctg aagcaggctg agacgtgga ggagaaccct     60 ggacct                                                               66
```